(12) United States Patent
Wagner et al.

(10) Patent No.: US 10,005,741 B2
(45) Date of Patent: Jun. 26, 2018

(54) THERAPEUTIC COMPOUNDS

(71) Applicant: ARIZONA BOARD OF REGENTS ON BEHALF OF ARIZONA STATE UNIVERSITY, Scottsdale, AZ (US)

(72) Inventors: Carl Wagner, Glendale, AZ (US); Pamela Marshall, Peoria, AZ (US); Peter Jurutka, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days. days.

(21) Appl. No.: 15/873,704

(22) Filed: Jan. 17, 2018

(65) Prior Publication Data

US 2018/0141921 A1    May 24, 2018

Related U.S. Application Data

(62) Division of application No. 15/121,324, filed as application No. PCT/US2015/017832 on Feb. 26, 2015, now Pat. No. 9,908,856.

(60) Provisional application No. 61/945,020, filed on Feb. 26, 2014.

(51) Int. Cl.

| | |
|---|---|
| *C07D 249/18* | (2006.01) |
| *C07D 209/08* | (2006.01) |
| *C07D 213/48* | (2006.01) |
| *C07D 213/74* | (2006.01) |
| *C07D 213/79* | (2006.01) |
| *C07D 215/227* | (2006.01) |
| *C07D 235/10* | (2006.01) |
| *C07D 239/42* | (2006.01) |
| *C07D 241/20* | (2006.01) |
| *C07D 241/28* | (2006.01) |
| *C07D 307/79* | (2006.01) |
| *C07D 333/54* | (2006.01) |
| *C07C 57/50* | (2006.01) |
| *C07D 223/06* | (2006.01) |
| *C07C 309/31* | (2006.01) |
| *C07C 223/06* | (2006.01) |
| *A61K 31/505* | (2006.01) |

(52) U.S. Cl.
CPC .......... *C07D 249/18* (2013.01); *A61K 31/505* (2013.01); *C07C 57/50* (2013.01); *C07C 223/06* (2013.01); *C07C 309/31* (2013.01); *C07D 209/08* (2013.01); *C07D 213/48* (2013.01); *C07D 213/74* (2013.01); *C07D 213/79* (2013.01); *C07D 215/227* (2013.01); *C07D 235/10* (2013.01); *C07D 239/42* (2013.01); *C07D 241/20* (2013.01); *C07D 241/28* (2013.01); *C07D 307/79* (2013.01); *C07D 333/54* (2013.01); *C07C 2602/10* (2017.05)

(58) Field of Classification Search
CPC .. C07D 249/18; C07D 209/08; C07D 213/48; C07D 213/74; C07D 213/79; C07D 215/227; C07D 235/10; C07D 239/42; C07D 241/20; C07D 241/28; C07D 307/79; C07D 333/54; C07C 57/50; C07C 223/06; C07C 309/31
See application file for complete search history.

(56) References Cited

U.S. PATENT DOCUMENTS

| | | | |
|---|---|---|---|
| 4,938,949 | A | 7/1990 | Borch et al. |
| 4,980,509 | A | 12/1990 | Maignan |
| 5,587,367 | A | 12/1996 | Reuchert |
| 5,981,776 | A | 11/1999 | Diaz et al. |
| 8,475,775 | B1 | 7/2013 | Brouillette |
| 9,908,856 | B2 | 3/2018 | Wagner et al. |
| 2003/0135053 | A1 | 7/2003 | Bernardon |
| 2010/0029689 | A1 | 2/2010 | Hopper |
| 2010/0105728 | A1 | 4/2010 | Lagu |
| 2010/0120742 | A1 | 5/2010 | Kakuta et al. |
| 2010/0144821 | A1 | 6/2010 | Carter et al. |

FOREIGN PATENT DOCUMENTS

| | | |
|---|---|---|
| EP | 1180520 A1 | 2/2002 |
| JP | 2010111588 A | 5/2010 |
| JP | 2014076953 A | 5/2014 |
| WO | 1998045242 A1 | 10/1998 |
| WO | 1999051562 A1 | 10/1999 |
| WO | 2005011573 A2 | 2/2005 |
| WO | 2006036394 A2 | 4/2006 |
| WO | 2011103321 A1 | 8/2011 |
| WO | 2013040227 A2 | 3/2013 |
| WO | 2013040227 A3 | 7/2013 |
| WO | 2015130973 A1 | 9/2015 |

OTHER PUBLICATIONS

Atigadda, et al., "Conformationally Defined Retinoic Acid Analogues. 5. Large-Scale Synthesis and Mammary Cancer Chemopreventive Activity for (2E,4E,6Z,8E)-8-(3',4'-Dihydro-1'(2'H)-naphthalen-1'-ylidene)-3,7-dimethyl-2,4,6-octatrienoic Acid (9cUAB30)", Journal of Medicinal Chemistry 46(17), 3766-3769 (2003).

Atigadda, et al., "Methyl substitution of a rexinoid agonist improves potency and reveals site of lipid toxicity", Journal of Medicinal Chemistry 57(12), 5370-5380 (2014).

Boehm, et al., "Design and Synthesis of Potent Retinoid X Receptor Selective Ligands That Induce Apoptosis in Leukemia Cells", Journal of Medicinal Chemistry 38, 3146-55 (1995).

(Continued)

*Primary Examiner* — Timothy R Rozof
(74) *Attorney, Agent, or Firm* — Viksnins Harris Padys Malen LLP

(57) ABSTRACT

The invention provides compounds and compositions that are useful for treating conditions including Alzheimer's disease, Parkinson's disease, diabetes, cancer, and psychotic disorders such as schizophrenia.

9 Claims, 3 Drawing Sheets

(56) References Cited

OTHER PUBLICATIONS

Boehm, et al., "Synthesis and Structure-Activity Relationships of Novel Retinoid X Receptor-Selective Retinoids", Journal of Medicinal Chemistry 37, 2930-2941 (1994).
Cesario, et al., "Differentiation and growth inhibition mediated via the RXR:PPARgamma heterodimer in colon cancer", Cancer Letters 240(2), 225-233 (2006).
Esteva, et al., "Multicenter Phase II Study of Oral Bexarotene for Patients With Metastatic Breast Cancer", Journal of Clinical Oncology 21(6), 999-1006 (2003).
Fantini, et al., "Bexarotene Blocks Calcium-Permeable Ion Channels Formed by Neurotoxic Alzheimer's beta-Amyloid Peptides", ACS Chemical Neuroscience 5(3), 216-224 (2014).
Fujii, et al., "Modification at the acidic domain of RXR agonists has little effect on permissive RXR-heterodimer activation", Bioorganic & Medicinal Chemistry Letters 20, 5139-5142 (2010).
Furmick, et al., "Modeling, synthesis and biological evaluation of potential retinoid X receptor-selective agonists: novel halogenated analogues of 4-[1-(3,5,5,8,8-pentamethyl-5,6,7,8-tetrahydro-2-naphthyl)ethynyl]benzoic acid (bexarotene)", ChemMedChem 7(9), 1551-1566 (2012).
Garcia, et al., "Pyrazine arotinoids with inverse agonist activities on the retinoid and rexinoid receptors", Chembiochem 10, 1252-1259 (2009).
Gorman, et al., "In vitro metabolic characterization, phenotyping, and kinetic studies of 9cUAB30, a retinoid X receptor-specific retinoid", Drug Metabolism & Disposition 35(7), 1157-1164 (2007).
Grubbs, et al., "9cUAB30, an RXR specific retinoid, and/or tamoxifen in the prevention of methylnitrosourea-induced mammary cancers", Cancer Letters 201, 17-24 (2003).
Hansen, et al., "The low-toxicity 9-cis UAB30 novel retinoid down-regulates the DNA methyltransferases and has antitelomerase activity in human breast cancer cells", International Journal of Oncology 30(3), 641-650 (2007).
Jurutka, et al., "Modeling, synthesis, and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene) and (E)-3-(3-(1,2,3,4-tetrahydro-1,1,4,", Journal of Medicinal Chemistry 56, 8432-8454 (2013).
Kakuta, et al., "RXR Partial Agonist CBt-PMN Exerts Therapeutic Effects on Type 2 Diabetes without the Side Effects of RXR Full Agonists", ACS Medicinal Chemistry Letters 3, 427-432 (2012).
Kakuta, "Western-style Chinese (Kampo) medicine targeting retinoid X receptors (RXRs)", 248th ACS National Meeting, MEDI 102, San Francisco, CA. (2014).
Kapetanovic, et al., "Murine Oncogenicity and Pharmacokinetics Studies of 9-cis-UAB30, an RXR Agonist, for Breast Cancer Chemoprevention", International Journal of Toxicology 29(2), 157-164 (2010).
Khuri, et al., "Multi-Institutional Phase I/II Trial of Oral Bexarotene in Combination With Cisplatin and Vinorelbine in Previously Untreated Patients With Advanced Non-Small-Cell Lung Cancer", Journal of Clinical Oncology 19, 2626-2637 (2001).
Koch, et al., "Synthesis of Retinoid X Receptor-Specific Ligands That Are Potent Inducers of Adipogenesis in 3T3-L1 Cells", Journal of Medicinal Chemistry 42, 742-750 (1999).
Kolesar, et al., "A pilot, first-in-human, pharmacokinetic study of 9cUAB30 in healthy volunteers", Cancer Prevention Research 3(12), 1565-1570 (2010).
Lagu, et al., "RXR-LXR heterodimer modulators for the potential treatment of dyslipidemia", Bioorganic & Medicinal Chemistry Letters 17, 3497-3503 (2007).
Lerner, et al., "Bexarotene as add-on to antipsychotic treatment in schizophrenia patients: a pilot open-label trial.", Clinical Neuropharmacology 31(1), 25-33 (2008).
Liby, et al., "Synthetic Triterpenoids Prolong Survival in a Transgenic Mouse Model of Pancreatic Cancer", Cancer Prevention Research 3(11), 1427-1434 (2010).
Lindeblad, et al., "Assessment of oral toxicity and safety of 9-cis-UAB30, a potential chemopreventive agent, in rat and dog studies", Drug and Chemical Toxicology 34(3), 300-310 (2011).
McFarland, et al., "Low Dose Bexarotene Treatment Rescues Dopamine Neurons and Restores Behavioral Function in Models of Parkinson's Disease", ACS Chemical Neuroscience 4(11), 1430-1438 (2013).
Michellys, et al., "Design, synthesis, and structure-activity relationship studies of novel 6,7-locked-[7-(2-alkoxy-3,5-dialkylbenzene)-3-methylocta]-2,4,6-trienoic acids", Journal of Medicinal Chemistry 46, 4087-4103 (2003).
Michellys, et al., "Novel (2E,4E,6Z)-7-(2-alkoxy-3,5-dialkylbenzene)-3-methylocta-2,4,6-trienoic acid retinoid X receptor modulators are active in models of type 2 diabetes", Journal of Medicinal Chemistry 46, 2683-2696 (2003).
Mortelmans and Zeiger, "The Ames Salmonella/microsome mutagenicity assay", Mutation Research 455(1-2), 29-60 (2000).
Muccio, et al., "Conformationally Defined Retinoic Acid Analogues. 4. Potential New Agents for Acute Promyelocytic and Juvenile Myelomonocytic Leukemias", Journal of Medicinal Chemistry 41(10), 1679-1687 (1998).
Mukherjee, et al., "Sensitization of diabetic and obese mice to insulin by retinoid X receptor agonists", Nature 386, 407-410 (1997).
Ohta, et al., "Diphenylamine-based retinoid antagonists: regulation of RAR and RXR function depending on the N-substituent", Bioorganic & Medicinal Chemistry 19, 2501-2507 (2011).
Ohta, et al., "Potent Retinoid Synergists with a Diphenylamine Skeleton", Biological & Pharmaceutical Bulletin 21(5), 544-546 (1998).
Ohwasa, et al., "Mechanism of retinoid X receptor partial agonistic action of 1-(3,5,5,8,8-pentamethyl-5,6,7,8-tetrahydro-2-naphthyl)-1H-benzotriazole-5-carboxylic acid and structural development to increase potency", Journal of Medicinal Chemistry 56(5), 1865-1877 (2013).
Patent Cooperation Treaty, International Searching Authority, Search Report and Written Opinion for PCT/US2015/17832, 13 pages, dated May 27, 2015.
Perlmann and Jansson, "A novel pathway for vitamin A signaling mediated by RXR heterodimerization with NGFI-B and NURR1", Genes & Development 9, 769-782 (1995).
Santin, et al., "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers", Journal of Medicinal Chemistry 52, 3150-3158 (2009).
Wagner, et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene)", Journal of Medicinal Chemistry 52(19), 5950-5966 (2009).
Wallen-Mackenzie, et al., "Nurr1-RXR heterodimers mediate RXR ligand-induced signaling in neuronal cells", Genes & Development 17, 3036-3047 (2003).
Whitworth, et al., "The impact of novel retinoids in combination with platinum chemotherapy on ovarian cancer stem cells", Gynecologic Oncology 125, 226-230 (2012).
Yen, et al., "A selective retinoid X receptor agonist bexarotene (Targretin) prevents and overcomes acquired paclitaxel (Taxol) resistance in human non-small cell lung cancer", Clinical Cancer Research 10(24), 8656-8664 (2004).

THERAPEUTIC COMPOUNDS

CROSS REFERENCE TO RELATED APPLICATIONS

This is a divisional application of U.S. Non-Provisional application Ser. No. 15/121,324, filed on 24 Aug. 2016, which is a National Stage Application under 35 USC 371(c) of International Application No. PCT/US15/017832, having an International Filing Date of 26 Feb. 2015, and which claims the benefit of priority to U.S. Provisional Application No. 61/945,020, filed on 26 Feb. 2014. The entire content of the applications referenced above are hereby incorporated by reference herein.

GOVERNMENT FUNDING

This invention was made with government support under R15 CA139364 awarded by the National Institutes of Health. The government has certain rights in the invention.

BACKGROUND OF THE INVENTION

The human retinoid X receptors (hRXRs) consist of three identified isoforms (α, β, γ) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Bexarotene has been used to treat cutaneous T cell lymphoma. Bexarotene has also been shown to be useful for treatment of Alzheimer's Disease (AD). However, bexarotene treatment results in untoward side effects, possibly due to its nonspecific nature of binding RXR in several states, including the RXR-RXR homodimer form as well as RXR heterodimer forms.

McFarland, K., et al, *ACS Chem. Neurosci.*, 2013, 4(11), 1430-1438 treated a rat model of Parkinson's disease (PD) with bexarotene and noted marked improvement in the PD symptoms. Specifically the bexarotene restored dopamine cells and natural behavior in the PD model. As importantly, the bexarotene dose that accomplished this was quite low, alleviating some side effects. The researchers demonstrated that these symptoms were alleviated by bexarotene binding to RXR and its heterodimerizing with another nuclear receptor called Nurr1.

PD is a chronic, debilitating disorder in which the neurons of the central nervous system degenerate over time. Specifically the dopamine secreting cells of the midbrain slowy die off, leaving the patient with a wide range of symptoms due to the lack of dopamine. Early symptoms include shaking, off balance gait, and slowless of muscles. Over time, symptoms worsen and additional symptoms including demetia and/or depression can develop. Treatments include dopamine agonists, given to try to ameliorate the effect of loss of dopamine in the system.

Currently there is a need for additional chemical agents that are useful for treating conditions including Alzheimer's disease, Parkinson's disease, diabetes, cancer, and psychotic disorders such as schizophrenia.

SUMMARY OF THE INVENTION

The present invention provides compounds that are useful for treating conditions including Alzheimer's disease, Parkinson's disease, diabetes, cancer, and psychotic disorders such as schizophrenia.

Accordingly, one embodiment provides a compound of the invention which is compound selected from formulae I-X:

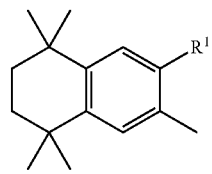

I wherein:
$R^1$ is a nine-membered bicyclic heteroaryl ring that is substituted with one or more carboxy and that is optionally substituted with one or more groups independently selected from halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);

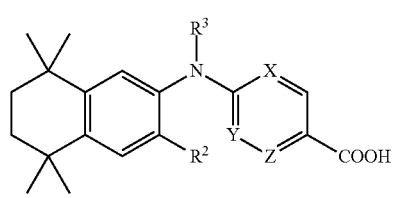

II wherein:
X is N, Y is CH and Z is N;
X is N, Y is CH and Z is CH;

X is N, Y is N and Z is CH;

X is CH, Y is CH and Z is CH;

$R^2$ is H or methyl; and $R^3$ is ethyl that is optionally substituted with one or more groups independently selected from F, Cl, and Br; wherein the ring containing X, Y, and Z is optionally substituted on carbon with one or more groups independently selected from halo;

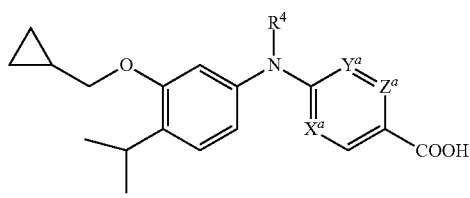

III wherein:

$X^a$ is CH, $Y^a$ is CH and $Z^a$ is CH;

$X^a$ is CH, $Y^a$ is CH and $Z^a$ is N;

$X^a$ is N, $Y^a$ is N and $Z^a$ is CH; and $R^4$ is ethyl that is optionally substituted with one or more groups independently selected from F, Cl, and Br; wherein the ring containing $X^a$, $Y^a$, and $Z^a$ is optionally substituted on carbon with one or more groups independently selected from halo;

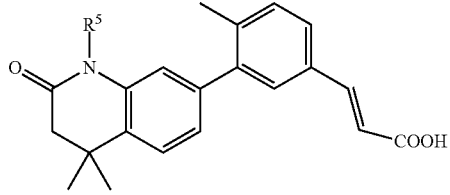

IV wherein:

$R^5$ is ethyl, propyl, or isopropyl;

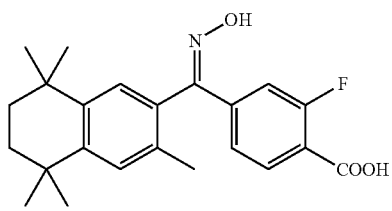

V

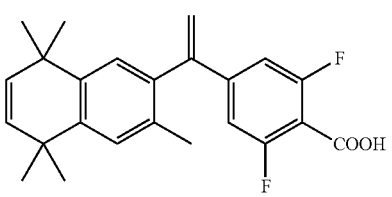

VI

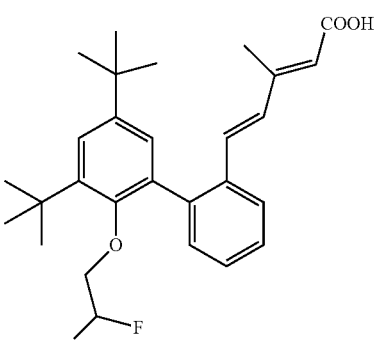

VII

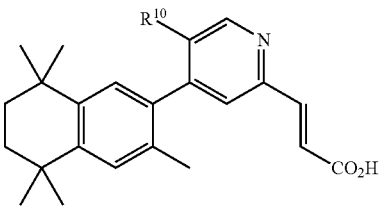

VIII

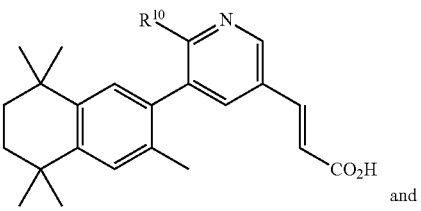

IX

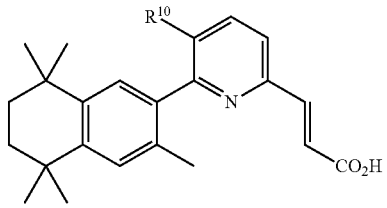

and

X wherein:

$R^{10}$ is H or methyl;

and salts thereof;

provided the compound is not:

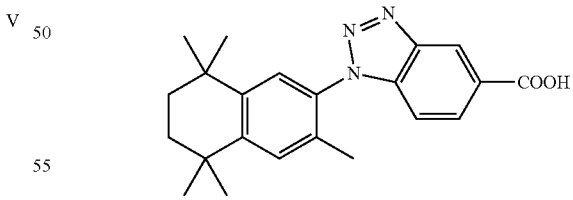

or

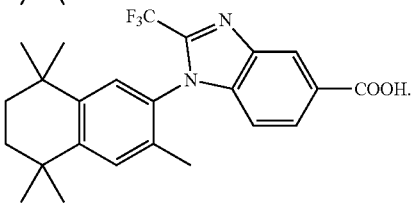

Another embodiment provides a compound of the invention which is a compound of formula (XI):

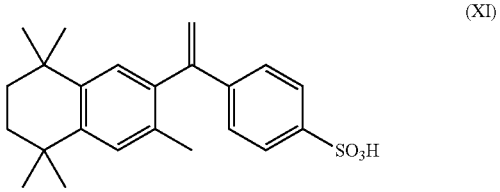 [SMILES: C=C(c1ccc(S(=O)(=O)O)cc1)c1cc2c(cc1C)C(C)(C)CCC2(C)C]

(XI)

or a salt thereof.

Another embodiment provides a compound of the invention which is a compound of formula (XII):

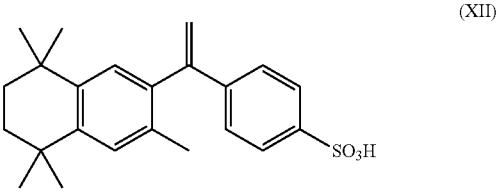 [SMILES: C=C(c1ccc(S(=O)(=O)O)cc1)c1cc2c(cc1C)C(C)(C)CCC2(C)C]

(XII)

or a salt thereof.

The invention also provides a pharmaceutical composition comprising a compound of formulae I-XII, or a pharmaceutically acceptable salt thereof, in combination with a pharmaceutically acceptable diluent or carrier.

The invention also provides a method for treating Alzheimer's disease, Parkinson's disease, diabetes, cancer, or a psychotic disorder in an animal (e.g. a mammal such as a human) comprising administering a compound of formulae I-XII, or a pharmaceutically acceptable salt thereof, to the animal.

The invention also provides a compound of formulae I-XII, or a pharmaceutically acceptable salt thereof, for the prophylactic or therapeutic treatment of Alzheimer's disease, Parkinson's disease, diabetes, cancer, or a psychotic disorder.

The invention also provides the use of a compound of formulae I-XII, or a pharmaceutically acceptable salt thereof, to prepare a medicament useful for treating Alzheimer's disease, Parkinson's disease, diabetes, cancer, or a psychotic disorder in an animal.

The invention also provides a method for activating RXR in a cell comprising contacting the cell in vitro or in vivo with an effective amount of a compound of formulae I-XII, or a salt thereof.

The invention also provides a compound of formulae I-XII, or a pharmaceutically acceptable salt thereof, for use in medical therapy.

The invention also provides processes and novel intermediates that are useful for preparing a compound of formulae I-XII, or a salt thereof.

DETAILED DESCRIPTION

Figure 1:
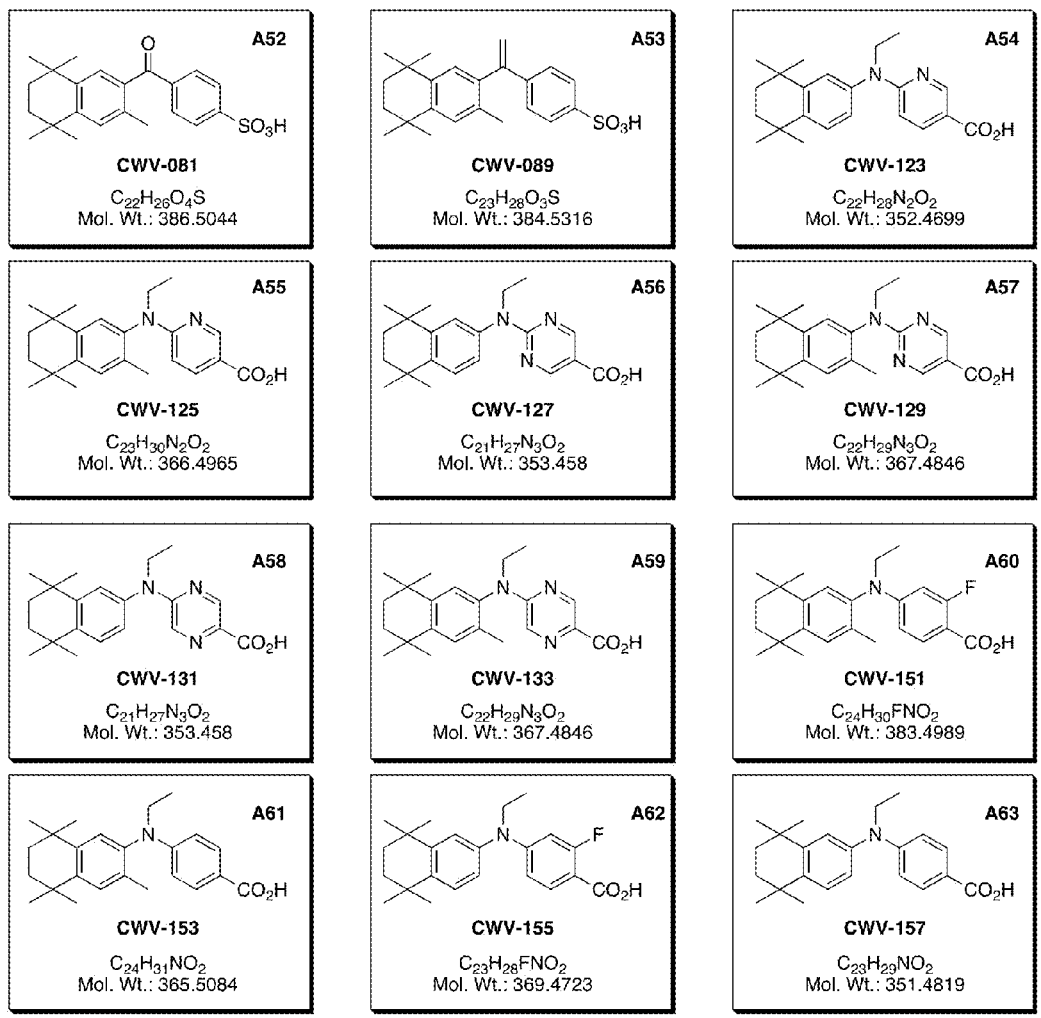
FIG. 1 Illustrates representative compounds of the invention

The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "6-membered heteroaryl ring" includes rings with at least two carbon atoms and 1, 2, 3, or 4 heteroatoms (e.g. N, O, or S).

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$ cycloalkyl can be cyclopropyl, cyclobutyl, cyclopentyl, or cyclohexyl; $(C_3-C_6)$ cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$ alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be pyrazinyl, pyridazine, triazine, pyridyl, or pyrimidinyl, or an N-oxide thereof.

In one specific embodiment the compound of the invention is a compound of formulae Ia, Ib, or Ic:

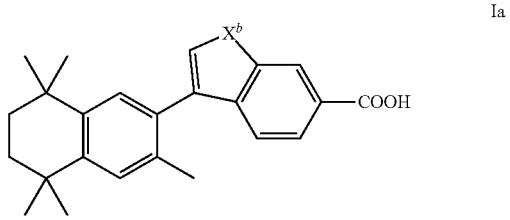

Ia

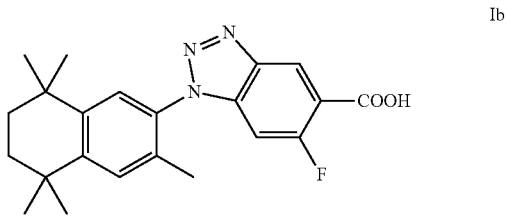

Ib or

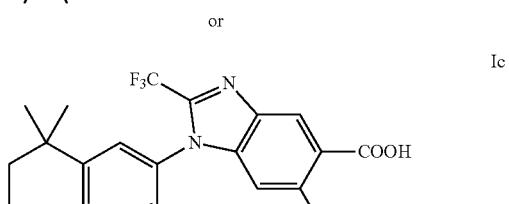

Ic wherein:

$X^b$ is S, O, or NH;

or a salt thereof.

In one specific embodiment the compound of the invention is a compound of formulae IIa, IIb, or IIc:

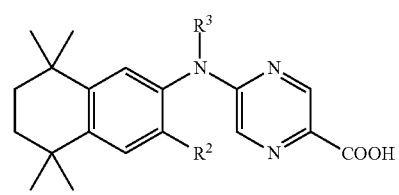
IIa

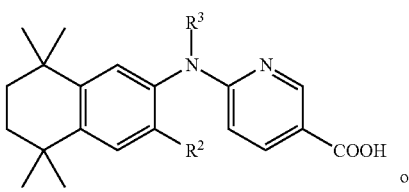
IIb or

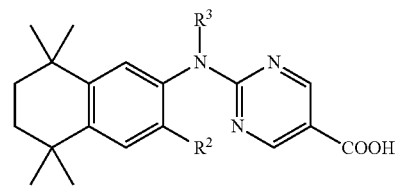
IIc wherein:

$R^2$ is H or methyl; and $R^3$ is ethyl that is optionally substituted with one or more groups independently selected from F, Cl, and Br;

or a salt thereof.

In one specific embodiment the compound of the invention is a compound of formulae IIIa, IIIb, or IIIc:

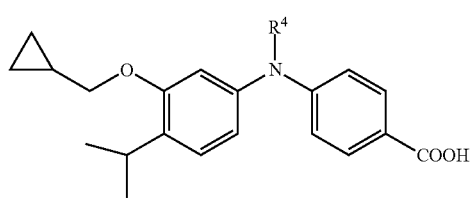
IIIa

IIIb or

IIIc wherein:

$R^4$ is ethyl that is optionally substituted with one or more groups independently selected from F, Cl, and Br;

or a salt thereof.

In one specific embodiment the compound of the invention is a compound of formula IV, wherein $R^5$ is ethyl or isopropyl; or a salt thereof.

In one specific embodiment the compound of the invention is selected from:

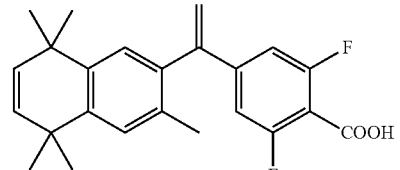

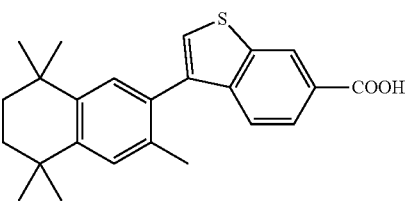

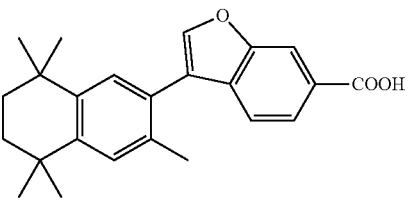

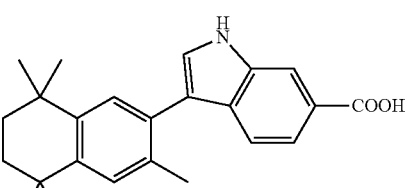

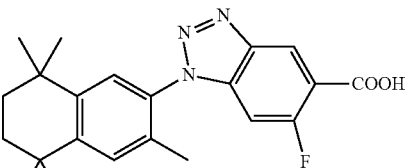

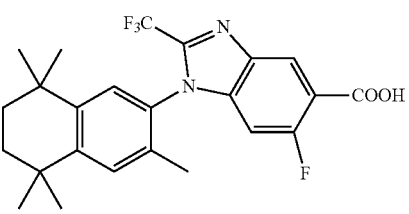

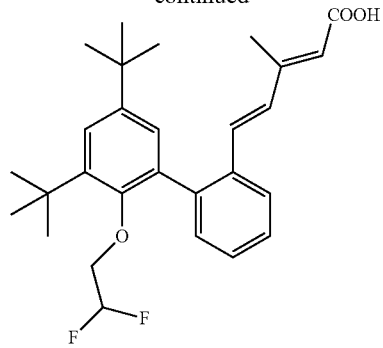
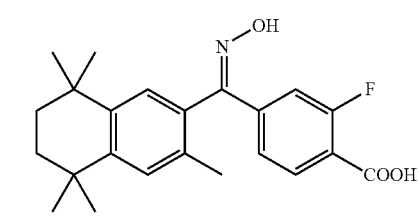
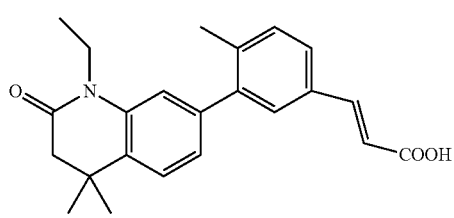
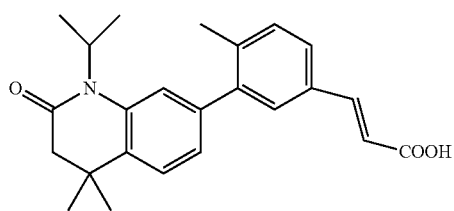
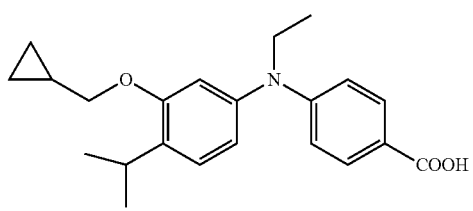
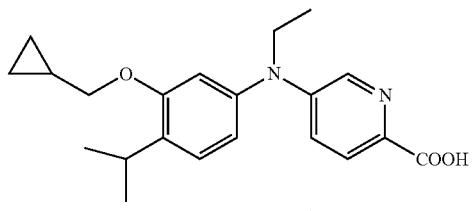
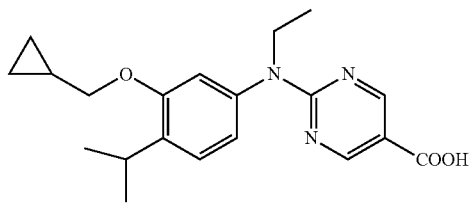
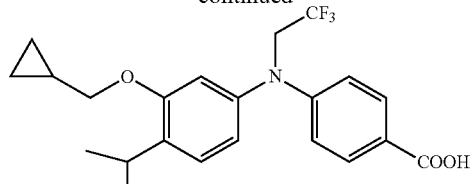
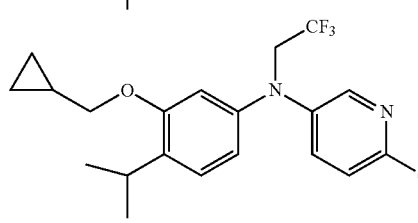
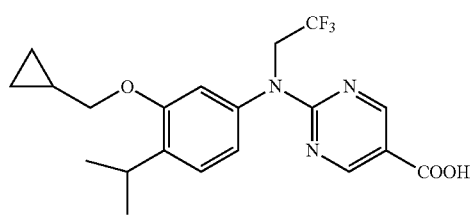
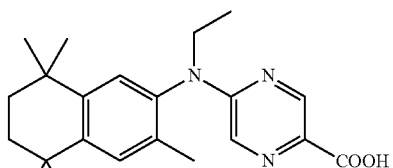
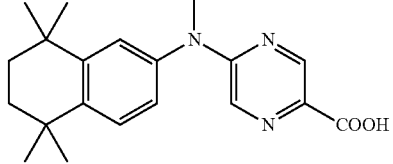
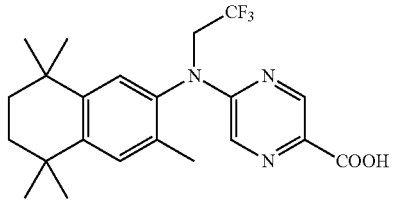
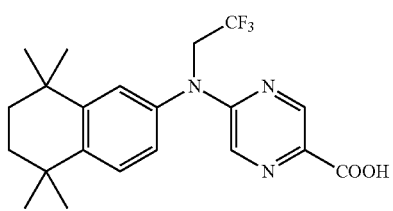

-continued

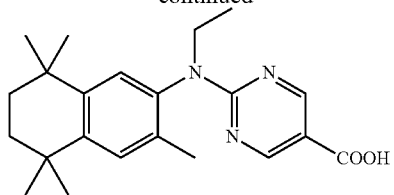

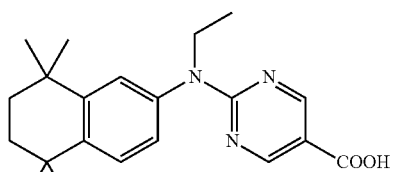

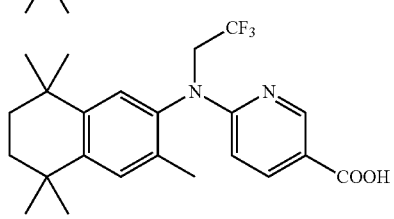

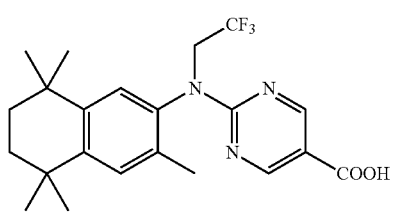

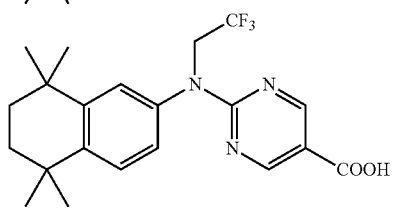

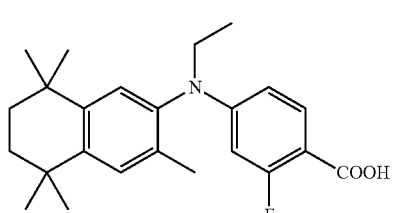

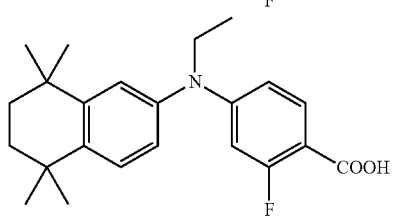

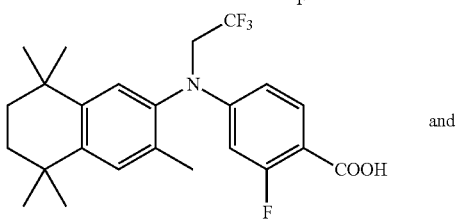

and

-continued

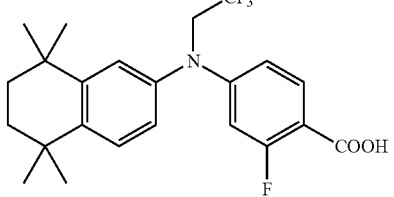

and salts thereof.

In one specific embodiment the compound of the invention is selected from:

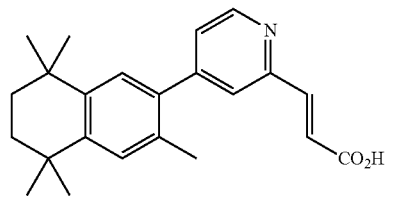

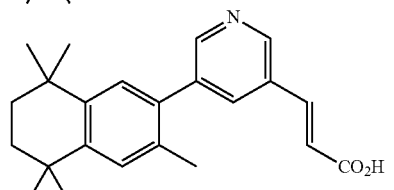

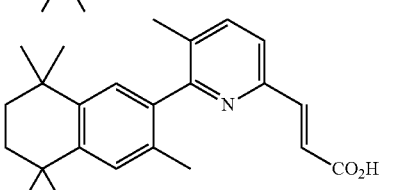

and

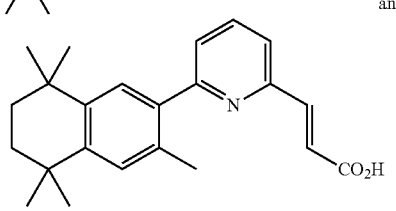

and salts thereof.

In one specific embodiment the compound of the invention is selected from compounds of formulae I-X:

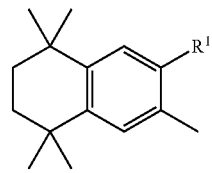

I wherein:

R¹ is a nine-membered bicyclic heteroaryl ring that is substituted with one or more carboxy and that is optionally substituted with one or more groups independently selected from halo, hydroxy, cyano, nitro, $(C_1-C_6)$alkyl, $(C_3-C_6)$ cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);

II

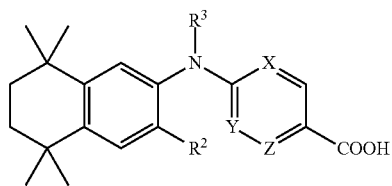

wherein:
X is N, Y is C and Z is N;
X is N, Y is C and Z is C;
X is N, Y is N and Z is C;
$R^2$ is H or methyl; and
$R^3$ is ethyl that is optionally substituted with one or more groups independently selected from F, Cl, and Br;

III

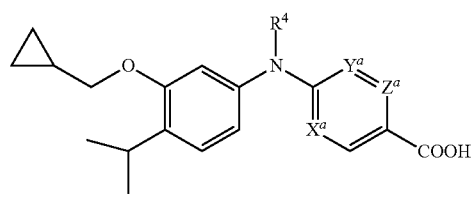

wherein:
$X^a$ is C, $Y^a$ is C and $Z^a$ is C;
$X^a$ is C, $Y^a$ is C and $Z^a$ is N;
$X^a$ is N, $Y^a$ is N and $Z^a$ is C; and
$R^4$ is ethyl that is optionally substituted with one or more groups independently selected from F, Cl, and Br;

IV

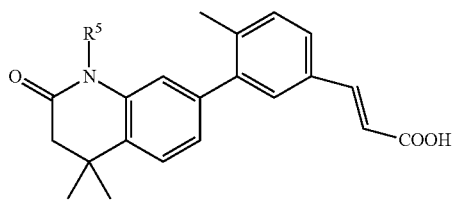

wherein:
$R^5$ is ethyl, propyl, or isopropyl; and

V

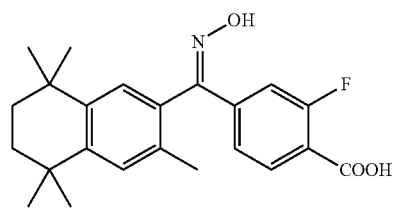

-continued

VI

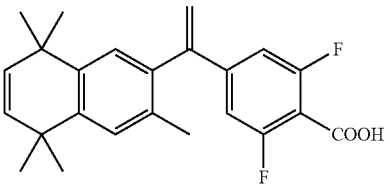

VII

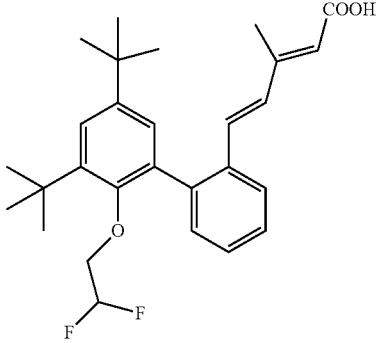

VIII

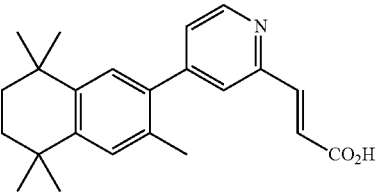

IX

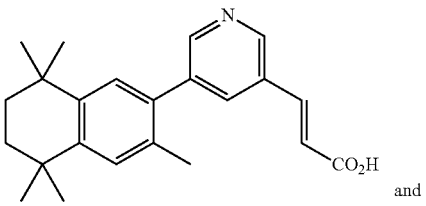

and

X

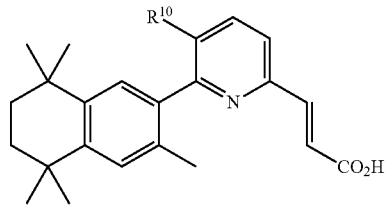

wherein:
$R^{10}$ is H or methyl;
and salts thereof;
provided the compound is not:

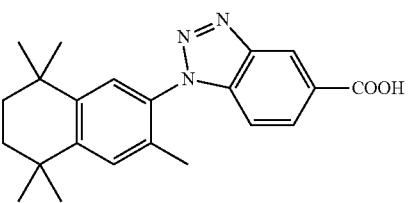

or

-continued

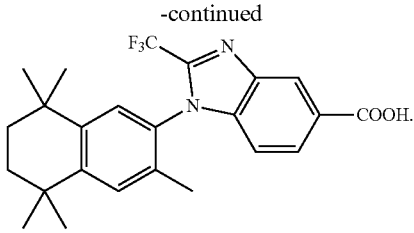

In one specific embodiment the compound of the invention is selected from:

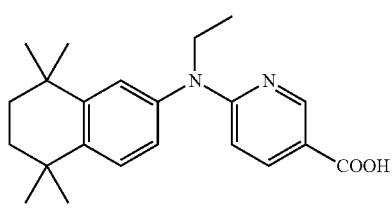

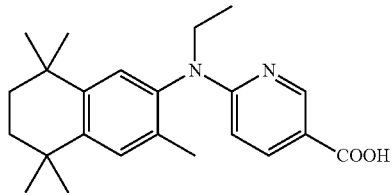

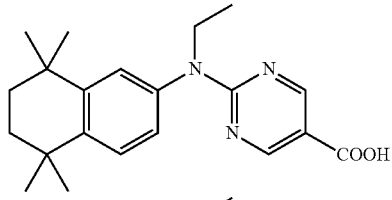

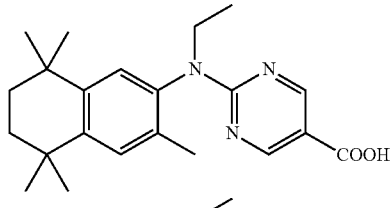

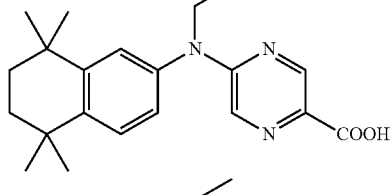

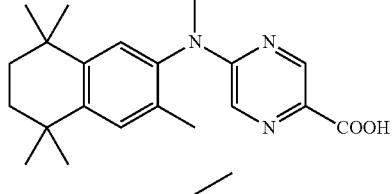

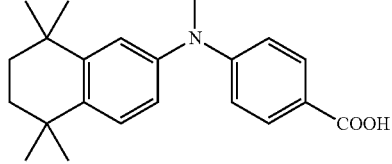

-continued

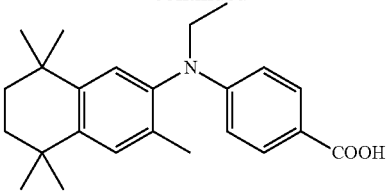

and and salts thereof.

Diseases and Condition

Compounds of the invention possessing RXR agonist properties are useful for treating Alzheimer's disease. The compounds of the invention may also treat Alzheimer's disease by targeting a combination of RXR:LXR controlled genes (like ApoE), or by binding to amyloid beta oligomers (where cholesterol usually binds) and disrupting calcium channel formation in neurons (Fantini, J. et al. *ACS Chem. Neurosci.* 2014, DOI: 10.1021/cn400183w).

Compounds of the invention are also useful for treating cancers, including but not limited to, colon, breast, lung, pancreatic, skin, cutaneous T-cell lymphoma, acute promyelocytic leukemia, ovarian, bladder, kidney, head and neck cancers, and Kaposi's sarcoma. See breast cancer: Esteva, F. J. et al. *JCO*, 2003, 21, 999-1006; advanced non-small lung cancer: (a) Khuri, F. R. et al. *JCO*, 2001, 19, 2626-2637 and (b) Lamph, W. W. et al. *Clin. Cancer Res.* 2004, 10, 8656-8664; pancreatic cancer: Liby, K. *Cancer Prev. Res.* 2010, 3, 1427-1434; and colon cancer: Cesario, R. M. et al. *Cancer Letters* 2006, 240, 225-233.

Compounds of the invention possessing RXR agonist properties and/or that target the Nurr1 receptor are useful for treating Parkinson's disease (see McFarland, K., et al, *ACS Chem. Neurosci.*, 2013, 4(11), 1430-1438), while compounds of the invention possessing RXR agonist properties and/or PPARg activity may be useful for treating diabetes (see Mukherjee, R. et al. *Nature*, 1997, 386, 407-410).

The compounds of the invention may also be useful for treating, psychotic disorders such as schizophrenia. Such treatment may also be carried out in combination with other antipsychotic treatments (see Lerner, V. et al. *Clin. Neuropharmacol.* 2008, 31, 25-33).

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames *Salmonella*/microsome mutagenicity assay." Mutat. Res. 2000, 455, 29-60.)

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form. In certain embodiments, the dose is about 300 mg/m$^2$/day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds can also be administered in combination with other therapeutic agents. In certain embodiments, compounds of the invention can be administered in combination with agents that are useful for the treatment of diseases associated with dopamine deficiency. For example, the compounds can be administered (and/or formulated) with clozapine, olanzapine, haloperidol, risperidone, perphenazine, quetiapine, or chlorpromazine.

The ability of a compound of the invention to act as an RXR agonist (e.g. to promote or activate RXR, i.e., promote or activate RXR regulated gene expression) may be determined using pharmacological models which are well known to the art, or using Test A or Test B described below.

Test A.

$EC_{50}$ values were determined from full dose-response curves ranging from $1\times10^{-9}$ to $0.3\times10^{-5}$M in transfected HCT-116 cells using an RXR mammalian two-hybrid system. HCT-116 cells were plated overnight at 80,000 cells/well in a 24 well plate and maintained as described above. The cells were co-transfected using a human RXR binding domain (BD) vector, a human RXR activation domain (AD) vector, a luciferase reporter gene containing BD-binding sites and *renilla* control plasmid. Transfection was achieved via 2 µL/well of Express-IN transfection reagent which was allowed to incubate for 24 hours with the cells. Then, the cells were treated with ethanol vehicle (0.1%) or analogs (1.0, 2.5, 5.0, 7.5, 10, 25, 50, 75, 100, 250, 500 nM, 1, 2, 3 µM) and incubated for 24 hours. The amount of rexinoid activity at each concentration was measured using the same luciferase assay described above, and $EC_{50}$ values were derived from dose-response curves of ligand concentration versus normalized luciferase activity. Data for the following representative compounds is provided in Table 1.

A42

A43

A44

A45
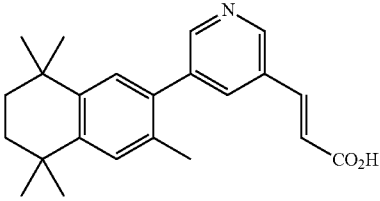

A46
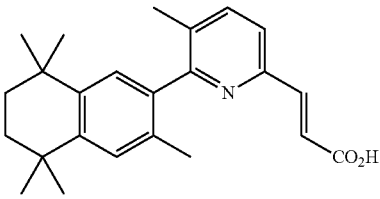

A47
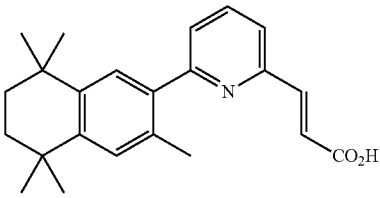

A48
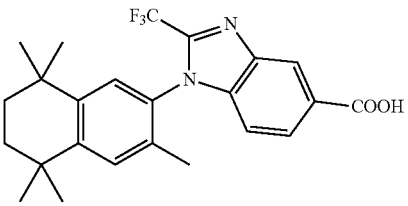

A49
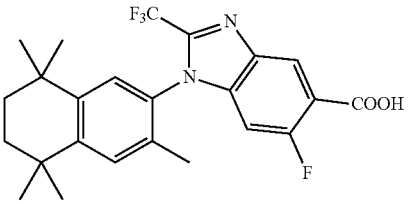

A50
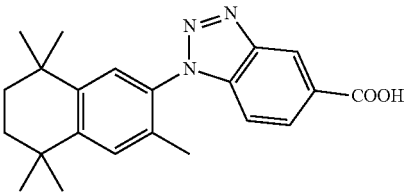

A51
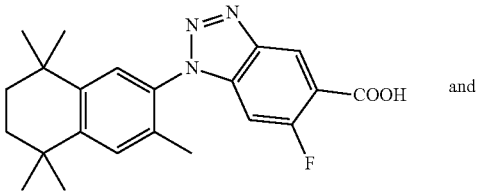

and

-continued

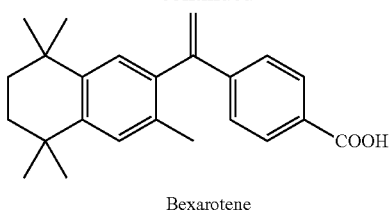

Bexarotene

TABLE 1

| Compound | EC$_{50}$ (nM) |
| --- | --- |
| Bexarotene | 23 |
| A42 | 3.7 |
| A43 | 21 |
| A44 | 38 |
| A45 | 710 |
| A46 | 305 |
| A47 | 1,030 |
| A48 | 20 |
| A49 | 220 |
| A50 | 270 |
| A51 | 1,400 |

Test B. RXR Agonist Assay (RXRE-Luciferase Based Assay).

Figure 2:
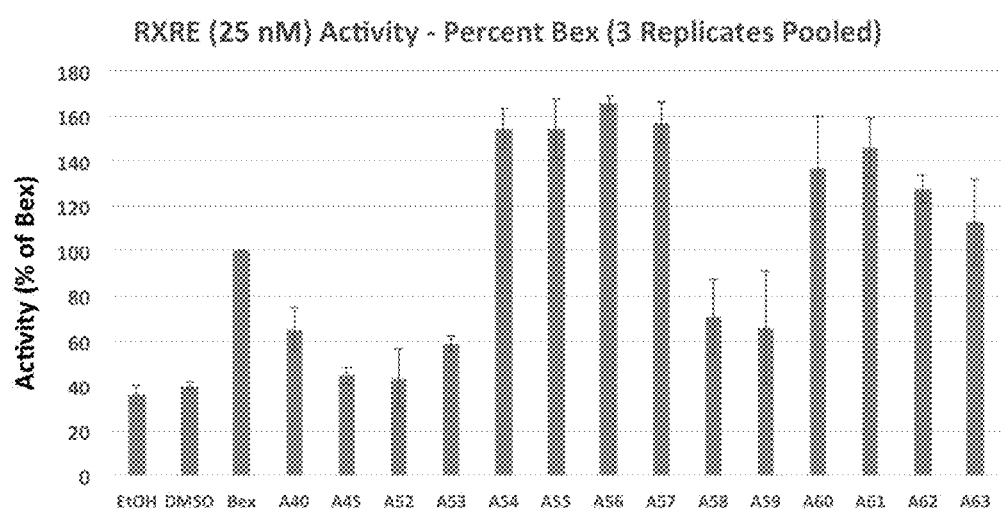
FIG. 2 Shows results from Test B for representative compounds of the invention. Analog dependent, RXR-mediated transcription, as measured by luciferase output, was compared to the parent compound Bexarotene (Bex) as a percentage.

An RXRE-luciferase assay of the compounds shown in FIG. 1 was run at 25 nM in HCT-116 cells. The cell line was transfected with hRXRα, an RXRE luciferase reporter gene, *renilla* control plasmid, and carrier DNA (pTZ18U). Cells were transfected for 7 hours utilizing a liposome-mediated transfection protocol then exposed to either the ethanol or DMSO vehicle or 25 nM Bexarotene or the indicated analog. After 24 hours the cells were lysed and a luciferase assay was completed. Analog dependent, RXR-mediated transcription, as measured by luciferase output, was compared to the parent compound Bexarotene (Bex) as a percentage. Data is provided in FIG. 2.

Test C. RXR Agonist Assay (RXRE-Luciferase Based Assay).

Compounds were tested for RXR agonist activity via an RXRE-luciferase based system utilizing human colon cancer cells HCT-116. The cell line was transfected with hRXRα, an RXRE luciferase reporter gene, *renilla* control plasmid, and carrier DNA (pTZ18U). Cells were transfected for 7 hours utilizing a liposome-mediated transfection protocol then exposed to either the ethanol or DMSO vehicle or 100 nM Bexarotene or the indicated analog. After 24 hours the cells were lysed and a luciferase assay was completed. Analog dependent, RXR-mediated transcription, as measured by luciferase output, was compared to the parent compound Bexarotene (Bex) as a percentage.

Figure 3:
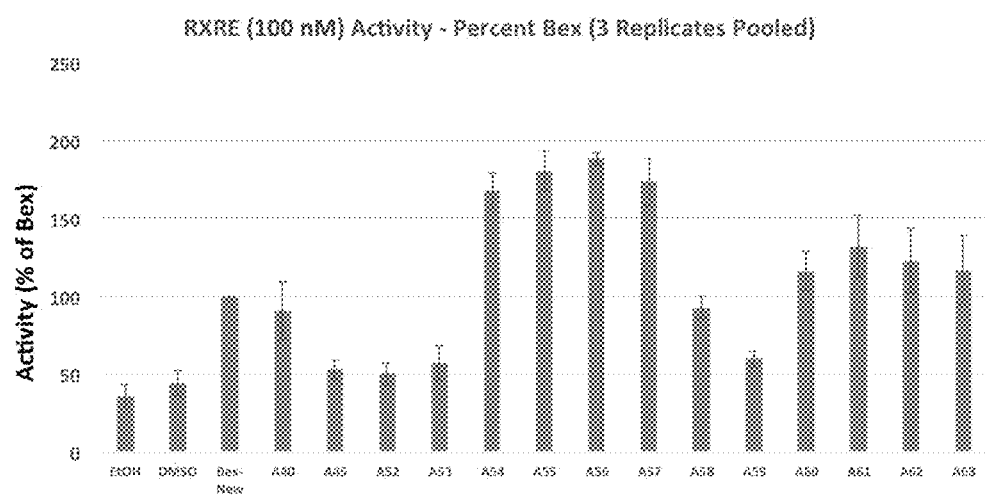
FIG. 3 Shows results from Test C for representative compounds of the invention. Analog dependent, RXR-mediated transcription, as measured by luciferase output, was compared to the parent compound Bexarotene (Bex) as a percentage.

Data is provided in FIG. 3.

Compounds evaluated in Tests A-C that are not prepared in the Examples below (e.g. compounds A42, A44, A48, and A50) were prepare using known techniques or using techniques similar to those described in the Examples.

The invention will now be illustrated by the following non-limiting Examples.

EXAMPLES

Example 1 Synthesis of 6-fluoro-1-(3,5,5,8,8-pentamethyl-5,6,7,8-tetrahydronaphthalen-2-yl)-1H-benzo[d][1,2,3]triazole-5-carboxylic acid (44) (A51)

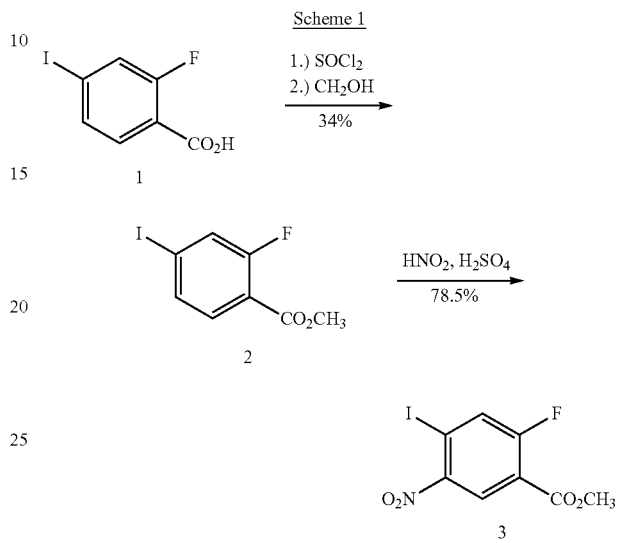

a. Methyl 2-fluoro-4-iodobenzoate (2)

A modified procedure of Kakuta and co-workers was followed.[2] 2-Fluoro-4-iodobenzoic acid (5.35 g, 20.1 mmol) was dissolved in methanol (30 mL, 741 mmol) was added thionyl chloride (2.6 mL, 35.8 mmol), dropwise at 0° C. with stirring. The reaction solution was then refluxed in an oil bath at 85° C. for 1 hr. Excess methanol was removed in vacuo, and benzene (20 mL) was added to the residue and then removed in vacuo. To the residue was added ethyl acetate (150 mL), and the organic layer was washed with saturated NaHCO$_3$ (200 mL) and brine (60 mL) and then dried over sodium sulfate, filtered and concentrated in vacuo. The crude product was purified by column chromatography (150 mL SiO$_2$, ethyl acetate:hexanes 1:48) to give 2 (5.3066 g, 94%) as a white crystalline solid, m.p. 76-78° C.: $^1$H NMR (400 MHz, CDCl$_3$) δ 7.63 (t, J=8.0, 1H), 7.56 (dd, J=8.4, 1.6, 1H), 7.53 (dd, J=10.0, 1.2, 1H), 3.92 (s, 3H); $^{13}$C NMR (100.6 MHz, CDCl$_3$) δ 164.4, 164.3, 162.3, 159.7, 133.5, 133.4, 133.0, 126.5, 126.3, 118.2, 118.1, 99.8, 99.7, 52.5; IR (neat) n 2952, 1700, 1595, 1561 cm$^{-1}$; LC-FAB-MS (M)+ calcd for C$_8$H$_6$FIO$_2$ 279.9397, found 279.9394.

b. Methyl 2-fluoro-4-iodo-5-nitrobenzoate (3)

A modified procedure of Kakuta and co-workers was followed.[2] To a solution of methyl 2-fluoro-4-iodobenzoate (2) (1.4 g, 5.0 mmol) dissolved in concentrated sulfuric acid (5 mL) was added a solution of concentrated nitric acid (6.0 mL) and concentrated sulfuric acid (9.0 mL) dropwise at 0° C. with stirring. The reaction solution was then stirred at room temperature for 5 h. The reaction solution was poured onto ice (100 mL) and extracted with ethyl acetate. The combined organic layers were washed with saturated NaHCO$_3$ (100 mL) and brine (50 mL) and then dried over sodium sulfate, filtered and concentrated in vacuo. The crude product was purified by column chromatography (150 mL $SiO_2$, 2% ethyl acetate:hexanes to 10% ethyl acetate:hexanes) to give 3 (1.27 g, 78%) as a green crystalline solid, m.p. 84-87° C.: $^1$H NMR (400 MHz, $CDCl_3$) δ 8.50 (d, J=6.4, 1H), 7.87 (d, J=9.6, 1H), 3.97 (s, 3H); $^{13}$C NMR (100.6 MHz, $CDCl_3$) δ 163.1, 162.3, 162.2, 160.4, 148.7, 131.1, 130.8, 129.1, 129.0, 119.4, 119.2, 92.7, 92.6, 53.1; IR (neat) n 2987, 1703, 1602, 1560, 1532, 1440 cm$^{-1}$; LC-FAB-MS (M)+ calcd for $C_8H_5FINO_4$ 324.9247, found 324.9249.

mL) was passed through a 10% Pd/C cartridge at 1.0 mL/minute, twice, in the ThalesNano H-cube® at 70° C. and 2-5 bar pressure. The resulting solution was concentrated in vacuo to give 6 (2.13 g, 97%) as a yellow, crystalline solid, m.p. 76-89° C.: $^1$H NMR (400 MHz, $CDCl_3$) δ 7.00 (s, 1H), 6.63 (s, 1H), 3.34 (br s, 2H), 2.15 (s, 3H), 1.63 (s, 4H), 1.26 (s, 12H); $^{13}$C NMR (100.6 MHz, $CDCl_3$) δ 143.5, 142.0, 135.2, 128.3, 120.5, 112.6, 35.3, 35.2, 33.8, 33.4, 32.0, 31.8, 17.1; IR (neat) n 3404, 3335, 2956, 2925, 1626, 1504 cm$^{-1}$; LC-MS-CI (M+H)+ calcd for $C_{15}H_{24}N$ 218.1909, found 218.1908.

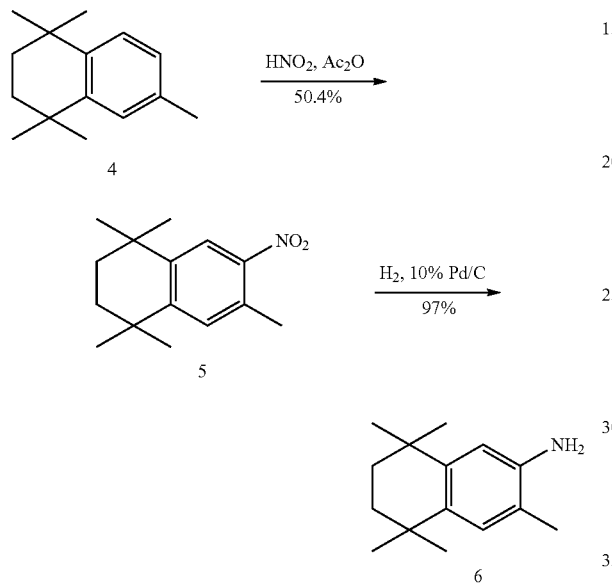

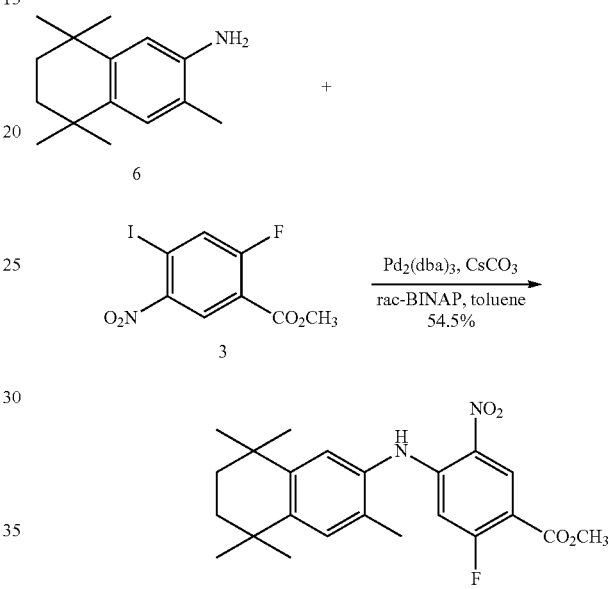

c. 1,1,4,4,6-pentamethyl-7-nitro-1,2,3,4-tetrahydronaphthalene (5)

The method of Kakuta and co-workers was followed.[7] To a solution of 1,1,4,4,6-pentamethyl-1,2,3,4-tetrahydronaphthalene (4) (2.0 g, 9.9 mmol) in acetic anhydride (10 mL) cooled to 0° C. was added concentrated nitric acid (0.80 mL), dropwise. A precipitate quickly formed (2 min.) and the heterogeneous solution was poured onto ice and then extracted with ethyl acetate. The combined organic layers were washed with brine and then dried over sodium sulfate, filtered and concentrated in vacuo to give a crude residue. This residue was dissolved in hot ethyl acetate (4.0 mL) and hexanes (6.0 mL) was added and the solution was cooled in an ice bath and the resulting precipitate was filtered to give 5 (1.23 g, 50%) as a white crystalline solid, m.p. 148-150° C.: $^1$H NMR (400 MHz, $CDCl_3$) δ 7.96 (s, 1H), 7.21 (s, 1H), 2.56 (s, 3H), 1.69 (s, 4H), 1.29 (s, 12H); $^{13}$C NMR (100.6 MHz, $CDCl_3$) δ 151.1, 146.8, 144.3, 130.9, 130.4, 123.1, 34.6, 34.5, 34.5, 34.2, 31.6, 31.5, 20.5; IR (neat) n 2960, 2924, 1515, 1347 cm$^{-1}$; LC-MS-CI (M+$NH_4$)+ calcd for $C_{15}H_{25}N_2O_2$ 265.1916, found 265.1927.

d. 3,5,5,8,8-Pentamethyl-5,6,7,8-tetrahydronaphthalen-2-amine (6)

Compound 6 was synthesized as follows. A 0.05 M solution of 1,1,4,4,6-pentamethyl-7-nitro-1,2,3,4-tetrahydronaphthalene (5) (2.5 g, 10.1 mmol) in ethyl acetate (205 e. Methyl 2-fluoro-5-nitro-4-((3,5,5,8,8-pentamethyl-5,6,7,8-tetrahydronaphthalen-2-yl)amino)benzoate (7)

To a solution of 3,5,5,8,8-pentamethyl-5,6,7,8-tetrahydronaphthalen-2-amine (6) (0.83 g, 3.82 mmols) and Methyl 2-fluoro-4-iodo-5-nitrobenzoate (3) (1.28 g, 3.93 mmols) in anhydrous toluene (4.0 mL) was added $Cs_2CO_3$ (3.11 g, 9.5 mmols), rac-BINAP (0.18 g, 0.28 mmols), and $Pd_2(dba)_3$ (0.17 g, 0.19 mmols). The reaction solution was heated to reflux in an oil bath at 125° C. under a nitrogen atmosphere for 22 h and then filtered. The filtrate was concentrated in vacuo and the crude residue was purified by column chromatography (150 mL $SiO_2$, 2% ethyl acetate:hexanes) to give 7 (0.87 g, 54%) as a yellow crystalline solid, m.p. 166-169° C.: $^1$H NMR (400 MHz, $CDCl_3$) δ 9.60 (br s, 1H), 8.95 (d, J=7.6, 1H), 7.25 (s, 1H), 7.14 (s, 1H), 6.43 (d, J=13.2, 1H), 3.90 (s, 3H), 2.18 (s, 3H), 1.70 (s, 4H), 1.31 (s, 6H), 1.25 (s, 6H); $^{13}$C NMR (100.6 MHz, $CDCl_3$) δ 167.2, 164.6, 162.9, 162.9, 148.6, 148.4, 145.0, 144.6, 133.3, 133.2, 132.7, 131.3, 129.6, 128.5, 124.5, 107.9, 107.7, 102.2, 101.9, 52.2, 34.9, 34.7, 34.1, 34.0, 31.8, 31.7, 17.4; IR (neat) n 3342, 2968, 1709, 1637, 1565, 1526 cm$^{-1}$; LC-ES-MS (M)+ calcd for $C_{23}H_{27}FN_2O_4Na$ 437.1852, found 437.1853.

Scheme 4

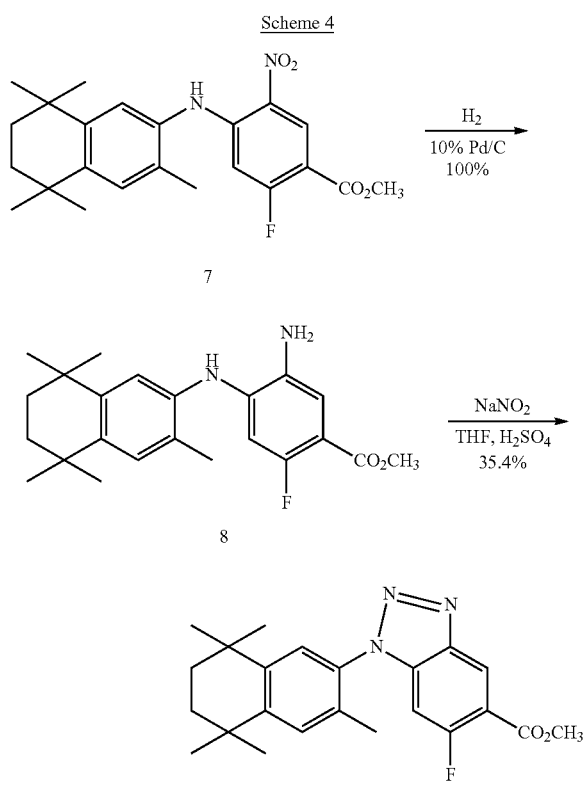

f. Methyl 5-amino-2-fluoro-4-((3,5,5,8,8-pentamethyl-5,6,7,8-tetrahydronaphthalen-2-yl)amino)benzoate (8)

A 0.05 M solution of methyl 2-fluoro-5-nitro-4-((3,5,5,8,8-pentamethyl-5,6,7,8-tetrahydronaphthalen-2-yl)amino)benzoate (7) (1.25 g, 3.02 mmol) in ethyl acetate (65 mL) was passed through a 10% Pd/C cartridge at 1.0 mL/minute, twice, in the ThalesNano H-cube® at 70° C. and 2-5 bar pressure. The resulting solution was concentrated in vacuo to give 8 (1.16 g, 100%) as a yellow, crystalline solid, m.p. 221-225° C.: $^1$H NMR (400 MHz, CDCl$_3$) δ 7.37 (d, J=7.2, 1H), 7.16 (s, 1H), 7.06 (s, 1H), 6.41 (d, J=12.8, 1H), 5.75 (br s, 1H), 3.87 (s, 3H), 3.28 (br s, 2H), 2.16 (s, 3H), 1.68 (s, 4H), 1.29 (s, 6H), 1.24 (s, 6H); $^{13}$C NMR (100.6 MHz, CDCl$_3$) δ 165.3, 165.2, 159.9, 157.4, 143.9, 142.3, 142.2, 141.5, 135.9, 129.2, 129.0, 129.0, 128.4, 120.9, 120.3, 120.2, 107.3, 107.2, 101.4, 101.1, 51.8, 35.1, 34.9, 34.0, 33.8, 31.9, 31.8, 17.4; IR (neat) ν 3410, 3388, 3313, 2943, 1689, 1604, 1526, 1502 cm$^{-1}$; LC-ES-MS (M+H)+ calcd for C$_{23}$H$_{29}$FN$_2$O$_2$Na 407.2111, found 407.2115.

g. Methyl 6-fluoro-1-(3,5,5,8,8-pentamethyl-5,6,7,8-tetrahydronaphthalen-2-yl)-1H-benzo[d][1,2,3]triazole-5-carboxylate (9)

To a solution of methyl 5-amino-2-fluoro-4-((3,5,5,8,8-pentamethyl-5,6,7,8-tetrahydronaphthalen-2-yl)amino)benzoate (8) (1.14 g, 2.96 mmols) in THF (14.0 mL) was added a solution of concentrated sulfuric acid (7.0 mL) and water (70.0 mL) followed by a solution of NaNO$_2$ (0.294 g, 4.26 mmols) in water (14.0 mL). The reaction solution was stirred at 0° C. for 30 min. and then gently warmed to 55° C. for 15 min. The reaction was extracted with ethyl acetate. The combined organic layers were washed with water and brine and then dried over sodium sulfate, filtered and concentrated in vacuo to give a crude product that was purified by column chromatography (150 mL SiO$_2$, 2.5% ethyl acetate:hexanes to 10% ethyl acetate:hexanes) to give 9 (1.12 g, 95%) as a crystalline solid, m.p. 152-154° C.: $^1$H NMR (400 MHz, CDCl$_3$) δ 8.78 (d, J=6.0, 1H), 7.34 (s, 1H), 7.09 (d, J=9.6, 1H), 3.99 (s, 3H), 2.05 (s, 3H), 1.73 (s, 4H), 1.34 (s, 6H), 1.28 (s, 6H); $^{13}$C NMR (100.6 MHz, CDCl$_3$) δ 164.3, 164.2, 162.5, 160.0, 147.6, 144.4, 141.4, 136.0, 135.9, 131.9, 131.3, 129.8, 125.2, 125.1, 124.5, 117.0, 116.9, 97.5, 97.2, 52.6, 34.8, 34.6, 34.3, 34.2, 31.8, 31.7, 17.3; IR (neat) n 2967, 1709, 1630, 1510 cm$^{-1}$; LC-ES-MS (M)+ calcd for C$_{23}$H$_{26}$FN$_3$O$_2$Na 418.1907, found 418.1901.

Scheme 5

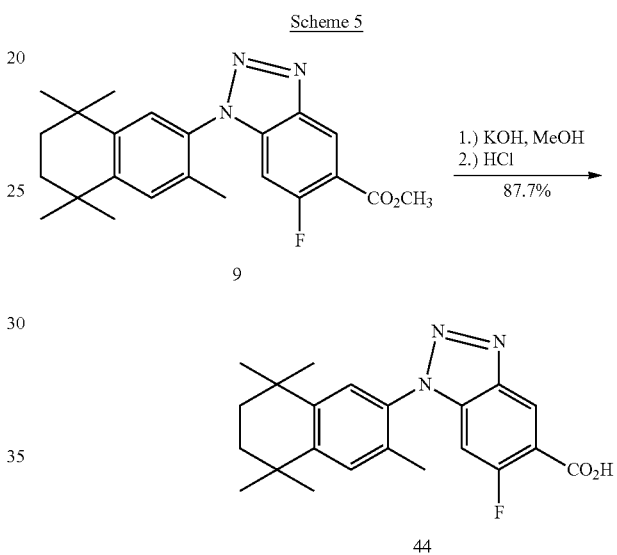

h. 6-Fluoro-1-(3,5,5,8,8-pentamethyl-5,6,7,8-tetrahydronaphthalen-2-yl)-1H-benzo[d][1,2,3]triazole-5-carboxylic acid (44)

To a round bottom flask containing methyl 6-fluoro-1-(3,5,5,8,8-pentamethyl-5,6,7,8-tetrahydronaphthalen-2-yl)-1H-benzo[d][1,2,3]triazole-5-carboxylate (9) (0.80 g, 2.0 mmols) in methanol (5.0 mL) was added a solution of KOH (0.39 g, 6.95 mmol) in water (0.58 mL), and the reaction solution was refluxed for 1.5 h. After cooling the solution to room temperature, the addition of 20% HCl (80 mL) effected the precipitation of crude product (0.75 g, 96%), and this crude product was purified by column chromatography (25 mL SiO$_2$, ethyl acetate to 4% methanol:ethyl acetate) to give 44 (0.68 g, 87%) as a crystalline solid, m.p. 190-197° C.: $^1$H NMR (400 MHz, CDCl$_3$) δ 9.99 (br s, 1H), 8.96 (d, J=6.4, 1H), 7.36 (s, 1H), 7.28 (s, 1H), 7.13 (d, J=9.6, 1H), 2.07 (s, 3H), 1.74 (s, 4H), 1.35 (s, 6H), 1.29 (s, 6H); $^{13}$C NMR (100.6 MHz, CDCl$_3$) δ 168.9, 168.8, 163.0, 160.4, 147.7, 144.5, 141.3, 136.6, 136.5, 131.8, 131.3, 129.8, 126.2, 124.5, 116.0, 115.9, 97.8, 97.5, 34.8, 34.6, 34.3, 34.2, 31.8, 31.7, 17.3; IR (neat) n 2960, 1727, 1708, 1684, 1626, 1491, 1454 cm$^{-1}$; LC-ES-MS (M-H)– calcd for C$_{22}$H$_{23}$FN$_3$O$_2$ 380.1774, found 380.20.

Example 2 Synthesis of 6-fluoro-1-(3,5,5,8,8-pentamethyl-5,6,7,8-tetrahydronaphthalen-2-yl)-2-(trifluoromethyl)-1H-benzo[d]imidazole-5-carboxylic acid (49) (A49)

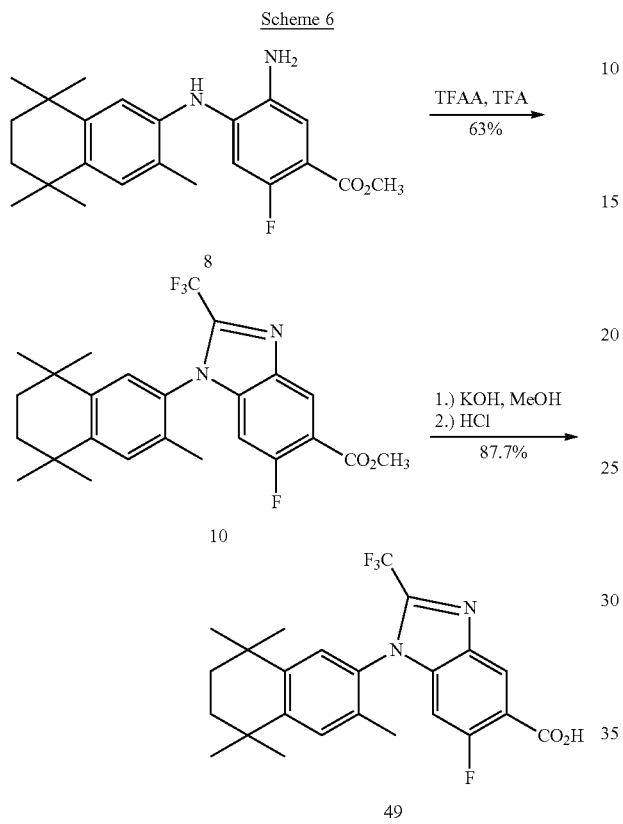

a. Methyl 6-fluoro-1-(3,5,5,8,8-pentamethyl-5,6,7,8-tetrahydronaphthalen-2-yl)-2-(trifluoromethyl)-1H-benzo[d]imidazole-5-carboxylate (10)

To a flask containing methyl 2-fluoro-5-nitro-4-(3,5,5,8,8-pentamethyl-5,6,7,8-tetrahydronaphthalen-2-yl)amino)benzoate (7) was added TFA (12.0 mL) and trifluoroacetic anhydride (2.4 mL, 16.8 mmol) and stirred for 1 h. TLC showed little progress, so an additional portion of trifluoroacetic anhydride (2.4 mL, 16.8 mmol) was added and the reaction was heated to 57° C. with stirring for 1 h. TLC indicated the reaction had progressed, and an additional portion of trifluoroacetic anhydride (2.0 mL, 14.0 mmol) was added and the reaction was allowed to stir for another 1 h. The reaction was allowed to cool to room temperature and then slowly poured into saturated NaHCO₃ (100 mL) and extracted with ethyl acetate. The combined organic layers were washed with water (50 mL) and then brine (50 mL), dried over sodium sulfate, filtered, and concentrate in vacuo to give a crude residue that was purified by column chromatography (150 mL SiO$_2$, 2.6% ethyl acetate:hexanes to 2.8% ethyl acetate:hexanes) to give 10 (Scheme 16) (1.15 g, 83%) as a crystalline solid, m.p. 122-125° C.: $^1$H NMR (400 MHz, CDCl$_3$) δ 8.54 (d, J=6.4, 1H), 7.28 (s, 1H), 7.17 (s, 1H), 6.80 (d, J=10.0, 1H), 3.96 (s, 3H), 1.88 (s, 3H), 1.72 (s, 4H), 1.33 (s, 6H), 1.24 (s, 3H), 1.23 (s, 3H); $^{13}$C NMR (100.6 MHz, CDCl$_3$) δ 164.7, 164.6, 161.6, 159.1, 147.8, 144.6, 143.6, 143.2, 143.2, 139.7, 139.6, 136.3, 132.0, 129.6, 129.3, 126.2, 125.9, 125.9, 119.6, 116.9, 116.1, 116.0, 99.2, 98.9, 52.4, 34.8, 34.6, 34.3, 34.1, 31.8, 31.7, 31.6, 31.6, 16.6; IR (neat) n 2960, 1731, 1632, 1533, 1501 cm$^{-1}$; LC-ES-MS (M+Na)+ calcd for C$_{25}$H$_{26}$F$_4$N$_2$O$_2$Na 485.1828, found 485.1828.

b. 6-Fluoro-1-(3,5,5,8,8-pentamethyl-5,6,7,8-tetrahydronaphthalen-2-yl)-2-(trifluoromethyl)-1H-benzo[d]imidazole-5-carboxylic acid (49)

To a round bottom flask containing methyl 6-fluoro-1-(3,5,5,8,8-pentamethyl-5,6,7,8-tetrahydronaphthalen-2-yl)-2-(trifluoromethyl)-1H-benzo[d]imidazole-5-carboxylate (10) (1.02 g, 2.27 mmols) in methanol (5.3 mL) was added a solution of KOH (0.40 g, 7.13 mmol) in water (0.50 mL), and the reaction solution was refluxed for 1.5 h. After cooling the solution to room temperature, the addition of 20% HCl (80 mL) effected the precipitation of crude product, and this crude product was purified by column chromatography (25 mL SiO$_2$, 40% ethyl acetate:hexanes to ethyl acetate) to give 49 (0.62 g, 62%) as a crystalline solid, m.p. 219-220° C.: $^1$H NMR (400 MHz, CDCl$_3$) δ 9.57 (br s, 1H), 8.71 (d, J=6.4, 1H), 7.30 (s, 1H), 7.19 (s, 1H), 6.85 (d, J=10.0, 1H), 1.91 (s, 3H), 1.73 (s, 4H), 1.34 (s, 6H), 1.25 (s, 3H), 1.24 (s, 3H); $^{13}$C NMR (100.6 MHz, CDCl$_3$) δ 169.3, 169.2, 162.2, 159.6, 147.9, 144.7, 144.2, 143.9, 143.8, 143.5, 143.4, 143.1, 140.5, 140.3, 136.3, 132.0, 129.5, 129.4, 126.8, 126.2, 122.3, 119.5, 116.8, 115.1, 115.0, 114.1, 99.4, 99.1, 34.8, 34.6, 34.3, 34.1, 31.8, 31.7, 31.7, 31.6, 16.6; IR (neat) n 2962, 1681, 1629, 1536, 1423 cm$^{-1}$; LC-ES-MS (M–H)– calcd for C$_{24}$H$_{23}$F$_4$N$_2$O$_2$ 447.1696, found 447.1709.

Example 3 Synthesis of (E)-3-(4-(3,5,5,8,8-pentamethyl-5,6,7,8-tetrahydronaphthalen-2-yl)pyridin-2-yl)acrylic acid (69) (A43)

4-Bromopicolinaldehyde (66) was converted to (E)-ethyl 3-(4-bromopyridin-2-yl)acrylate (67) in 96% yield by a Horner-Wadsworth-Emmons reaction (Scheme 7).

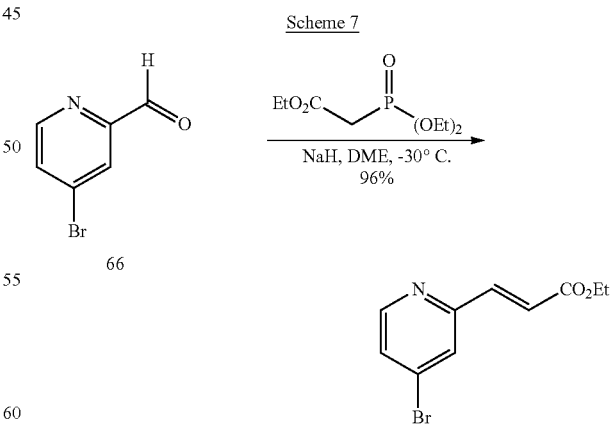

The acrylate 67 is then reacted with the boronic acid 82 to give (E)-ethyl 3-(4-(3,5,5,8,8-pentamethyl-5,6,7,8-tetrahydronaphthalen-2-yl)pyridin-2-yl)acrylate (68) in 92% yield which is saponified to (E)-3-(4-(3,5,5,8,8-pentamethyl-5,6,7,8-tetrahydronaphthalen-2-yl)pyridin-2-yl)acrylic acid (69) in 74% yield (Scheme 8).

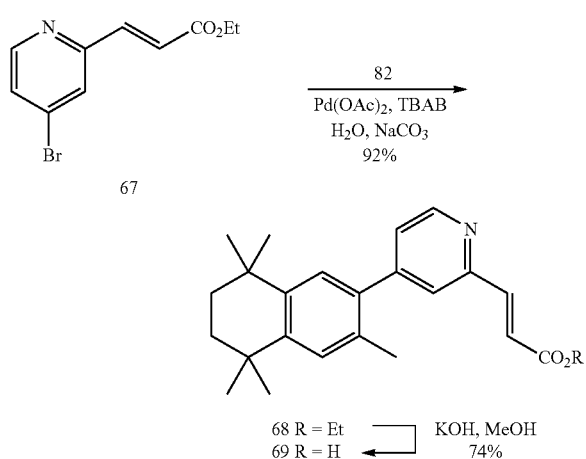

a. (E)-Ethyl 3-(4-bromopyridin-2-yl)acrylate (67)

To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 4-bromopicolinaldehyde (66) (1.24 g, 6.67 mmol) in DME (3 mL), and the reaction was stirred at −30° C. for 1.5 h and then poured into water (50 mL) and extracted with ethyl acetate. The combined organic layers were washed with an aqueous saturated $NH_4Cl$ solution and then brine, dried over sodium sulfate, filtered and concentrated in vacuo to give a crude product that was purified by column chromatography (150 mL $SiO_2$, 5% ethyl acetate:hexanes) to give 67 (1.647 g, 96%) as a colorless crystalline solid, m.p. 70-72° C.: $^1$H NMR (400 MHz, $CDCl_3$) δ 8.43 (d, J=5.2, 1H), 7.58 (d, J=15.6, 1H), 7.57 (d, J=1.6, 1H), 7.42 (dd, J=5.2, 1.6, 1H), 6.91 (d, J=15.6, 1H), 4.26 (q, J=7.2, 2H), 1.32 (t, J=7.2, 3H); $^{13}$C NMR (100.6 MHz, $CDCl_3$) δ 166.2, 154.3, 150.6, 141.7, 133.3, 127.2, 127.1, 123.9, 60.7, 14.2; IR (neat) δ 2987, 1712, 1646, 1563, 1537 cm$^{-1}$; LC-FAB-MS (M+H)+ calcd for $C_{10}H_{11}BrNO_2$ 255.9973, found 255.9963.

b. (E)-Ethyl 3-(4-(3,5,5,8,8-pentamethyl-5,6,7,8-tetrahydronaphthalen-2-yl)pyridin-2-yl)acrylate (68)

To a 50 mL Schlenk flask charged with bromide 67 (0.4125 g, 1.61 mmol), boronic acid 82 (0.411 g, 1.67 mmol), TBAB (0.52 g), $Na_2CO_3$ (0.51 g, 4.81 mmol), and water (3.7 mL), was added $Pd(OAc)_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL $SiO_2$, 5% ethyl acetate:hexanes) to give 68 (0.56 g, 92%) as a white solid: $^1$H NMR (400 MHz, $CDCl_3$) δ 8.65 (d, J=5.2, 1H), 7.73 (d, J=16.0, 1H), 7.41 (d, J=0.8, 1H), 7.27 (dd, J=5.2, 1.6, 1H), 7.22, (s, 1H), 7.14 (s, 1H), 6.97 (d, J=16.0, 1H), 4.28 (q, J=6.8, 2H), 2.25 (s, 3H), 1.71 (s, 4H), 1.34 (t, J=7.2, 3H), 1.32 (s, 6H), 1.29 (s, 6H); $^{13}$C NMR (100.6 MHz, $CDCl_3$) δ 166.7, 152.5, 151.2, 149.5, 145.6, 143.1, 143.0, 135.8, 131.8, 128.8, 127.4, 124.9, 124.8, 122.6, 60.6, 34.9, 34.0, 33.9, 31.8, 31.7, 19.9, 14.2; IR (neat) δ 2970, 1694, 1593 cm$^{-1}$; LC-FAB-MS (M+Na)+ calcd for $C_{25}H_{31}NO_2Na$ 400.2253, found 400.2237.

c. (E)-3-(4-(3,5,5,8,8-Pentamethyl-5,6,7,8-tetrahydronaphthalen-2-yl)pyridin-2-yl)acrylic acid (69)

To a 100 mL round bottom flask containing 68 (1.0417 g, 2.76 mmol) suspended in methanol (6.0 mL) was added a solution of KOH (0.4767 g, 8.50 mmol) in water (0.60 mL), and the solution was refluxed in an oil-bath pre-heated to 85° C. for 1 h. The reaction was allowed to cool to room temperature, and acidified with an aqueous 20% HCl solution (50 mL). The resulting precipitate was filtered and washed with copious amounts of water, and the crude white powder that appeared to be pure by TLC (single spot) 69 (0.9166 g, 95%) as a white crystalline solid that was purified by column chromatography (25 mL $SiO_2$, 1% methanol:ethyl acetate) to give 69 (0.708 g, 74%) as a crystalline solid, m.p. 205-208° C.: $^1$H NMR (400 MHz, $CDCl_3$) δ 8.90 (d, J=5.6, 1H), 7.97 (d, J=16.0, 1H), 7.87 (s, 1H), 7.77 (d, J=5.2, 1H), 7.35 (d, J=16.4, 1H), 7.27 (s, 1H), 7.21 (s, 1H), 2.32 (s, 3H), 1.70 (s, 4H), 1.31 (s, 6H), 1.29 (s, 6H); $^{13}$C NMR (100.6 MHz, $CDCl_3$) δ 166.4, 159.6, 148.2, 147.4, 144.0, 142.4, 134.5, 133.2, 131.9, 130.0, 129.7, 127.7, 126.5, 126.0, 34.8, 34.7, 34.2, 34.0, 31.8, 31.6, 20.0; IR (neat) δ 2970, 1711, 1603 cm$^{-1}$; LC-FAB-MS (M+H)+ calcd for $C_{23}H_{28}NO_2$ 348.1964, found 348.1953.

Example 4 Synthesis of (E)-3-(5-(3,5,5,8,8-pentamethyl-5,6,7,8-tetrahydronaphthalen-2-yl)pyridin-3-yl)acrylic acid (73) (A45)

Using a procedure similar to that described in Example 3, 5-bromonicotinaldehyde (70) was converted to (E)-ethyl 3-(5-bromopyridin-3-yl)acrylate (71) in 93% yield by a Horner-Wadsworth-Emmons reaction (Scheme 9).

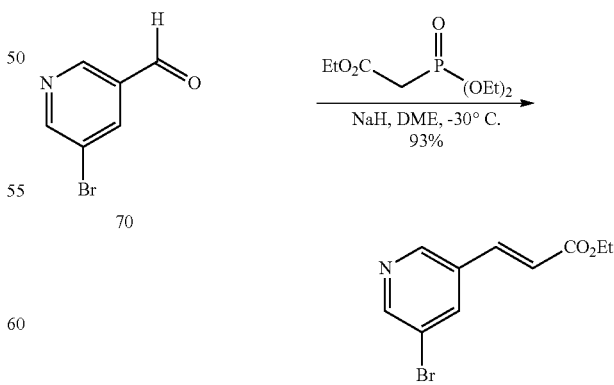

The acrylate 71 is reacted with the boronic acid 82 to give (E)-ethyl 3-(5-(3,5,5,8,8-pentamethyl-5,6,7,8-tetrahydronaphthalen-2-yl)pyridin-3-yl)acrylate (72) in 88% yield which is saponified to (E)-3-(5-(3,5,5,8,8-pentamethyl-5,6,7,8-tetrahydronaphthalen-2-yl)pyridin-3-yl)acrylic acid (73) in 50% yield (Scheme 10).

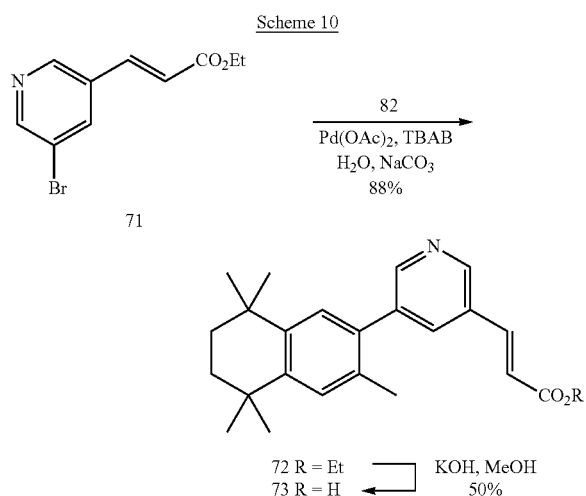

a. (E)-Ethyl 3-(5-bromopyridin-3-yl)acrylate (71)

To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 5-bromonicotinaldehyde (70) (1.24 g, 6.67 mmol) in DME (3 mL), and the reaction was stirred at −30° C. for 1.5 h and then poured into water (50 mL) and extracted with ethyl acetate. The combined organic layers were washed with an aqueous saturated $NH_4Cl$ solution and then brine, dried over sodium sulfate, filtered and concentrated in vacuo to give a crude product that was purified by column chromatography (150 mL $SiO_2$, 7% ethyl acetate:hexanes to 10% ethyl acetate:hexanes) to give 71 (1.587 g, 93%) as a colorless crystalline solid, m.p. 80-82° C.: $^1$H NMR (400 MHz, $CDCl_3$) δ 8.65 (d, J=2.0, 1H), 8.64 (d, J=1.6, 1H), 7.99 (dd, J=2.0, 1.6, 1H), 7.59 (d, J=16.0, 1H), 6.50 (d, J=16.0, 1H), 4.27 (q, J=7.2, 2H), 1.33 (t, J=7.2, 3H); $^{13}$C NMR (100.6 MHz, $CDCl_3$) δ 165.77, 151.42, 147.2, 138.9, 136.8, 131.9, 122.1, 121.1, 60.9, 14.2; IR (neat) δ 2983, 1713, 1640 cm$^{-1}$; LC-FAB-MS (M+H)+ calcd for $C_{10}H_{11}BrNO_2$ 255.9973, found 255.9966.

b. (E)-Ethyl 3-(5-(3,5,5,8,8-pentamethyl-5,6,7,8-tetrahydronaphthalen-2-yl)pyridin-3-yl)acrylate (72)

To a 50 mL Schlenk flask charged with bromide 71 (0.434 g, 1.61 mmol), boronic acid 82 (0.409 g, 1.66 mmol), TBAB (0.52 g), $Na_2CO_3$ (0.51 g, 4.81 mmol), and water (3.7 mL), was added $Pd(OAc)_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL $SiO_2$, 6% ethyl acetate:hexanes to 8% ethyl acetate:hexanes) to give 72 (0.5358 g, 88%) as a white solid, m.p. 114-119° C.: $^1$H NMR (400 MHz, $CDCl_3$) δ 8.71 (d, J=2.0, 1H), 8.60 (d, J=2.0, 1H), 7.85 (t, J=2.0, 1H), 7.72 (d, J=16.4, 1H), 7.23 (s, 1H), 7.13 (s, 1H), 6.54 (d, J=16.4, 1H), 4.25 (q, J=7.2, 2H), 2.24 (s, 3H), 1.71 (s, 4H), 1.35 (t, J=7.2, 3H), 1.33 (s, 6H), 1.29 (s, 6H); $^{13}$C NMR (100.6 MHz, $CDCl_3$) δ 166.1, 150.2, 146.6, 145.4, 143.1, 140.5, 138.2, 135.4, 134.1, 132.2, 129.9, 128.7, 127.9, 120.9, 60.8, 34.9, 34.0, 33.9, 31.8, 31.7, 20.0, 14.2; IR (neat) δ 2956, 1709, 1644 cm$^{-1}$; LC-FAB-MS (M+H)+ calcd for $C_{25}H_{32}NO_2$ 378.2433, found 378.2441.

c. (E)-3-(5-(3,5,5,8,8-Pentamethyl-5,6,7,8-tetrahydronaphthalen-2-yl)pyridin-3-yl)acrylic acid (73)

To a 100 mL round bottom flask containing 72 (0.662 g, 1.89 mmol) suspended in methanol (5.0 mL) was added a solution of KOH (0.3013 g, 5.37 mmol) in water (0.38 mL), and the solution was refluxed in an oil-bath pre-heated to 85° C. for 1 h. The reaction was allowed to cool to room temperature, and acidified with an aqueous 20% HCl solution (50 mL). The resulting precipitate was filtered and washed with copious amounts of water, and the crude white powder that was purified by column chromatography (25 mL $SiO_2$, 1% methanol:ethyl acetate) to give 72 (0.3072 g, 50%) as a solid, m.p. 165-168° C.: $^1$H NMR (400 MHz, $CDCl_3$) δ 8.95-7.88 (m, 5H), 7.13 (s, 1H), 6.74-6.66 (m, 1H), 2.28 (s, 3H), 1.78 (s, 4H), 1.30 (s, 12H); $^{13}$C NMR (100.6 MHz, $CDCl_3$) δ 169.7, 149.2, 145.9, 143.3, 141.4, 139.5, 137.3, 133.4, 132.3, 131.2, 130.9, 128.9, 128.3, 122.1, 34.9, 34.9, 34.0, 33.9, 32.0, 31.7, 20.4; IR (neat) δ 2958, 1700, 1643 cm$^{-1}$; LC-FAB-MS (M−H)− calcd for $C_{23}H_{26}NO_2$ 348.1964, found 348.1961.

Example 5 Synthesis of (E)-3-(5-methyl-6-(3,5,5,8,8-pentamethyl-5,6,7,8-tetrahydronaphthalen-2-yl)pyridin-2-yl)acrylic acid (77) (A46)

6-Bromo-5-methylpicolinaldehyde (74) was converted to (E)-ethyl 3-(6-bromo-5-methylpyridin-2-yl)acrylate (75) in 68% yield by a Horner-Wadsworth-Emmons reaction (Scheme 11).

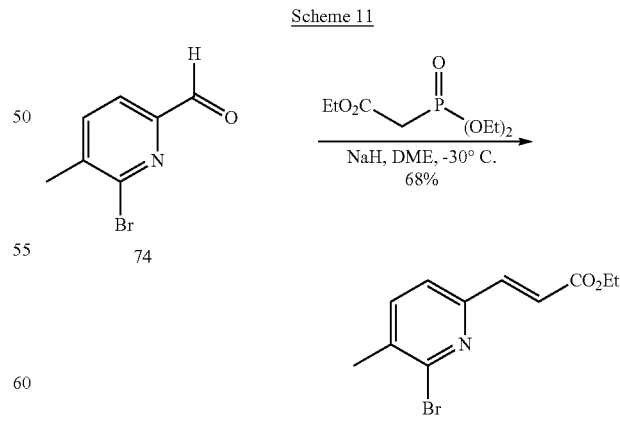

The acrylate 75 is reacted with the boronic acid 82 to give (E)-ethyl 3-(5-methyl-6-(3,5,5,8,8-pentamethyl-5,6,7,8-tetrahydronaphthalen-2-yl)pyridin-2-yl)acrylate (76) in 57% yield which is saponified to (E)-3-(5-methyl-6-(3,5,5,8,8-pentamethyl-5,6,7,8-tetrahydronaphthalen-2-yl)pyridin-2-yl)acrylic acid (77) in 88% yield (Scheme 12).

Scheme 12

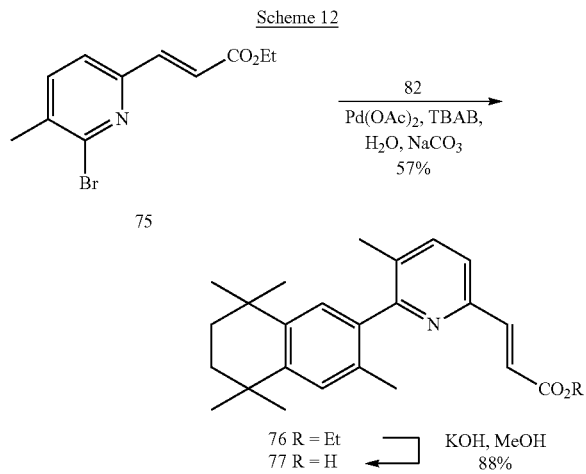

a. (E)-Ethyl 3-(6-bromo-5-methylpyridin-2-yl)acrylate (75)

To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 6-bromo-5-methylpicolinaldehyde (74) (1.35 g, 6.75 mmol) in DME (3 mL), and the reaction was stirred at −30° C. for 1.5 h and then poured into water (50 mL) and extracted with ethyl acetate. The combined organic layers were washed with an aqueous saturated $NH_4Cl$ solution and then brine, dried over sodium sulfate, filtered and concentrated in vacuo to give a crude product that was purified by column chromatography (150 mL $SiO_2$, 5% ethyl acetate: hexanes) to give 75 (1.249 g, 68%) as a colorless crystalline solid, m.p. 59-61° C.: $^1$H NMR (400 MHz, $CDCl_3$) δ 7.57 (dd, J=15.6, 3.2, 1H), 7.54 (ddd, J=15.2, 7.6, 0.8, 1H), 7.26 (t, J=7.6, 1H), 6.88 (dd, J=15.6, 3.2, 1H), 4.25 (q, J=7.2, 2H), 2.39 (s, 3H), 1.31 (t, J=7.2, 3H); $^{13}$C NMR (100.6 MHz, $CDCl_3$) δ 166.6, 166.5, 151.8, 151.3, 150.9, 145.0, 141.5, 141.3, 139.7, 139.0, 136.0, 133.5, 122.8, 122.7, 122.6, 60.6, 22.0, 19.7, 14.2; IR (neat) δ 2985, 1699, 1642, 1546 cm$^{-1}$; LC-FAB-MS (M)+ calcd for $C_{11}H_{12}BrNO_2$ [not yet assayed], found [not yet assayed]. (mix of isomers).

b. (E)-Ethyl 3-(5-methyl-6-(3,5,5,8,8-pentamethyl-5,6,7,8-tetrahydronaphthalen-2-yl)pyridin-2-yl)acrylate (76)

To a 50 mL Schlenk flask charged with bromide 75 (0.4355 g, 1.61 mmol), boronic acid 82 (0.411 g, 1.67 mmol), TBAB (0.52 g), $Na_2CO_3$ (0.51 g, 4.81 mmol), and water (3.7 mL), was added $Pd(OAc)_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL $SiO_2$, 5% ethyl acetate:hexanes) to give 76 (0.359 g, 57%) as a white solid, m.p. 127-130° C.: $^1$H NMR (400 MHz, $CDCl_3$) δ 7.75 (d, J=15.6, 1H), 7.59 (d, J=8.0, 1H), 7.36 (d, J=8.0, 1H), 7.17 (s, 1H), 7.08, (s, 1H), 6.83 (d, J=15.6, 1H), 4.25 (q, J=7.2, 2H), 2.16, (s, 3H), 2.07 (s, 3H), 1.68 (s, 4H), 1.30 (t, J=7.2, 3H), 1.30 (s, 6H), 1.25 (s, 6H); $^{13}$C NMR (100.6 MHz, $CDCl_3$) δ 166.9, 160.4, 149.9, 144.4, 143.9, 141.9, 138.3, 136.6, 132.8, 128.3, 126.7, 121.6, 121.3, 60.4, 35.2, 35.1, 34.0, 33.9, 31.8, 19.4, 19.3, 14.2; IR (neat) δ 2957, 1713, 1646 1569 cm$^{-1}$; LC-FAB-MS (M+Na)+ calcd for $C_{26}H_{33}NO_2Na$ 414.2409, found 414.2408.

c. (E)-3-(5-Methyl-6-(3,5,5,8,8-pentamethyl-5,6,7,8-tetrahydronaphthalen-2-yl)pyridin-2-yl)acrylic acid (77)

To a 100 mL round bottom flask containing 76 (0.6556 g, 1.67 mmol) suspended in methanol (4.8 mL) was added a solution of KOH (0.2902 g, 5.17 mmol) in water (0.38 mL), and the solution was refluxed in an oil-bath pre-heated to 85° C. for 1 h. The reaction was allowed to cool to room temperature, and acidified with an aqueous 20% HCl solution (50 mL). The resulting precipitate that was purified by column chromatography (25 mL $SiO_2$, ethyl acetate:hexanes 1:1) to give 77 (0.54 g, 88%) as a white crystalline solid, m.p. 230-234° C.: $^1$H NMR (400 MHz, $CDCl_3$) δ 7.85 (d, J=15.6, 1H), 7.63 (d, J=8.0, 1H), 7.39 (d, J=8.0, 1H), 7.18 (s, 1H), 7.09 (s, 1H), 6.87 (d, J=16.0, 1H), 2.17 (s, 3H), 2.08 (s, 3H), 1.68 (s, 4H), 1.30 (s, 6H), 1.25 (s, 6H); $^{13}$C NMR (100.6 MHz, $CDCl_3$) δ 171.8, 160.3, 149.4, 145.5, 144.6, 142.0, 138.7, 136.1, 133.5, 132.3, 128.3, 126.8, 122.2, 120.8, 35.2, 35.1, 34.0, 33.9, 31.9, 31.8, 19.5, 19.3; IR (neat) δ 2962, 1685, 1637 cm$^{-1}$; LC-FAB-MS (M−H)− calcd for $C_{24}H_{28}NO_2$ 362.2120, found 362.2130.

Example 6 Synthesis of (E)-3-(6-(3,5,5,8,8-pentamethyl-5,6,7,8-tetrahydronaphthalen-2-yl)pyridin-2-yl)acrylic acid (81) (A47)

Using a procedure similar to that described in Example 5, 6-bromopicolinaldehyde (78) was converted to (E)-ethyl 3-(6-bromopyridin-2-yl)acrylate (79) in 96% yield by a Horner-Wadsworth-Emmons reaction (Scheme 13).

Scheme 13

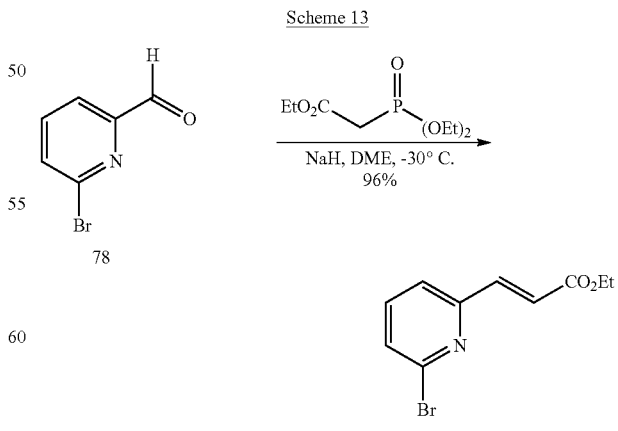

The acrylate 79 is then reacted with the boronic acid 82 to give (E)-ethyl 3-(6-(3,5,5,8,8-pentamethyl-5,6,7,8-tetrahydronaphthalen-2-yl)pyridin-2-yl)acrylate (80) in 44% yield which is saponified to (E)-3-(6-(3,5,5,8,8-pentamethyl-5,6,7,8-tetrahydronaphthalen-2-yl)pyridin-2-yl) acrylic acid (81) in 50% yield (Scheme 14).

Scheme 14

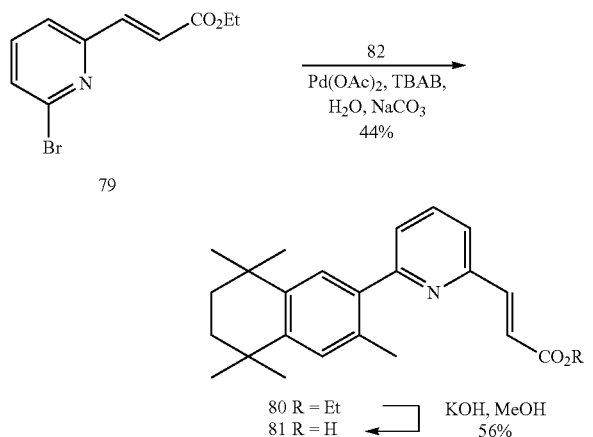

a. (E)-Ethyl 3-(6-bromopyridin-2-yl)acrylate (79)

To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 6-bromopicolinaldehyde (78) (1.24 g, 6.67 mmol) in DME (3 mL), and the reaction was stirred at −30° C. for 1.5 h and then poured into water (50 mL) and extracted with ethyl acetate. The combined organic layers were washed with an aqueous saturated $NH_4Cl$ solution and then brine, dried over sodium sulfate, filtered and concentrated in vacuo to give a crude product that was purified by column chromatography (150 mL $SiO_2$, 5% ethyl acetate:hexanes to 7% ethyl acetate:hexanes) to give 79 (1.6425 g, 96%) as a colorless crystalline solid, m.p. 63-66° C.: $^1$H NMR (400 MHz, $CDCl_3$) δ 7.57 (d, J=16.0, 1H), 7.55 (t, J=8.0, 1H), 7.44 (dd, J=8.0, 0.8, 1H), 7.34 (dd, J=7.6, 0.8, 1H), 6.93 (d, J=15.6, 1H), 4.26 (q, J=7.2, 2H), 1.32 (t, J=7.2, 3H); $^{13}$C NMR (100.6 MHz, $CDCl_3$) δ 166.3, 154.0, 142.5, 141.2, 138.9, 128.5, 123.9, 122.8, 60.7, 14.2; IR (neat) δ 2957, 1713, 1645, 1569 cm$^{-1}$; LC-FAB-MS (M+H)+ calcd for $C_{10}H_{11}BrNO_2$ 255.9973, found 255.9982.

b. (E)-Ethyl 3-(6-(3,5,5,8,8-pentamethyl-5,6,7,8-tetrahydronaphthalen-2-yl)pyridin-2-yl)acrylate (80)

To a 50 mL Schlenk flask charged with bromide 79 (0.4125 g, 1.61 mmol), boronic acid 82 (0.409 g, 1.66 mmol), TBAB (0.52 g), $Na_2CO_3$ (0.51 g, 4.81 mmol), and water (3.7 mL), was added $Pd(OAc)_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL $SiO_2$, 3% ethyl acetate:hexanes) to give 80 (0.2723 g, 44%) as a white solid, m.p. 107-110° C.: $^1$H NMR (400 MHz, $CDCl_3$) δ 7.77 (dd, J=15.6, 2.0, 1H), 7.76 (d, J=7.6, 1H), 7.41 (dd, J=7.6, 0.8, 1H), 7.36 (dd, J=7.6, 0.8, 1H), 7.35 (s, 1H), 7.22 (s, 1H), 6.97 (d, J=15.6, 1H), 4.27 (q, J=7.2, 2H), 2.38 (s, 3H), 1.70 (s, 4H), 1.33 (t, J=7.2, 3H), 1.30 (s, 12H); $^{13}$C NMR (100.6 MHz, $CDCl_3$) δ 166.9, 160.6, 151.9, 145.3, 143.4, 142.5, 137.0, 136.9, 132.9, 129.0, 127.9, 124.5, 122.3, 121.7, 60.5, 35.0, 34.0, 33.9, 31.9, 31.8, 20.2, 14.2; IR (neat) δ 2956, 1710, 1645 cm$^{-1}$; LC-FAB-MS (M+Na)+ calcd for $C_{25}H_{31}NO_2Na$ 400.2253, found 400.2247.

c. (E)-3-(6-(3,5,5,8,8-Pentamethyl-5,6,7,8-tetrahydronaphthalen-2-yl)pyridin-2-yl)acrylic acid (81)

To a 100 mL round bottom flask containing 80 (0.4752 g, 1.26 mmol) suspended in methanol (3.6 mL) was added a solution of KOH (0.2328 g, 4.15 mmol) in water (0.28 mL), and the solution was refluxed in an oil-bath pre-heated to 85° C. for 1 h. The reaction was allowed to cool to room temperature, and acidified with an aqueous 20% HCl solution (52 mL). The resulting precipitate was filtered and washed with copious amounts of water, and the crude white powder was purified by column chromatography (25 mL $SiO_2$, 1% methanol:ethyl acetate) to give 81 (0.2467 g, 56%) as a solid, m.p. 261-263° C.: $^1$H NMR (400 MHz, $CDCl_3$) δ 7.86-7.79 (m, 2H), 7.44 (d, J=4.8, 1H), 7.43-7.35 (m, 2H), 7.22 (s, 1H), 7.00 (d, J=14.4, 1H), 2.39 (s, 3H), 1.70 (s, 4H), 1.31 (s, 6H), 1.30 (s, 6H); $^{13}$C NMR (100.6 MHz, $CDCl_3$) δ 171.5, 171.3, 160.8, 151.5, 145.8, 145.5, 142.6, 137.2, 136.9, 132.9, 129.1, 128.1, 125.0, 122.4, 121.6, 35.1, 34.0, 33.9, 31.9, 31.8, 20.4; IR (neat) δ 2957, 1671, 1643, 1629, 1579 cm$^{-1}$; LC-FAB-MS (M−H)− calcd for $C_{23}H_{26}NO_2$ 348.1964, found 348.1973.

Example 7 Synthesis of Net-TMN (A54)

Scheme 15

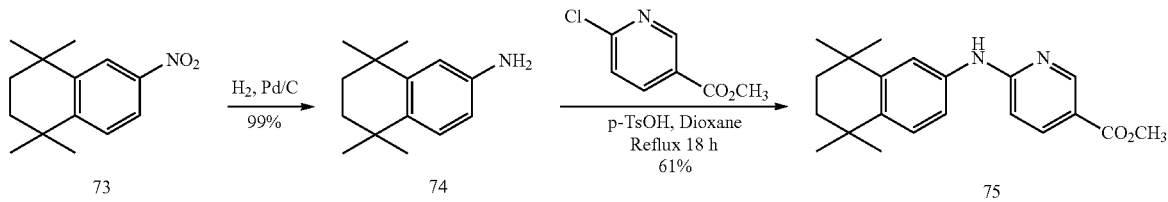

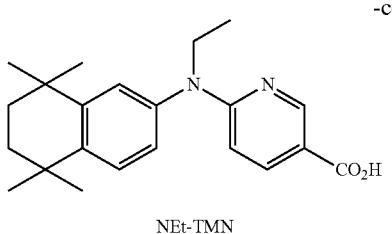

NEt-TMN

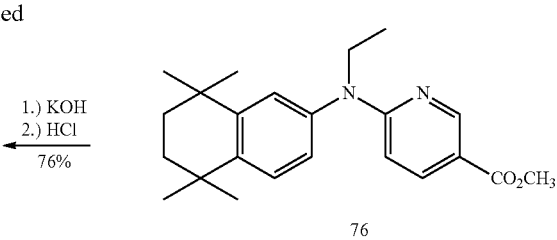

76

1.) KOH
2.) HCl
76%

The route of Kakuta and co-workers' was followed to reproduce NEt-TMN. Commercially available 1,1,4,4-tetramethyl-6-nitro-1,2,3,4-tetrahydronaphthalene (73) was dissolved in ethyl acetate to give a 0.05 M solution, and nitro-aromatic 73 was converted to 5,5,8,8-tetramethyl-5,6,7,8-tetrahydronaphthalen-2-amine (74) in 99% yield by catalytic hydrogenation using a hydrogenation flow reactor. Amine (74) was mixed with methyl 6-chloronicotinate and p-TsOH and refluxed in 1,4-dioxane for 18 h to give methyl 6-((5,5,8,8-tetramethyl-5,6,7,8-tetrahydronaphthalen-2-yl)amino)nicotinate (75) in 61% yield. Amine (75) in DMF was treated with sodium hydride and ethyl iodide was added to provide methyl 6-(ethyl(5,5,8,8-tetramethyl-5,6,7,8-tetrahydronaphthalen-2-yl)amino)nicotinate (76) in 68% yield. Finally, methyl ester 76 was saponified to NEt-TMN in 76% yield by refluxing a solution of 76 in methanol with potassium hydroxide followed by acidification with hydrochloric acid.

a. 5,5,8,8-Tetramethyl-5,6,7,8-tetrahydronaphthalen-2-amine (74)

A 0.05 M solution of 1,1,4,4-tetramethyl-6-nitro-1,2,3,4-tetrahydronaphthalene (73) (2.5 g, 10.7 mmol) in ethyl acetate (210 mL) was passed through a 10% Pd/C cartridge at 1.0 mL/minute, twice, in the ThalesNano H-cube® at 70° C. and 2-5 bar pressure. The resulting solution was concentrated in vacuo to give 74 (2.1532 g, 99%) as a yellow, crystalline solid, m.p. 58-60° C.: $^1$H NMR (400 MHz, CDCl$_3$) δ 7.11 (d, J=8.4, 1H), 6.65 (d, J=2.4, 1H), 6.54 (dd, J=8.4, 2.4, 1H), 3.62 (br s, 2H), 1.66 (s, 4H), 1.26 (s, 6H), 1.25 (s, 6H); $^{13}$C NMR (100.6 MHz, CDCl$_3$) δ 145.8, 143.3, 135.4, 127.3, 113.7, 112.9, 35.2, 34.1, 33.5, 31.9, 31.7; IR (neat) 3405, 3208, 2952, 2920, 1612, 1499 cm$^{-1}$; LC-MS-CI (M+H)+ calcd for C$_{14}$H$_{22}$N 204.1752, found 204.1747.

b. Methyl 6-((5,5,8,8-tetramethyl-5,6,7,8-tetrahydronaphthalen-2-yl)amino)nicotinate (75)

To a 100 mL, one-neck, round-bottomed flask equipped with a magnetic stir bar and charged with 74 (0.8047 g, 3.958 mmol), methyl 6-chloronicotinate (0.6897, 4.02 mmol), and p-TsOH (0.7605 g, 4.0 mmol) was added 1,4-dioxane (15 mL). The flask was fitted with a reflux condenser, evacuated and back-filled with nitrogen, heated to reflux and stirred in an oil bath at 111° C. for 14 h. After cooling the reaction to r.t., the reaction mixture was poured into water (50 mL) and extracted with ethyl acetate. The combined organic layers were washed with brine, dried over sodium sulfate, filtered, and concentrated in vacuo to yield a crude product that was purified by column chromatography (150 mL SiO$_2$, 10% ethyl acetate:hexanes) to give 75 (0.8152 g, 61%) as a white crystalline solid, m.p. 167-171° C.: $^1$H NMR (400 MHz, CDCl$_3$) δ 8.81 (dd, J=2.0, 0.4, 1H), 8.02 (dd, J=8.8, 2.0, 1H), 7.94 (s, 1H), 7.31 (d, J=7.6, 1H), 7.21 (d, J=2.4, 1H), 7.12 (dd, J=8.4, 2.4, 1H), 6.82 (dd, J=8.8, 0.4, 1H), 3.87 (s, 3H), 1.70 (s, 4H), 1.29 (s, 12H); $^{13}$C NMR (100.6 MHz, CDCl$_3$) δ 166.0, 159.4, 151.2, 146.3, 141.5, 138.9, 136.1, 127.5, 120.4, 120.0, 116.3, 106.0, 51.6, 35.0, 34.9, 34.3, 33.9, 31.8, 31.7; IR (neat) 3224, 2954, 1715, 1597, 1535, 1261 cm$^{-1}$; ES-MS (M+Na)+ calcd for C$_{21}$H$_{26}$N$_2$O$_2$Na 361.1892, found 361.1899.

c. Methyl 6-(ethyl(5,5,8,8-tetramethyl-5,6,7,8-tetrahydronaphthalen-2-yl)amino)nicotinate (76)

To a flame-dried, 100 mL round-bottomed flask equipped with a magnetic stir bar was added a 60% dispersion of sodium hydride in mineral oil (0.210 g, 5.25 mmol). The dispersion of sodium hydride was washed with hexanes (3 mL, twice) and dried under vacuum and suspended in 3.1 mL of DMF under nitrogen. To this solution of sodium hydride in DMF was added a solution of 75 (0.8386 g, 2.478 mmol) in DMF (8.3 mL), and the reaction was stirred for 15 min., and then ethyl iodide (0.34 mL, 4.25 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 76 (0.619 g, 68%) as a white crystalline solid, m.p. 114-116° C.: $^1$H NMR (400 MHz, CDCl$_3$) δ 8.83 (dd, J=2.4, 0.4, 1H), 7.78 (dd, J=9.2, 2.4, 1H), 7.35 (d, J=8.4, 1H), 7.11 (d, J=2.0, 1H), 6.95 (dd, J=8.4, 2.4, 1H), 6.21 (d, J=9.2, 1H), 4.02 (q, J=7.2, 2H), 3.85 (s, 3H), 1.70 (s, 4H), 1.31 (s, 6H), 1.25 (s, 6H), 1.22 (t, J=7.2, 3H); $^{13}$C NMR (100.6 MHz, CDCl$_3$) δ 166.6, 160.4, 151.0, 146.9, 143.8, 140.9, 137.2, 128.1, 125.8, 124.8, 114.2, 107.4, 51.5, 45.3, 35.0, 34.9, 34.4, 34.1, 31.8, 31.8, 13.0; IR (neat) 2956, 1708, 1596, 1267 cm$^{-1}$; ES-MS (M+Na)+ calcd for C$_{23}$H$_{30}$N$_2$O$_2$Na 389.2205, found 389.2211.

d. NEt-TMN

To a 100 mL round-bottomed flask equipped with a stir bar and charged with methyl ester 76 (0.3674 g, 1.002 mmol) suspended in methanol (3.5 mL) was added a solution of potassium hydroxide (0.1767 g, 3.15 mmol) in water (0.22 mL). This reaction was stirred at reflux in an oil bath at 87° C. for 1 h. The reaction was then cooled to r.t. and acidified with 20% HCl (52 mL). The crude white precipitate was filtered and washed with cold water to provide crude NEt-TMN (0.3238 g, 91%) and this crude material was purified by column chromatography (25 mL SiO$_2$, 30% ethyl acetate:hexanes to pure ethyl acetate to 2% methanol: ethyl acetate) to give NEt-TMN (0.2677 g, 76%) as a white crystalline solid, m.p. 230-232° C. (lit. 235.7-237.7° C.): $^1$H NMR (400 MHz, d6-DMSO) δ 12.44 (br s, 1H), 8.66 (dd, J=2.4, 0.4, 1H), 7.78 (dd, J=8.8, 2.4, 1H), 7.43 (d, J=8.0, 1H), 7.18 (d, J=2.0, 1H), 7.01 (dd, J=8.4, 2.4, 1H), 6.19 (dd, J=9.2, 0.4, 1H), 3.94 (q, J=6.8, 2H), 1.66 (s, 4H), 1.26 (s, 6H), 1.22 (s, 6H), 1.22 (t, J=6.8, 3H); $^{13}$C NMR (100.6 MHz, d6-DMSO) δ 166.6, 159.7, 150.5, 146.5, 143.1, 140.7, 137.6, 128.1, 125.4, 124.8, 114.7, 106.7, 44.7, 34.5. 34.4, 34.0, 33.8, 31.5, 31.4, 12.7; IR (neat) 2925, 1666, 1592, 1409, 1274 cm$^{-1}$; ES-MS (M–H)– calcd for $C_{22}H_{27}N_2O_2$ 351.2072, found 351.2073. Anal. Calcd for $C_{22}H_{28}N_2O_2$: C, 74.97; H, 8.01; N, 7.95. Found: C, 74.74; H, 8.38; N, 7.56.

Example 8 Synthesis of 6-(ethyl(3,5,5,8,8-pentamethyl-5,6,7,8-tetrahydronaphthalen-2-yl)amino)nicotinic acid (81) (A55)

solid particulates were filtered and washed with ethyl acetate, and the organic filtrate was concentrated in vacuo to give a crude product that was purified by column chromatography (150 mL SiO$_2$, 6.5% ethyl acetate:hexanes to 10% ethyl acetate:hexanes) to give 79 (0.5072 g, 37%) as a crystalline solid, m.p. 169-175.8° C.: $^1$H NMR (400 MHz, CDCl$_3$) δ 8.79 (dd, J=2.4, 0.8, 1H), 8.00 (dd, J=8.8, 2.0, 1H), 7.25 (s, 1H), 7.18 (s, 1H), 7.05 (br s, 1H), 6.49 (dd, J=8.8, 0.8, 1H), 3.87 (s, 3H), 2.20 (s, 3H), 1.68 (s, 4H), 1.29 (s, 6H), 1.25 (s, 6H); $^{13}$C NMR (100.6 MHz, CDCl$_3$) δ 166.1, 160.0, 151.3, 143.8, 143.0, 138.9, 134.1, 130.3, 129.1, 123.1, 116.1, 105.5, 51.7, 35.0, 34.9, 34.0, 33.9, 31.8, 31.8, 17.6; IR (neat) 2961, 1722, 1605, 1399, 1273 cm$^{-1}$; ES-MS (M+Na)+ calcd for $C_{22}H_{28}N_2O_2Na$ 375.2048, found 375.2050.

Scheme 16

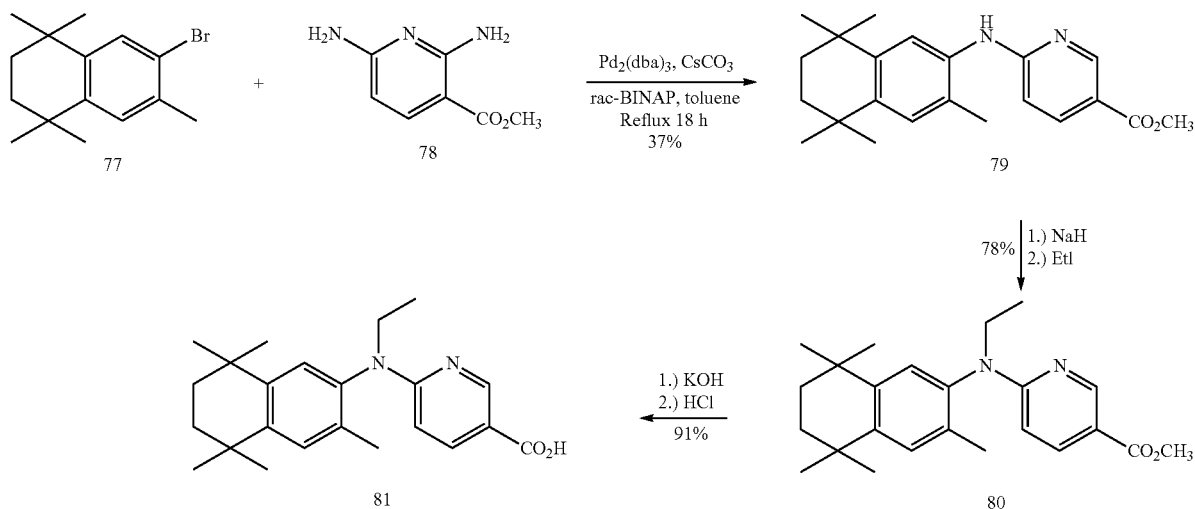

First, 6-bromo-1,1,4,4,7-pentamethyl-1,2,3,4-tetrahydronaphthalene (77) was coupled to methyl 6-aminonicotinate (78) in a tris(dibenzylideneacetone)dipalladium(0) catalytic system employing racemic BINAP to give methyl 6-((3,5,5,8,8-pentamethyl-5,6,7,8-tetrahydronaphthalen-2-yl)amino)nicotinate (79) in 37% purified yield. Methyl ester 79 was treated with sodium hydride in DMF followed by ethyl iodide to give methyl 6-(ethyl(3,5,5,8,8-pentamethyl-5,6,7,8-tetrahydronaphthalen-2-yl)amino)nicotinate (80) in 78% purified yield. The methyl ester of 80 was saponified by refluxing 80 in methanol with an aqueous solution of potassium hydroxide followed by acidification with 20% hydrochloric acid to give 6-(ethyl(3,5,5,8,8-pentamethyl-5,6,7,8-tetrahydronaphthalen-2-yl)amino)nicotinic acid (81).

a. Methyl 6-((3,5,5,8,8-pentamethyl-5,6,7,8-tetrahydronaphthalen-2-yl)amino)nicotinate (79)

To a solution of 77 (1.1216 g, 3.99 mmol), 78 (0.5910 g, 3.88 mmol), CsCO$_3$ (3.1158 g, 9.58 mmol), rac-BINAP (0.1856 g, 0.30 mmol) in toluene (4.5 mL) in a 100 mL round-bottomed flask was added Pd$_2$(dba)$_3$ (0.1755 g, 0.19 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other b. Methyl 6-(ethyl(3,5,5,8,8-pentamethyl-5,6,7,8-tetrahydronaphthalen-2-yl)amino)nicotinate (80)

To a flame-dried, 100 mL round-bottomed flask equipped with a magnetic stir bar was added a 60% dispersion of sodium hydride in mineral oil (0.2649 g, 6.6 mmol). The dispersion of sodium hydride was washed with hexanes (3.7 mL, twice) and dried under vacuum and suspended in 3.8 mL of DMF under nitrogen. To this solution of sodium hydride in DMF was added a solution of 79 (1.0615 g, 3.01 mmol) in DMF (11.4 mL), and the reaction was stirred for 15 min., and then ethyl iodide (0.36 mL, 4.5 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 80 (0.9012 g, 78%) as a white crystalline solid, m.p. 100.1-102.4° C.: $^1$H NMR (400 MHz, CDCl$_3$) δ 8.85 (dd, J=2.4, 0.4, 1H), 7.78 (dd, J=9.2, 2.4, 1H), 7.21 (s, 1H), 7.00 (s, 1H), 5.91 (d, J=8.8, 1H), 4.32-4.23 (m, 1H), 3.84 (s, 3H), 3.67-3.59 (m, 1H), 2.04 (s, 3H), 1.69 (s, 4H), 1.30 (d, J=8.0, 6H), 1.23 (t, J=7.2, 9H); $^{13}$C NMR (100.6 MHz, CDCl$_3$) δ 166.7, 160.2, 151.2, 144.6, 144.5, 139.1, 137.5, 132.8, 129.4, 127.0, 113.9, 106.7, 51.5, 44.5, 35.0, 34.9, 34.1, 34.0, 31.8, 17.2, 13.0; IR (neat) 2953, 1708, 1598, 1504, 1269, 1111 cm$^{-1}$; ES-MS (M+Na)+ calcd for $C_{24}H_{32}N_2O_2Na$ 403.2361, found 403.2365.

c. 6-(Ethyl(3,5,5,8,8-pentamethyl-5,6,7,8-tetrahydronaphthalen-2-yl)amino)nicotinic acid (81)

To a 100 mL round-bottomed flask equipped with a stir bar and charged with methyl ester 80 (0.5059 g, 1.33 mmol) suspended in methanol (4.6 mL) was added a solution of potassium hydroxide (0.2408 g, 4.29 mmol) in water (0.29 mL). This reaction was stirred at reflux in an oil bath at 87° C. for 1 h. The reaction was then cooled to r.t. and acidified with 20% HCl (72 mL). The solution was extracted with ethyl acetate (2×70 mL), and the organic layers were dried over sodium sulfate and concentrated in vacuo to give a crude product that was purified by column chromatography (25 mL $SiO_2$, 30% ethyl acetate:hexanes to 60% ethyl acetate:hexanes) to give pure 81 (0.4448 g, 91%) as a white crystalline solid, m.p. 250.2-251.0° C.: $^1$H NMR (400 MHz, d6-DMSO) δ 12.42 (br s, 1H), 8.66 (d, J=2.0, 1H), 7.78 (dd, J=8.8, 2.0, 1H), 7.32 (s, 1H), 7.07 (s, 1H), 5.89 (br s, 1H), 4.19-4.05 (m, 1H), 3.65-3.55 (m, 1H), 1.98 (s, 3H), 1.64 (s, 4H), 1.26 (d, J=6.4, 6H), 1.20 (s, 6H), 1.13 (t, J=7.2, 3H); $^{13}$C NMR (100.6 MHz, d6-DMSO) δ 166.6, 159.5, 150.7, 144.1, 143.8, 139.0, 137.9, 132.5, 129.2, 126.5, 114.4, 105.9, 44.0, 34.5, 34.4, 33.7, 31.6, 31.5, 16.9, 12.7; IR (neat) 2960, 1669, 1595, 1509, 1412, 1266 cm$^{-1}$; ES-MS (M−H)− calcd for $C_{23}H_{29}N_2O_2$ 365.2229, found 365.2235. Anal. Calcd for $C_{23}H_{30}N_2O_2$: C, 75.37; H, 8.25; N, 7.64. Found: C, 75.33; H, 8.46; N, 7.56.

Example 9 Synthesis of 2-(ethyl(5,5,8,8-tetramethyl-5,6,7,8-tetrahydronaphthalen-2-yl)amino)pyrimidine-5-carboxylic acid (84) (A56)

Amine (74) was mixed with methyl 2-chloropyrimidine and p-TsOH and refluxed in 1,4-dioxane for 18 h to give methyl 2-(5,5,8,8-tetramethyl-5,6,7,8-tetrahydronaphthalen-2-yl)amino)pyrimidine-5-carboxylate (82) in 75% yield. Amine (82) in DMF was treated with sodium hydride and ethyl iodide was added to provide methyl 2-(ethyl(5,5,8,8-tetramethyl-5,6,7,8-tetrahydronaphthalen-2-yl)amino)pyrimidine-5-carboxylate (83) in 75% yield. Finally, methyl ester 83 was saponified to 84 in 97% yield by refluxing a solution of 83 in methanol with potassium hydroxide followed by acidification with hydrochloric acid (Scheme 17).

a. Methyl 2-((5,5,8,8-tetramethyl-5,6,7,8-tetrahydronaphthalen-2-yl)amino)pyrimidine-5-carboxylate (82)

To a 100 mL, one-neck, round-bottomed flask equipped with a magnetic stir bar and charged with 74 (0.8047 g, 3.958 mmol), methyl 6-chloronicotinate (0.6897, 4.02 mmol), and p-TsOH (0.8101 g, 3.98 mmol) was added 1,4-dioxane (15 mL). The flask was fitted with a reflux condenser, evacuated and back-filled with nitrogen, heated to reflux and stirred in an oil bath at 111° C. for 14 h. After cooling the reaction to r.t., the reaction mixture was poured into water (50 mL) and extracted with ethyl acetate. The combined organic layers were washed with brine, dried over sodium sulfate, filtered, and concentrated in vacuo to yield a crude product that was purified by column chromatography (150 mL $SiO_2$, 10% ethyl acetate:hexanes to 12% ethyl acetate:hexanes) to give 82 (1.0177 g, 75%) as a white crystalline solid, m.p. 143.2-149.3° C.: $^1$H NMR (400 MHz, CDCl$_3$) δ 8.95 (s, 2H), 8.25 (br s, 1H), 7.47 (dd, J=8.4, 2.4, 1H), 7.42 (d, J=2.0, 1H), 7.32 (d, J=8.4, 1H), 3.90 (s, 3H), 1.69 (s, 4H), 1.30 (s, 6H), 1.28 (s, 6H); $^{13}$C NMR (100.6 MHz, CDCl$_3$) δ 164.7, 161.4, 145.7, 141.1, 135.3, 127.1, 118.8, 118.7, 114.7, 51.9, 35.0, 34.3, 33.9, 31.8, 31.8; IR (neat) 3254, 2954, 1720, 1597, 1526, 1433, 1289, 1258, 1123 cm$^{-1}$; ES-MS (M+Na)+ calcd for $C_{20}H_{25}N_3O_2Na$ 362.1844, found 362.1844.

b. Methyl 2-(ethyl(5,5,8,8-tetramethyl-5,6,7,8-tetrahydronaphthalen-2-yl)amino)pyrimidine-5-carboxylate (83)

To a flame-dried, 100 mL round-bottomed flask equipped with a magnetic stir bar was added a 60% dispersion of sodium hydride in mineral oil (0.251 g, 6.3 mmol). The dispersion of sodium hydride was washed with hexanes (3 mL, twice) and dried under vacuum and suspended in 3.6 mL of DMF under nitrogen. To this solution of sodium hydride in DMF was added a solution of 82 (0.9851 g, 2.9 mmol) in DMF (10.9 mL), and the reaction was stirred for 15 min., and then ethyl iodide (0.35 mL, 4.38 mmol) was

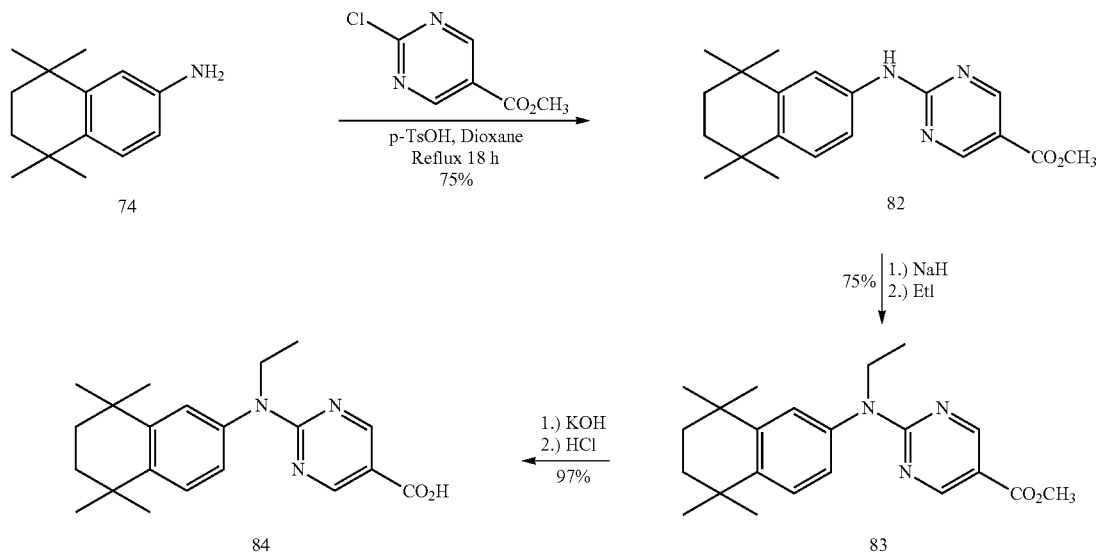

Scheme 17 added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 83 for C$_{21}$H$_{26}$N$_3$O$_2$ 352.2025, found 352.2024. Anal. Calcd for C$_{21}$H$_{27}$N$_3$O$_2$: C, 71.36; H, 7.70; N, 11.89. Found: C, 71.40; H, 7.98; N, 11.79.

Example 10 Synthesis of 2-(ethyl(3,5,5,8,8-pentamethyl-5,6,7,8-tetrahydronaphthalen-2-yl)amino)pyrimidine-5-carboxylic acid (88) (A57)

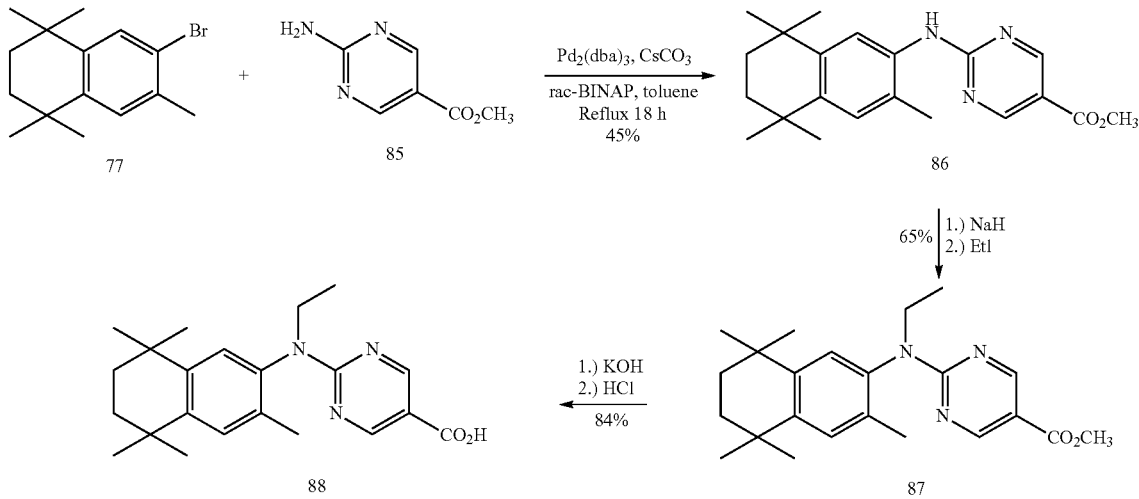

Scheme 18

(0.7997 g, 75%) as a white crystalline solid, m.p. 181.2-183.9° C.: $^1$H NMR (400 MHz, CDCl$_3$) δ 8.85 (s, 1H), 7.33 (d, J=8.4, 1H), 7.13 (d, J=2.4, 1H), 7.00 (d, J=2.4, 1H), 6.98 (d, J=2.0, 1H), 4.03 (q, J=7.2, 2H), 3.86 (s, 3H), 1.69 (s, 4H), 1.30 (s, 6H), 1.26 (s, 6H), 1.24 (t, J=7.2, 3H); $^{13}$C NMR (100.6 MHz, CDCl$_3$) δ 165.3, 162.4, 159.7, 146.0, 143.3, 140.3, 127.4, 125.1, 124.2, 112.9, 51.6, 46.5, 35.0, 34.9, 34.3, 34.1, 31.8, 31.8, 12.8; IR (neat) 2930, 1706, 1594, 1504, 1284, 1122 cm$^{-1}$; ES-MS (M+Na)+ calcd for C$_{22}$H$_{29}$N$_3$O$_2$Na 390.2158, found 390.2155.

c. 2-(Ethyl(5,5,8,8-tetramethyl-5,6,7,8-tetrahydronaphthalen-2-yl)amino)pyrimidine-5-carboxylic acid (84)

To a 100 mL round-bottomed flask equipped with a stir bar and charged with methyl ester 83 (0.3925 g, 1.07 mmol) suspended in methanol (4.2 mL) was added a solution of potassium hydroxide (0.1947 g, 3.47 mmol) in water (0.26 mL). This reaction was stirred at reflux in an oil bath at 87° C. for 1 h. The reaction was then cooled to r.t. and acidified with 20% HCl (76 mL). The crude white precipitate was filtered and washed with cold water to provide crude 84 and this crude material was purified by column chromatography (25 mL SiO$_2$, 40% ethyl acetate:hexanes to pure ethyl acetate) to give 84 (0.3668 g, 97%) as a white crystalline solid, m.p. 249.5-250.6° C.: $^1$H NMR (400 MHz, d6-DMSO) δ 12.62 (br s, 1H), 8.37 (s, 1H), 7.35 (d, J=8.4, 1H), 7.17 (d, J=2.4, 1H), 7.00 (dd, J=8.4, 2.0, 1H), 3.99 (q, J=7.2, 2H), 1.67 (s, 4H), 1.27 (s, 6H), 1.24 (s, 6H), 1.16 (t, J=7.2, 3H); $^{13}$C NMR (100.6 MHz, d6-DMSO) δ 165.1, 161.9, 159.1, 15.2, 142.3, 140.2, 126.8, 124.7, 124.6, 113.5, 45.3, 34.4, 34.4, 33.7, 33.5, 31.4, 31.3, 12.3; IR (neat) 2962, 1664, 1586, 1515, 1426, 1278 cm$^{-1}$; ES-MS (M−H)− calcd First, 6-bromo-1,1,4,4,7-pentamethyl-1,2,3,4-tetrahydronaphthalene (77) was coupled to methyl 2-aminopyrimidine-5-carboxylate (85) in a tris(dibenzylideneacetone)dipalladium(0) catalytic system employing racemic BINAP to give methyl 2-(3,5,5,8,8-pentamethyl-5,6,7,8-tetrahydronaphthalen-2-yl)amino)pyrimidine-5-carboxylate (86) in 45% purified yield. Methyl ester 86 was treated with sodium hydride in DMF followed by ethyl iodide to give methyl 2-(ethyl(3,5,5,8,8-pentamethyl-5,6,7,8-tetrahydronaphthalen-2-yl)amino)pyrimidine-5-carboxylate (87) in 65% purified yield. The methyl ester of 87 was saponified by refluxing 87 in methanol with an aqueous solution of potassium hydroxide followed by acidfication with 20% hydrochloric acid to give 2-(ethyl(3,5,5,8,8-pentamethyl-5,6,7,8-tetrahydronaphthalen-2-yl)amino)pyrimidine-5-carboxylic acid (88).

a. Methyl 2-((3,5,5,8,8-pentamethyl-5,6,7,8-tetrahydronaphthalen-2-yl)amino)pyrimidine-5-carboxylate (86)

To a solution of 77 (1.1216 g, 3.99 mmol), 85 (0.5985 g, 3.91 mmol), CsCO$_3$ (3.12 g, 9.58 mmol), rac-BINAP (0.1891 g, 0.30 mmol) in toluene (4.5 mL) in a 100 mL round-bottomed flask was added Pd$_2$(dba)$_3$ (0.1780 g, 0.19 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL SiO$_2$, 5% ethyl acetate:hexanes to 10% ethyl acetate: hexanes) to give 86 (0.6206 g, 45%) as a crystalline solid, m.p. 135.6-145.6° C.: $^1$H NMR (400 MHz, CDCl$_3$) δ 8.92 (s, 2H), 7.65 (s, 1H), 7.45 (br s, 1H), 7.16 (s, 1H), 3.89 (s, 3H), 2.24 (s, 3H), 1.68 (s, 4H), 1.29 (s, 6H), 1.28 (s, 6H); $^{13}$C NMR (100.6 MHz, CDCl$_3$) δ 164.8, 162.0, 160.2, 143.4, 133.2, 128.7, 128.4, 122.1, 114.6, 51.8, 35.1, 35.0, 34.1, 33.9, 31.8, 31.7, 17.8; IR (neat) 3250, 2954, 1718, 1598, 1527, 1430, 1286 cm$^{-1}$; ES-MS (M+Na)+ calcd for C$_{21}$H$_{27}$N$_3$O$_2$Na 376.2001, found 376.1998.

b. Methyl 2-(ethyl(3,5,5,8,8-pentamethyl-5,6,7,8-tetrahydronaphthalen-2-yl)amino)pyrimidine-5-carboxylate (87)

To a flame-dried, 100 mL round-bottomed flask equipped with a magnetic stir bar was added a 60% dispersion of sodium hydride in mineral oil (0.2622 g, 6.56 mmol). The dispersion of sodium hydride was washed with hexanes (3.7 mL, twice) and dried under vacuum and suspended in 3.4 mL of DMF under nitrogen. To this solution of sodium hydride in DMF was added a solution of 86 (0.974 g, 2.76 mmol) in DMF (10.3 mL), and the reaction was stirred for 15 min., and then ethyl iodide (0.34 mL, 4.25 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 87 (0.688 g, 65%) as a white crystalline solid, m.p. 159.2-161.0° C.: $^1$H NMR (400 MHz, CDCl$_3$) δ 8.93 (s, 1H), 8.78 (s, 1H), 7.19 (s, 1H), 7.00 (s, 1H), 4.15 (sextet, J=7.2, 1H), 3.85 (s, 3H), 3.74 (sextet, J=7.2, 1H), 2.05 (s, 3H), 1.68-1.66 (m, 4H), 1.32 (s, 3H), 1.27 (s, 3H), 1.26 (s, 3H), 1.25 (s, 3H), 1.24 (t, J=7.2, 3H); $^{13}$C NMR (100.6 MHz, CDCl$_3$) δ 165.4, 162.3, 160.0, 159.8, 143.8, 143.7, 139.2, 132.1, 129.0, 125.8, 112.6, 51.6, 46.0, 35.1, 34.9, 34.0, 34.0, 32.0, 32.0, 31.7, 31.6, 17.5, 12.7; IR (neat) 2955, 1703, 1594, 1513, 1279, 1267, 1126, 1099 cm$^{-1}$; ES-MS (M+Na)+ calcd for C$_{23}$H$_{31}$N$_3$O$_2$Na 404.2314, found 404.2312.

c. 2-(Ethyl(3,5,5,8,8-pentamethyl-5,6,7,8-tetrahydronaphthalen-2-yl)amino)pyrimidine-5-carboxylic acid (88)

To a 100 mL round-bottomed flask equipped with a stir bar and charged with methyl ester 87 (0.3892 g, 1.04 mmol) suspended in methanol (3.5 mL) was added a solution of potassium hydroxide (0.1789 g, 3.19 mmol) in water (0.22 mL). This reaction was stirred at reflux in an oil bath at 87° C. for 1 h. The reaction was then cooled to r.t. and acidified with 20% HCl (53 mL). The precipitate was filtered to give 0.3547 g (92%) of a crude product that was purified by column chromatography (25 mL SiO$_2$, 40% ethyl acetate: hexanes to ethyl acetate) to give pure 88 (0.3203 g, 84%) as a white crystalline solid, m.p. 231.9-233.1° C.: $^1$H NMR (400 MHz, d6-DMSO) δ 12.60 (br s, 1H), 8.74 (br s, 2H), 7.23 (s, 1H), 7.05 (s, 1H), 4.04 (sextet, J=7.2, 1H), 3.76 (sextet, J=7.2, 1H), 1.97 (s, 3H), 1.65 (s, 4H), 1.29, (s, 3H), 1.26 (s, 3H), 1.23 (s, 3H), 1.20 (s, 3H), 1.16 (t, J=7.2, 3H); $^{13}$C NMR (100.6 MHz, d6-DMSO) δ 165.2, 161.7, 159.3, 143.0, 142.9, 139.1, 132.0, 128.2, 125.4, 113.2, 45.0, 34.5, 34.4, 33.4, 33.3, 31.5, 31.4, 31.2, 16.9, 12.3; IR (neat) 2952, 1663, 1591, 1508, 1426, 1281 cm$^{-1}$; ES-MS (M–H)– calcd for C$_{22}$H$_{28}$N$_3$O$_2$ 366.2181, found 366.2185. Anal. Calcd for C$_{22}$H$_{29}$N$_3$O$_2$: C, 71.90; H, 7.95; N, 11.43. Found: C, 71.81; H, 8.23; N, 11.31.

Example 11 Synthesis of 5-(ethyl(5,5,8,8-tetramethyl-5,6,7,8-tetrahydronaphthalen-2-yl)amino)pyrazine-2-carboxylic acid (91) (A58)

Amine (74) was mixed with methyl 5-chloropyrazine-2-carboxylate and p-TsOH and refluxed in 1,4-dioxane for 18 h to give methyl 5-(5,5,8,8-tetramethyl-5,6,7,8-tetrahydronaphthalen-2-yl)amino)pyrazine-2-carboxylate (89) in 56% yield. Amine (89) in DMF was treated with sodium hydride and ethyl iodide was added to provide methyl 5-(ethyl(5,5,8,8-tetramethyl-5,6,7,8-tetrahydronaphthalen-2-yl)amino)pyrazine-2-carboxylate (90) in 51% yield. Finally, methyl ester 90 was saponified to 91 in 71% yield by refluxing a solution of 90 in methanol with potassium hydroxide followed by acidification with hydrochloric acid (Scheme 19).

Scheme 19

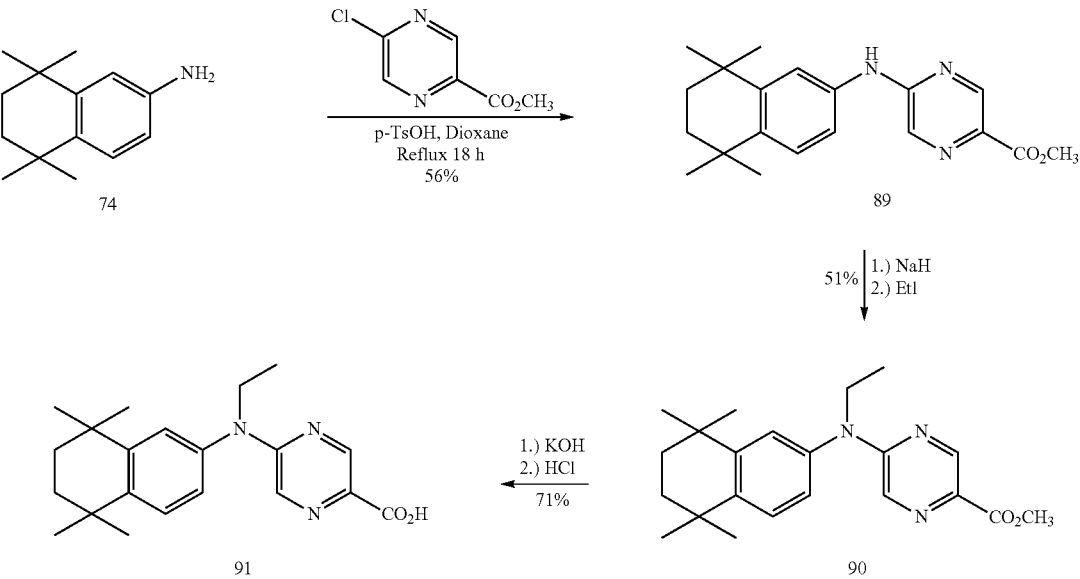

a. Methyl 5-((5,5,8,8-tetramethyl-5,6,7,8-tetrahydronaphthalen-2-yl)amino)pyrazine-2-carboxylate (89)

To a 100 mL, one-neck, round-bottomed flask equipped with a magnetic stir bar and charged with 74 (0.8154 g, 4.01 mmol), methyl 5-chloropyrazine-2-carboxylate (0.6897, 4.04 mmol), and p-TsOH (0.7757 g, 4.08 mmol) was added 1,4-dioxane (15 mL). The flask was fitted with a reflux condenser, evacuated and back-filled with nitrogen, heated to reflux and stirred in an oil bath at 111° C. for 14 h. After cooling the reaction to r.t., the reaction mixture was poured into water (50 mL) and extracted with ethyl acetate. The combined organic layers were washed with brine, dried over sodium sulfate, filtered, and concentrated in vacuo to yield a crude product that was purified by column chromatography (150 mL SiO$_2$, 10% ethyl acetate:hexanes) to give 89 (0.7674 g, 56%) as a white crystalline solid, m.p. 183.2-184.8° C.: $^1$H NMR (400 MHz, CDCl$_3$) δ 8.83 (d, J=1.6, 1H), 8.26 (d, J=1.2, 1H), 7.53 (br s, 1H), 7.33 (d, J=8.4, 1H), 7.32 (d, J=2.4, 1H), 7.21 (dd, J=8.4, 2.4, 1H), 3.95 (s, 3H), 1.68 (s, 4H), 1.27 (s, 6H), 1.26 (s, 6H); $^{13}$C NMR (100.6 MHz, CDCl$_3$) δ 164.9, 153.8, 146.3, 145.4, 142.1, 134.9, 132.6, 131.6, 127.7, 119.5, 119.2, 52.3, 34.9, 34.8, 34.3, 34.0, 31.7; IR (neat) 3325, 2952, 1713, 1527, 1281 cm$^{-1}$; ES-MS (M+Na)+ calcd for C$_{20}$H$_{25}$N$_3$O$_2$Na 362.1844, found 362.1846.

b. Methyl 5-(ethyl(5,5,8,8-tetramethyl-5,6,7,8-tetrahydronaphthalen-2-yl)amino)pyrazine-2-carboxylate (90)

To a flame-dried, 100 mL round-bottomed flask equipped with a magnetic stir bar was added a 60% dispersion of sodium hydride in mineral oil (0.2116 g, 5.29 mmol). The dispersion of sodium hydride was washed with hexanes (3 mL, twice) and dried under vacuum and suspended in 2.8 mL of DMF under nitrogen. To this solution of sodium hydride in DMF was added a solution of 89 (0.7637 g, 2.25 mmol) in DMF (8.4 mL), and the reaction was stirred for 15 min., and then ethyl iodide (0.27 mL, 3.4 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate: hexanes) to give 90 (0.4189 g, 51%) as a white crystalline solid, m.p. 125.0-126.9° C.: $^1$H NMR (400 MHz, CDCl$_3$) δ 8.82 (d, J=1.6, 1H), 7.66 (d, J=1.2, 1H), 7.39 (d, J=8.4, 1H), 7.12 (d, J=2.4, 1H), 6.95 (dd, J=8.4, 2.4, 1H), 4.00 (q, J=7.2, 2H), 3.92 (s, 3H), 1.69 (s, 4H), 1.29 (s, 6H), 1.24 (s, 6H), 1.23 (t, J=7.2, 3H); $^{13}$C NMR (100.6 MHz, CDCl$_3$) δ 165.2, 155.2, 147.3, 145.3, 144.7, 139.2, 131.7, 131.5, 130.3, 128.6, 125.4, 124.3, 52.1, 45.4, 34.9, 34.8, 34.4, 34.2, 31.8, 31.7; IR (neat) 2956, 1703, 1564, 1527, 1279 cm$^{-1}$; ES-MS (M+Na)+ calcd for C$_{22}$H$_{29}$N$_3$O$_2$Na 390.2158, found 390.2146.

c. 5-(Ethyl(5,5,8,8-tetramethyl-5,6,7,8-tetrahydronaphthalen-2-yl)amino)pyrazine-2-carboxylic acid (91)

To a 100 mL round-bottomed flask equipped with a stir bar and charged with methyl ester 90 (0.3681 g, 1.00 mmol) suspended in methanol (3.5 mL) was added a solution of potassium hydroxide (0.1794 g, 3.2 mmol) in water (0.22 mL). This reaction was stirred at reflux in an oil bath at 87° C. for 1 h. The reaction was then cooled to r.t. and acidified with 20% HCl (56 mL). The crude white precipitate was filtered and washed with cold water to provide crude 91 (0.3216 g, 91%) and this crude material was purified by column chromatography (25 mL SiO$_2$, 0.5% acetic acid: ethyl acetate to 4% acetic acid:ethyl acetate) to give 91 (0.2516 g, 71%) as a white crystalline solid, m.p. 213.1-214.4° C.: $^1$H NMR (400 MHz, d6-DMSO) δ 12.59 (br s, 1H), 8.70 (d, J=1.6, 1H), 7.61 (d, J=1.2, 1H), 7.47 (d, J=8.0, 1H), 7.29 (d, J=2.4, 1H), 7.10 (dd, J=8.4, 2.4, 1H), 3.94 (q, J=7.1, 2H), 1.66 (s, 4H), 1.27 (s, 6H), 1.23 (s, 6H), 1.14 (t, J=7.2, 3H); $^{13}$C NMR (100.6 MHz, d6-DMSO) δ 165.4, 154.4, 146.7, 144.6, 143.8, 139.2, 130.8, 130.7, 128.4, 125.2, 124.4, 44.9, 34.4, 34.4, 34.1, 33.8, 31.5, 31.4, 12.2; IR (neat) 2931, 1671, 1556, 1416, 1276 cm$^{-1}$; ES-MS (M-H)− calcd for C$_{21}$H$_{26}$N$_3$O$_2$ 352.2025, found 352.2020. Anal. Calcd for C$_{21}$H$_{27}$N$_3$O$_2$: C, 71.36; H, 7.70; N, 11.89. Found: C, 70.43; H, 7.64; N, 11.61.

Example 12 Synthesis of 5-(ethyl(3,5,5,8,8-pentamethyl-5,6,7,8-tetrahydronaphthalen-2-yl)amino)pyrazine-2-carboxylic acid (95) (A59)

Scheme 20

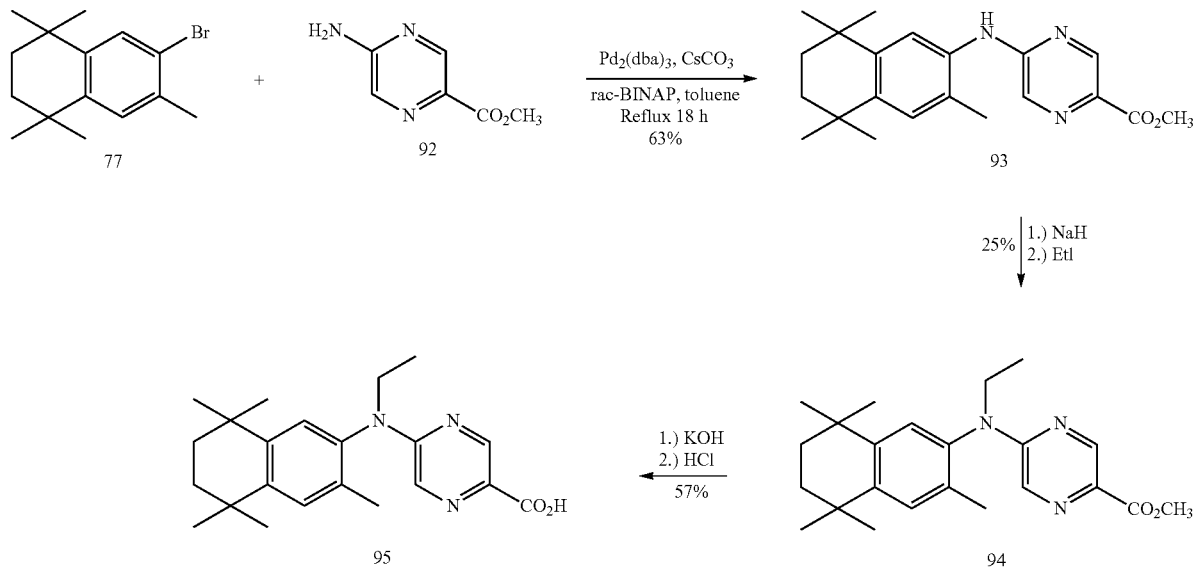

6-Bromo-1,1,4,4,7-pentamethyl-1,2,3,4-tetrahydronaphthalene (77) was coupled to methyl 5-aminopyrazine-2-carboxylate (92) in a tris(dibenzylideneacetone)dipalladium (0) catalytic system employing racemic BINAP to give methyl 5-((3,5,5,8,8-pentamethyl-5,6,7,8-tetrahydronaphthalen-2-yl)amino)pyrazine-2-carboxylate (93) in 63% purified yield. Methyl ester 93 was treated with sodium hydride in DMF followed by ethyl iodide to give methyl 5-(ethyl(3,5,5,8,8-pentamethyl-5,6,7,8-tetrahydronaphthalen-2-yl)amino)pyrazine-2-carboxylate (94) in 25% purified yield. The methyl ester of 94 was saponified by refluxing 94 in methanol with an aqueous solution of potassium hydroxide followed by acidfication with 20% hydrochloric acid to give 5-(ethyl(3,5,5,8,8-pentamethyl-5,6,7,8-tetrahydronaphthalen-2-yl)amino)pyrazine-2-carboxylic acid (95) in 57% yield.

a. Methyl 5-((3,5,5,8,8-pentamethyl-5,6,7,8-tetrahydronaphthalen-2-yl)amino)pyrazine-2-carboxylate (93)

To a solution of 77 (1.1303 g, 4.02 mmol), 92 (0.5969 g, 3.90 mmol), $CsCO_3$ (3.12 g, 9.58 mmol), rac-BINAP (0.1868 g, 0.30 mmol) in toluene (4.5 mL) in a 100 mL round-bottomed flask was added $Pd_2(dba)_3$ (0.1780 g, 0.19 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL $SiO_2$, 20% ethyl acetate:hexanes to 25% ethyl acetate: hexanes) to give 93 (0.8727 g, 63%) as a crystalline solid, m.p. 134.9-137.1° C.: $^1H$ NMR (400 MHz, $CDCl_3$) δ 8.81 (d, J=1.2, 1H), 8.08 (d, J=1.6, 1H), 7.32 (s, 1H), 7.20 (s, 1H), 7.03 (br s, 1H), 3.95 (s, 3H), 2.22 (s, 3H), 1.68 (s, 4H), 1.28 (s, 6H), 1.24 (s, 6H); $^{13}C$ NMR (100.6 MHz, $CDCl_3$) δ 164.8, 154.3, 145.4, 144.1, 143.6, 132.8, 130.7, 129.5, 129.3, 122.2, 52.3, 34.9, 34.8, 34.1, 33.9, 31.8, 31.7, 17.6; IR (neat) 3162, 2961, 1712, 1542, 1306, 1271, 1129 $cm^{-1}$; ES-MS (M+Na)+ calcd for $C_{21}H_{27}N_3O_2Na$ 376.2001, found 376.2006.

b. Methyl 5-(ethyl(3,5,5,8,8-pentamethyl-5,6,7,8-tetrahydronaphthalen-2-yl)amino)pyrazine-2-carboxylate (94)

To a flame-dried, 100 mL round-bottomed flask equipped with a magnetic stir bar was added a 60% dispersion of sodium hydride in mineral oil (0.2286 g, 5.7 mmol). The dispersion of sodium hydride was washed with hexanes (3.0 mL, twice) and dried under vacuum and suspended in 2.9 mL of DMF under nitrogen. To this solution of sodium hydride in DMF was added a solution of 93 (0.8405 g, 2.38 mmol) in DMF (8.9 mL), and the reaction was stirred for 15 min., and then ethyl iodide (0.30 mL, 3.8 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL $SiO_2$, 15% ethyl acetate:hexanes) to give 94 (0.226 g, 25%) as a white crystalline solid, m.p. 115.0-119.5° C.: $^1H$ NMR (400 MHz, $CDCl_3$) δ 8.84 (d, J=1.2, 1H), 7.38 (br s, 1H), 7.24 (s, 1H), 7.00 (s, 1H), 4.24 (sextet, J=7.2, 1H), 3.91 (s, 3H), 3.59 (sextet, J=7.2, 1H), 2.06 (s, 3H), 1.68 (s, 4H), 1.29 (s, 6H), 1.24 (s, 3H), 1.24 (t, J=7.2, 3H), 1.19 (s, 3H); $^{13}C$ NMR (100.6 MHz, $CDCl_3$) δ 165.4, 155.0, 145.4, 145.3, 145.0, 137.5, 132.4, 131.2, 130.2, 129.8, 126.6, 52.1, 44.5, 34.9, 34.8, 34.1, 34.0, 31.9, 31.8, 31.7, 17.1, 12.4; IR (neat) 2928, 1702, 1567, 1524, 1273, 1129 $cm^{-1}$; ES-MS (M+Na)+ calcd for $C_{23}H_{31}N_3O_2Na$ 404.2314, found 404.2305.

c. 5-(Ethyl(3,5,5,8,8-pentamethyl-5,6,7,8-tetrahydronaphthalen-2-yl)amino)pyrazine-2-carboxylic acid (95)

To a 100 mL round-bottomed flask equipped with a stir bar and charged with methyl ester 94 (0.2309 g, 0.605 mmol) suspended in methanol (2.1 mL) was added a solution of potassium hydroxide (0.1096 g, 1.95 mmol) in water (0.18 mL). This reaction was stirred at reflux in an oil bath at 87° C. for 1 h. The reaction was then cooled to r.t. and acidified with 20% HCl (36 mL). The precipitate was filtered to give 0.2060 g (92%) of a crude product that was purified by column chromatography (25 mL $SiO_2$, 0.5% acetic acid:ethyl acetate to 4% acetic acid:ethyl acetate) to give pure 95 (0.126 g, 57%) as a white crystalline solid, m.p. 203.6-205.1° C.: $^1H$ NMR (400 MHz, d6-DMSO) δ 12.69 (br s, 1H), 8.70 (s, 1H), 7.36 (br s, 2H), 7.15 (s, 1H), 4.15-4.05 (m, 1H), 3.59 (sextet, J=7.2, 1H), 2.03 (s, 3H), 1.65 (s, 4H), 1.29, (s, 3H), 1.26 (s, 3H), 1.22 (s, 3H), 1.20 (s, 3H), 1.15 (t, J=7.2, 3H); $^{13}C$ NMR (100.6 MHz, d6-DMSO) δ 165.4, 154.2, 144.8, 144.4, 144.3, 137.6, 132.3, 130.8, 130.0, 129.5, 126.4, 44.1, 34.5, 34.4, 33.7, 31.6. 31.5, 16.8, 12.1; IR (neat) 2959, 1671, 1557, 1524, 1417, 1286 $cm^{-1}$; ES-MS (M−H)− calcd for $C_{22}H_{28}N_3O_2$ 366.2181, found 366.2179. Anal. Calcd for $C_{22}H_{29}N_3O_2$: C, 71.90; H, 7.95; N, 11.43. Found: C, 71.62; H, 8.21; N, 11.19.

Example 13 Synthesis of 4-(ethyl(5,5,8,8-tetramethyl-5,6,7,8-tetrahydronaphthalen-2-yl)amino)benzoic acid (99) (A63)

Scheme 21

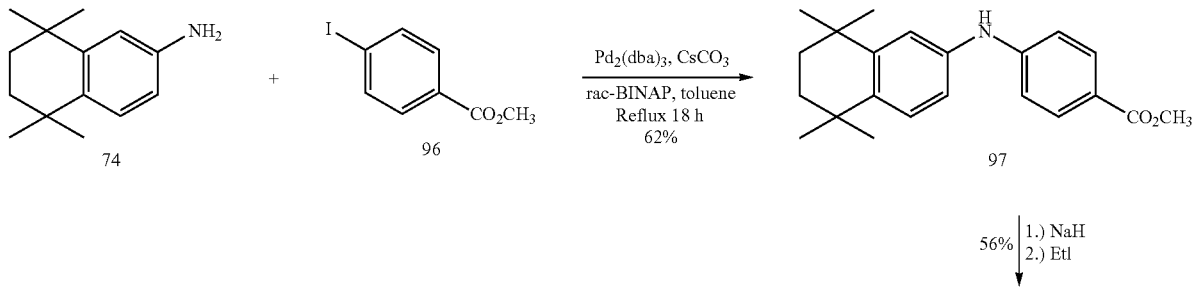

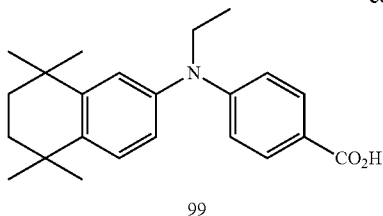

99

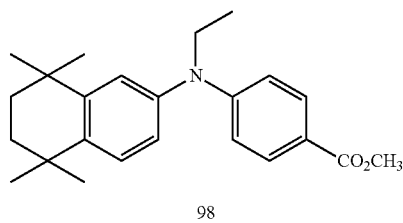

98

1.) KOH
2.) HCl
84%

Amine (74) was coupled to 4-iodo-methylbenzoate (96) in a tris(dibenzylideneacetone)-dipalladium(0) catalytic system employing racemic BINAP to give methyl 4-((5,5,8,8-tetramethyl-5,6,7,8-tetrahydronaphthalen-2-yl)amino)benzoate (97) in 62% purified yield. Methyl ester 97 was treated with sodium hydride in DMF followed by ethyl iodide to give methyl 4-(ethyl(5,5,8,8-tetramethyl-5,6,7,8-tetrahydronaphthalen-2-yl)amino)benzoate (98) in 56% purified yield. The methyl ester of 98 was saponified by refluxing 98 in methanol with an aqueous solution of potassium hydroxide followed by acidification with 20% hydrochloric acid to give 4-(ethyl(5,5,8,8-tetramethyl-5,6,7,8-tetrahydronaphthalen-2-yl)amino)benzoic acid (99) in 84% yield.

a. Methyl 4-((5,5,8,8-tetramethyl-5,6,7,8-tetrahydronaphthalen-2-yl)amino)benzoate (97)

To a solution of 74 (0.8360 g, 4.11 mmol), 96 (1.0919 g, 4.17 mmol), $CsCO_3$ (3.12 g, 9.58 mmol), rac-BINAP (0.1992 g, 0.32 mmol) in toluene (4.5 mL) in a 100 mL round-bottomed flask was added $Pd_2(dba)_3$ (0.1870 g, 0.20 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL $SiO_2$, 3.5% ethyl acetate:hexanes) to give 97 (0.8569 g, 62%) as a crystalline solid, m.p. 118-124.7° C.: $^1$H NMR (400 MHz, $CDCl_3$) δ 7.90 (d, J=6.8, 1H), 7.27 (d, J=8.4, 1H), 7.10 (d, J=2.4, 1H), 6.96 (dd, J=8.4, 2.8, 1H), 6.93 (d, J=6.8, 2.0 1H), 6.01 (br s, 1H), 3.87 (s, 3H), 1.70 (s, 4H), 1.29 (s, 6H), 1.27 (s, 6H); $^{13}$C NMR (100.6 MHz, $CDCl_3$) δ 167.0, 148.7, 146.1, 140.2, 137.8, 131.8, 127.5, 120.3, 118.9, 118.0, 113.9, 51.6, 35.0, 35.0, 34.3, 33.8, 31.8, 31.7; IR (neat) 3354, 2954, 1693, 1586, 1276 cm$^{-1}$; ES-MS (M+Na)+ calcd for $C_{22}H_{27}NO_2Na$ 360.1939, found 360.1936.

b. Methyl 4-(ethyl(5,5,8,8-tetramethyl-5,6,7,8-tetrahydronaphthalen-2-yl)amino)benzoate (98)

To a flame-dried, 100 mL round-bottomed flask equipped with a magnetic stir bar was added a 60% dispersion of sodium hydride in mineral oil (0.1933 g, 4.8 mmol). The dispersion of sodium hydride was washed with hexanes (2.6 mL, twice) and dried under vacuum and suspended in 2.7 mL of DMF under nitrogen. To this solution of sodium hydride in DMF was added a solution of 97 (0.7204 g, 2.13 mmol) in DMF (8.0 mL), and the reaction was stirred for 15 min., and then ethyl iodide (0.26 mL, 3.3 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL $SiO_2$, 6% ethyl acetate:hexanes) to give 98 (0.7803 g, 56%) as a white crystalline solid, m.p. 105.3-106.3° C.: $^1$H NMR (400 MHz, $CDCl_3$) δ 7.83 (d, J=12.0, 1H), 7.31 (d, J=8.4, 1H), 7.10 (d, J=2.4, 1H), 6.92 (dd, J=8.4, 2.4, 1H), 6.67 (d, J=12.0, 1H), 3.91 (s, 3H), 3.76 (q, J=7.2, 2H), 1.70 (s, 4H), 1.31 (s, 6H), 1.24 (s, 6H), 1.24 (t, J=7.2, 3H); $^{13}$C NMR (100.6 MHz, $CDCl_3$) δ 167.3, 151.7, 146.6, 142.9, 142.6, 131.0, 127.9, 125.2, 124.2, 117.8, 112.7, 51.4, 46.6, 35.0, 34.9, 34.3, 34.0, 31.8, 31.7, 12.4; IR (neat) 2953, 1702, 1596, 1266 cm$^{-1}$; ES-MS (M+Na)+ calcd for $C_{24}H_{31}NO_2Na$ 388.2253, found 388.2256.

c. 4-(Ethyl(5,5,8,8-tetramethyl-5,6,7,8-tetrahydronaphthalen-2-yl)amino)benzoic acid (99)

To a 100 mL round-bottomed flask equipped with a stir bar and charged with methyl ester 98 (0.3742 g, 1.02 mmol) suspended in methanol (3.6 mL) was added a solution of potassium hydroxide (0.2029 g, 3.62 mmol) in water (0.24 mL). This reaction was stirred at reflux in an oil bath at 87° C. for 1 h. The reaction was then cooled to r.t. and acidified with 20% HCl (56 mL). The precipitate was filtered to give 0.3516 g (97%) of a crude product that was purified by column chromatography (25 mL $SiO_2$, 20% ethyl acetate: hexanes to 50% ethyl acetate:hexanes) to give pure 99 (0.3043 g, 84%) as a white crystalline solid, m.p. 247.8-250.6° C.: $^1$H NMR (400 MHz, d6-DMSO) δ 12.14 (br s, 1H), 7.69 (d, J=9.2, 2H), 7.38 (d, J=8.4, 1H), 7.12 (d, J=2.0, 1H), 6.95 (dd, J=8.4, 2.4, 1H), 6.64 (d, J=8.8, 2H), 3.72 (q, J=7.2, 1H), 1.65 (s, 4H), 1.26, (s, 6H), 1.21 (s, 6H), 1.13 (t, J=7.2, 3H); $^{13}$C NMR (100.6 MHz, d6-DMSO) δ 167.2, 151.1, 146.1, 142.6, 141.9, 130.9, 127.9, 124.6, 124.1, 118.2, 112.6, 34.5, 34.4, 34.0, 33.7, 31.5, 31.4, 12.1; IR (neat) 2955, 1661, 1594, 1270, 1180 cm$^{-1}$; ES-MS (M−H)− calcd for $C_{23}H_{28}NO_2$ 350.2120, found 350.2122. Anal. Calcd for $C_{23}H_{29}NO_2$: C, 78.59; H, 8.32; N, 3.99. Found: C, 78.30; H, 8.70; N, 3.87.

Example 14 Synthesis of 4-(ethyl(3,5,5,8,8-pentamethyl-5,6,7,8-tetrahydronaphthalen-2-yl)amino)benzoic acid (102) (A61)

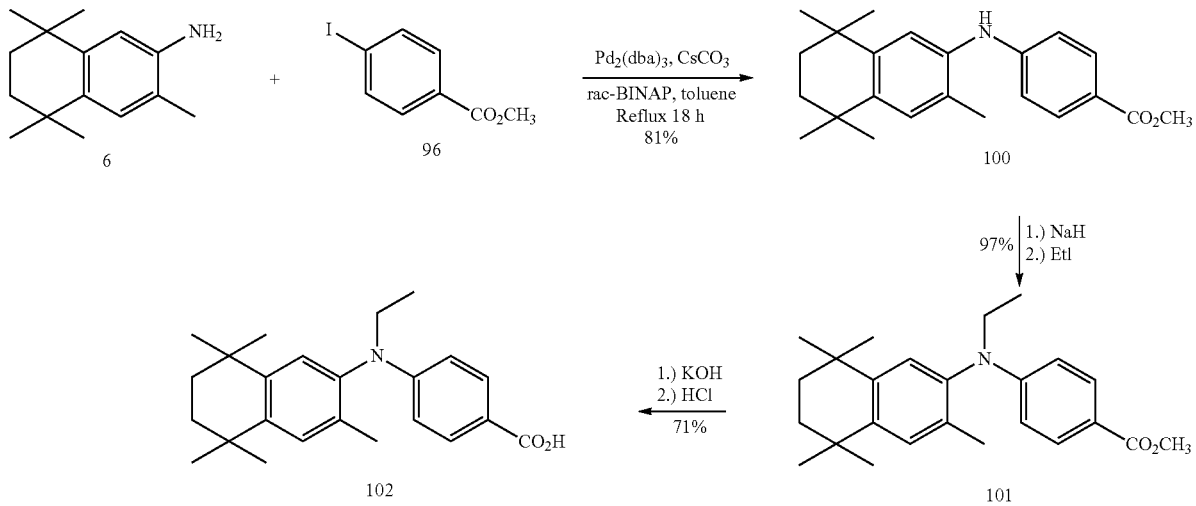

Scheme 22

Amine (6) was coupled to 4-iodo-methylbenzoate (96) in a tris(dibenzylideneacetone)dipalladium(0) catalytic system employing racemic BINAP to give methyl 4-(3,5,5,8,8-pentamethyl-5,6,7,8-tetrahydronaphthalen-2-yl)amino)benzoate (100) in 81% purified yield. Methyl ester 100 was treated with sodium hydride in DMF followed by ethyl iodide to give methyl 4-(ethyl(3,5,5,8,8-pentamethyl-5,6,7,8-tetrahydronaphthalen-2-yl)amino)benzoate (101) in 97% purified yield. The methyl ester of 101 was saponified by refluxing 101 in methanol with an aqueous solution of potassium hydroxide followed by acidification with 20% hydrochloric acid to 4-(ethyl(3,5,5,8,8-pentamethyl-5,6,7,8-tetrahydronaphthalen-2-yl)amino)benzoic acid (102) in 71% yield.

a. Methyl 4-((3,5,5,8,8-pentamethyl-5,6,7,8-tetrahydronaphthalen-2-yl)amino)benzoate (100)

To a solution of 6 (1.7092 g, 7.86 mmol), 96 (2.1030 g, 8.03 mmol), CsCO$_3$ (6.24 g, 19.2 mmol), rac-BINAP (0.3836 g, 0.616 mmol) in toluene (9.0 mL) in a 100 mL round-bottomed flask was added Pd$_2$(dba)$_3$ (0.3596 g, 0.20 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL SiO$_2$, 3.5% ethyl acetate:hexanes) to give 100 (2.2557 g, 81%) as a crystalline solid, m.p. 132-147° C.: $^1$H NMR (400 MHz, CDCl$_3$) δ 7.88 (d, J=8.8, 2H), 7.21 (s, 1H), 7.16 (s, 1H), 6.77 (d, J=9.2, 2H), 5.68 (br s, 1H), 3.86 (s, 3H), 2.19 (s, 3H), 1.69 (s, 4H), 1.30 (s, 6H), 1.24 (s, 6H); $^{13}$C NMR (100.6 MHz, CDCl$_3$) δ 167.1, 149.7, 143.7, 141.5, 136.0, 131.4, 129.1, 129.0, 121.3, 119.8, 113.5, 51.5, 35.1, 35.0, 34.0, 33.8, 31.8, 17.6; IR (neat) 3352, 2956, 1687, 1597, 1276 cm$^{-1}$; ES-MS (M+Na)+ calcd for C$_{23}$H$_{29}$NO$_2$Na 374.2096, found 374.2092.

b. Methyl 4-(ethyl(3,5,5,8,8-pentamethyl-5,6,7,8-tetrahydronaphthalen-2-yl)amino)benzoate (101)

To a flame-dried, 100 mL round-bottomed flask equipped with a magnetic stir bar was added a 60% dispersion of sodium hydride in mineral oil (0.2646 g, 6.62 mmol). The dispersion of sodium hydride was washed with hexanes (3.7 mL, twice) and dried under vacuum and suspended in 3.8 mL of DMF under nitrogen. To this solution of sodium hydride in DMF was added a solution of 100 (1.018 g, 2.90 mmol) in DMF (11.4 mL), and the reaction was stirred for 15 min., and then ethyl iodide (0.36 mL, 4.5 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 2.5% ethyl acetate:hexanes) to give 101 (1.073 g, 97%) as a white crystalline solid, m.p. 104.6-106.0° C.: $^1$H NMR (400 MHz, CDCl$_3$) δ 7.82 (d, J=9.2, 2H), 7.20 (s, 1H), 7.00 (s, 1H), 6.44 (d, J=8.8, 2H), 3.83 (s, 3H), 3.66 (q, J=7.2, 2H), 2.03 (s, 3H), 1.69 (s, 4H), 1.31 (s, 6H), 1.25 (t, J=6.8, 3H), 1.23 (s, 6H); $^{13}$C NMR (100.6 MHz, CDCl$_3$) δ 167.4, 151.7, 144.4, 143.9, 140.9, 133.1, 131.2, 129.3, 127.1, 116.9, 111.0, 51.3, 45.8, 35.1, 34.9, 34.0, 34.0, 31.9, 31.8, 17.4, 12.4; IR (neat) 2954, 1701, 1602, 1275, 1176 cm$^{-1}$; ES-MS (M+Na)+ calcd for C$_{25}$H$_{33}$NO$_2$Na 402.2409, found 402.2403.

c. 4-(Ethyl(3,5,5,8,8-pentamethyl-5,6,7,8-tetrahydronaphthalen-2-yl)amino)benzoic acid (102)

To a 100 mL round-bottomed flask equipped with a stir bar and charged with methyl ester 101 (0.5537 g, 1.46 mmol) suspended in methanol (5.0 mL) was added a solution of potassium hydroxide (0.2665 g, 4.75 mmol) in water (0.32 mL). This reaction was stirred at reflux in an oil bath at 87° C. for 1 h. The reaction was then cooled to r.t. and acidified with 20% HCl (76 mL). The precipitate was filtered to give a crude product that was purified by column chromatography (25 mL SiO$_2$, 20% ethyl acetate:hexanes to 50% ethyl acetate:hexanes) to give pure 102 (0.3815 g, 71%) as a white crystalline solid, m.p. 252.4-256.8° C.: $^1$H NMR (400 MHz, d6-DMSO) δ 12.06 (br s, 1H), 7.68 (d, J=9.2, 2H), 7.28 (s, 1H), 7.02 (s, 1H), 6.40 (d, J=8.8, 2H), 3.62 (br s, 2H), 1.97 (s, 3H), 1.63 (s, 4H), 1.25, (s, 6H), 1.19 (s, 6H), 1.14 (t, J=7.2, 3H); $^{13}$C NMR (100.6 MHz, d6-DMSO) δ 167.3, 151.1, 144.0, 143.2, 140.7, 132.8, 131.1, 129.1, 126.6, 117.3, 110.7, 45.4, 34.6, 34.4, 33.7, 33.6, 31.6, 31.5, 17.0, 12.2; IR (neat) 2957, 1665, 1597, 1274, 1176 cm$^{-1}$; ES-MS (M–H)– calcd for C$_{24}$H$_{30}$NO$_2$ 364.2277, found 364.2268. Anal. Calcd for C$_{24}$H$_{31}$NO$_2$: C, 78.86; H, 8.55; N, 3.83. Found: C, 78.87; H, 8.91; N, 3.76.

Example 15 Synthesis of 4-(ethyl(5,5,8,8-tetramethyl-5,6,7,8-tetrahydronaphthalen-2-yl)amino)-2-fluorobenzoic acid (105) (A62)

then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL SiO$_2$, 3.7% ethyl acetate:hexanes) to give 103 (0.7449 g, 52%) as a crystalline solid, m.p. 121.8-136.7° C.: $^1$H NMR (400 MHz, CDCl$_3$) δ 7.80 (t, J=8.4, 1H), 7.27 (d, J=8.4, 1H), 7.08 (d, J=2.4, 1H), 6.96 (dd, J=8.4, 2.4, 1H), 6.65 (dd, J=8.8, 2.4, 1H), 6.62 (dd, J=12.4, 2.4, 1H), 5.95 (br s, 1H), 3.87 (s, 3H), 1.69 (s, 4H), 1.28 (s, 6H), 1.27 (s, 6H); $^{13}$C NMR (100.6 MHz, CDCl$_3$) δ 165.2, 164.9, 164.8, 162.6, 150.8, 150.7, 146.4, 141.2, 137.0, 133.6, 133.5, 127.6, 119.8, 119.4, 110.0, 108.0, 107.9, 101.4, 101.1, 51.7, 34.9, 34.9, 34.3, 33.9, 31.8, 31.7; IR (neat) 3344, 2956, 1703,

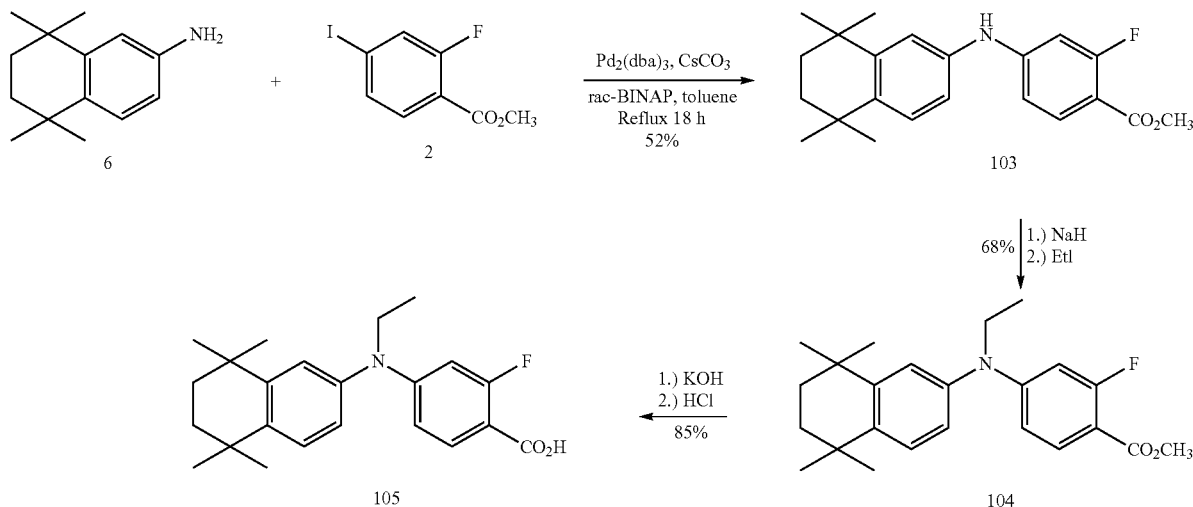

Scheme 23

Amine (6) was coupled to 2-fluoro-4-iodo-methylbenzoate (2) in a tris(dibenzylideneacetone)-dipalladium(0) catalytic system employing racemic BINAP to give methyl 2-fluoro-4-((5,5,8,8-tetramethyl-5,6,7,8-tetrahydronaphthalen-2-yl)amino)benzoate (103) in 52% purified yield. Methyl ester 103 was treated with sodium hydride in DMF followed by ethyl iodide to give methyl 4-(ethyl(5,5,8,8-tetramethyl-5,6,7,8-tetrahydronaphthalen-2-yl)amino)-2-fluorobenzoate (104) in 68% purified yield. The methyl ester of 104 was saponified by refluxing 104 in methanol with an aqueous solution of potassium hydroxide followed by acidification with 20% hydrochloric acid to 4-(ethyl(5,5,8,8-tetramethyl-5,6,7,8-tetrahydronaphthalen-2-yl)amino)-2-fluorobenzoic acid (105) in 85% yield.

a. Methyl 2-fluoro-4-((5,5,8,8-tetramethyl-5,6,7,8-tetrahydronaphthalen-2-yl)amino)benzoate (103)

To a solution of 6 (0.8098 g, 3.98 mmol), 2 (1.1254 g, 4.02 mmol), CsCO$_3$ (3.12 g, 9.58 mmol), rac-BINAP (0.1901 g, 0.305 mmol) in toluene (4.5 mL) in a 100 mL round-bottomed flask was added Pd$_2$(dba)$_3$ (0.1783 g, 0.19 mmol). The solution was sparged with nitrogen for 5 min., 1620, 1601, 1273 cm$^{-1}$; ES-MS (M+Na)+ calcd for C$_{22}$H$_{26}$FNO$_2$Na 378.1845, found 378.1848.

b. Methyl 4-(ethyl(5,5,8,8-tetramethyl-5,6,7,8-tetrahydronaphthalen-2-yl)amino)-2-fluorobenzoate (104)

To a flame-dried, 100 mL round-bottomed flask equipped with a magnetic stir bar was added a 60% dispersion of sodium hydride in mineral oil (0.1656 g, 4.14 mmol). The dispersion of sodium hydride was washed with hexanes (2.2 mL, twice) and dried under vacuum and suspended in 2.3 mL of DMF under nitrogen. To this solution of sodium hydride in DMF was added a solution of 103 (0.6515 g, 1.83 mmol) in DMF (6.9 mL), and the reaction was stirred for 15 min., and then ethyl iodide (0.22 mL, 2.8 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 104 (0.4809 g, 68%) as a crystalline solid, m.p. 108.8-113.1° C.: $^1$H NMR (400 MHz, CDCl$_3$) δ 7.72 (t, J=9.2, 1H), 7.33 (d, J=8.4, 1H), 7.08 (d, J=2.0, 1H), 6.91 (dd, J=8.4, 2.4, 1H), 6.38 (dd, J=9.2, 2.4, 1H), 6.29 (dd, J=15.2, 2.4, 1H), 3.85 (s, 3H), 3.71 (q, J=7.2, 2H), 1.70 (s, 4H), 1.31 (s, 6H), 1.25 (s, 6H), 1.23 (t, J=7.2, 3H); $^{13}$C NMR (100.6 MHz, CDCl$_3$) δ 165.2, 165.1, 162.5, 153.6, 153.5, 146.8, 143.4, 142.2, 133.1, 133.0, 128.1, 125.5, 124.5, 108.5, 105.5, 100.3, 100.0, 51.5, 46.8, 34.9, 34.9, 34.4, 34.1, 31.8, 31.7, 12.3; IR (neat) 2954, 1712, 1621, 1266 cm$^{-1}$; ES-MS (M+Na)+ calcd for C$_{24}$H$_{30}$FNO$_2$Na 406.2158, found 406.2161.

c. 4-(Ethyl(5,5,8,8-tetramethyl-5,6,7,8-tetrahydronaphthalen-2-yl)amino)-2-fluorobenzoic acid (105)

To a 100 mL round-bottomed flask equipped with a stir bar and charged with methyl ester 104 (0.4057 g, 1.06 mmol) suspended in methanol (3.5 mL) was added a solution of potassium hydroxide (0.1979 g, 3.53 mmol) in water (0.24 mL). This reaction was stirred at reflux in an oil bath at 87° C. for 1 h. The reaction was then cooled to r.t. and acidified with 20% HCl (60 mL). The precipitate was filtered to give a crude product (0.3768 g, 96%) that was purified by column chromatography (25 mL SiO$_2$, 20% ethyl acetate:hexanes to 50% ethyl acetate:hexanes) to give pure 105 (0.3342 g, 85%) as a white crystalline solid, m.p. 252.4-256.8° C.: $^1$H NMR (400 MHz, d6-DMSO) δ 12.35 (br s, 1H), 7.62 (t, J=9.2, 1H), 7.41 (d, J=8.4, 1H), 7.14 (d, J=2.4, 1H), 6.97 (dd, J=8.4, 2.4, 2H), 6.38 (dd, J=9.2, 2.4, 1H), 6.32 (dd, J=14.8, 2.4, 1H), 3.71 (q, J=7.2, 2H), 1.65 (s, 4H), 1.26, (s, 6H), 1.21 (s, 6H), 1.12 (t, J=7.2, 3H); $^{13}$C NMR (100.6 MHz, d6-DMSO) δ 164.9, 164.8, 164.5, 161.9, 153.0 152.9, 146.4, 142.7, 141.9, 133.2, 128.1, 125.1, 124.5, 108.6, 105.7, 105.6, 99.7, 99.4, 46.3, 34.5, 34.4, 34.0, 33.7, 31.5, 31.4, 12.0; IR (neat) 2964, 1668, 1617, 1282 cm$^{-1}$; ES-MS (M–H)– calcd for C$_{23}$H$_{27}$FNO$_2$ 368.2026, found 368.2043. Anal. Calcd for C$_{23}$H$_{28}$FNO$_2$: C, 74.77; H, 7.64; N, 3.79; F, 5.14. Found: C, 74.42; H, 8.00; N, 3.64; F, 4.1.

Example 16 Synthesis of 4-(ethyl(3,5,5,8,8-pentamethyl-5,6,7,8-tetrahydronaphthalen-2-yl)amino)-2-fluorobenzoic acid (108) (A60)

Amine (6) was coupled to 2-fluoro-4-iodo-methylbenzoate (2) in a tris(dibenzylideneacetone)-dipalladium(0) catalytic system employing racemic BINAP to give methyl 2-fluoro-4-((3,5,5,8,8-pentamethyl-5,6,7,8-tetrahydronaphthalen-2-yl)amino)benzoate (106) in 65% purified yield. Methyl ester 106 was treated with sodium hydride in DMF followed by ethyl iodide to give methyl 4-(ethyl(3,5,5,8,8-pentamethyl-5,6, 7, 8-tetrahydronaphthalen-2-yl)amino)-2-fluorobenzoate (107) in 91% purified yield. The methyl ester of 107 was saponified by refluxing 107 in methanol with an aqueous solution of potassium hydroxide followed by acidification with 20% hydrochloric acid to 4-(ethyl(3,5,5,8,8-pentamethyl-5,6,7,8-tetrahydronaphthalen-2-yl)amino)-2-fluorobenzoic acid (108) in 84% yield.

a. Methyl 2-fluoro-4-((3,5,5,8,8-pentamethyl-5,6,7,8-tetrahydronaphthalen-2-yl)amino)benzoate (106)

To a solution of 6 (1.7074 g, 7.86 mmol), 2 (2.2494 g, 8.03 mmol), CsCO$_3$ (6.24 g, 19.2 mmol), rac-BINAP (0.3824 g, 0.614 mmol) in toluene (9.0 mL) in a 100 mL round-bottomed flask was added Pd$_2$(dba)$_3$ (0.3593 g, 0.39 mmol). The solution was sparged with nitrogen for 5 min., then a reflux condenser was fitted to the flask, the atmosphere was evacuated and back-filled with nitrogen (three times), and the reaction was heated to reflux with stirring in an oil bath (125-120° C.) for 22 h. After cooling the reaction to room temperature, excess cesium carbonate and other solid particulates were filtered and washed with ethyl acetate, and the organic filtrate was concentrated in vacuo to give a crude product that was purified by column chromatography (150 mL SiO$_2$, 5% ethyl acetate:hexanes) to give 106 (1.9009 g, 65%) as a crystalline solid, m.p. 159.7-165.1° C.: $^1$H NMR (400 MHz, CDCl$_3$) δ 7.79 (t, J=8.8, 1H), 7.17 (d, J=3.6, 1H), 6.51 (dd, J=8.8, 2.0, 1H), 6.38 (dd, J=13.6, 2.0 1H), 5.74 (br s, 1H), 3.87 (s, 3H), 2.17 (s, 3H), 1.68 (s, 4H), 1.29 (s, 6H), 1.24 (s, 6H); $^{13}$C NMR (100.6 MHz, CDCl$_3$) δ 165.3, 165.0, 164.9, 162.7, 151.9, 151.8, 143.9, 142.6, 135.2, 133.6, 133.5, 129.9, 129.1, 122.5, 109.6, 109.5, 107.5, 107.4, 100.9, 100.6, 51.7, 35.0. 34.9, 34.0, 33.9, 31.8; IR (neat) 3346, 2922, 1698, 1606, 1264 cm$^{-1}$; ES-MS (M+Na)+ calcd for C$_{23}$H$_{28}$FNO$_2$Na 392.2002, found 392.2003.

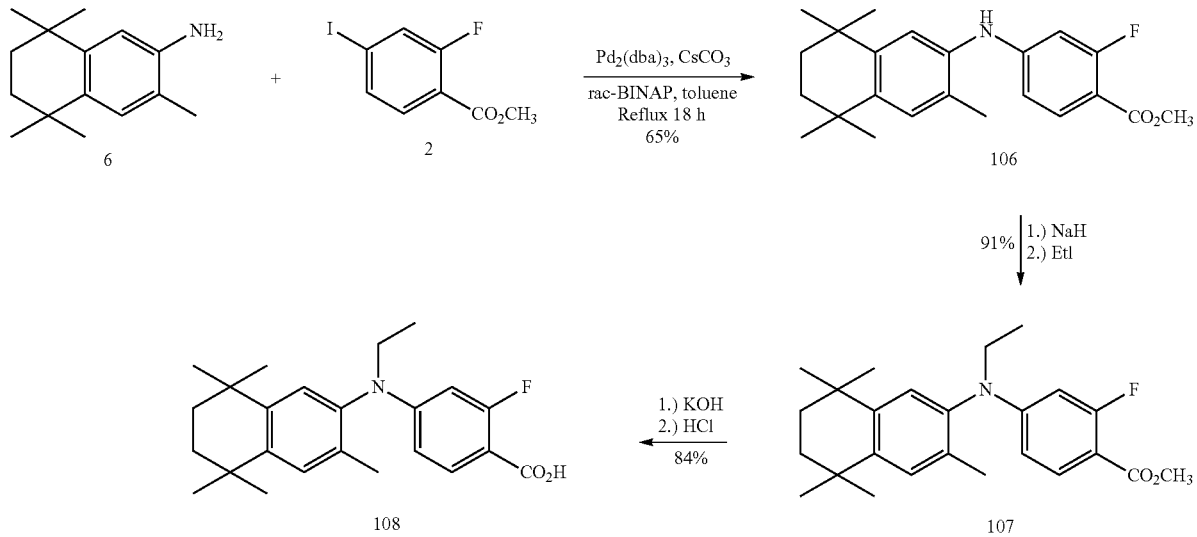

Scheme 24 b. Methyl 4-(ethyl(3,5,5,8,8-pentamethyl-5,6,7,8-tetrahydronaphthalen-2-yl)amino)-2-fluorobenzoate (107)

To a flame-dried, 100 mL round-bottomed flask equipped with a magnetic stir bar was added a 60% dispersion of sodium hydride in mineral oil (0.2628 g, 6.72 mmol). The dispersion of sodium hydride was washed with hexanes (3.7 mL, twice) and dried under vacuum and suspended in 3.8 mL of DMF under nitrogen. To this solution of sodium hydride in DMF was added a solution of 106 (1.1174 g, 3.02 mmol) in DMF (11.4 mL), and the reaction was stirred for 15 min., and then ethyl iodide (0.36 mL, 4.5 mmol) was added, and the reaction was stirred for 1 h. The reaction was poured into water and extracted with ethyl acetate. The combined organic layers were washed with brine, dried over sodium sulfate, filtered, and concentrated in vacuo to yield a crude product that was purified by column chromatography (150 mL SiO$_2$, 6% ethyl acetate:hexanes) to give 107 (1.0951 g, 91%) as a crystalline solid, m.p. 90.3-91.5° C.: $^1$H NMR (400 MHz, CDCl$_3$) δ 7.72 (t, J=8.8, 1H), 7.20 (s, 1H), 6.97 (s, 1H), 6.21 (d, J=8.4, 1H), 6.11 (d, J=14.8, 1H), 3.84 (s, 3H), 3.63 (br s, 2H), 2.03 (s, 3H), 1.69 (s, 4H), 1.30 (s, 6H), 1.24 (t, J=7.2, 3H), 1.23 (s, 6H); $^{13}$C NMR (100.6 MHz, CDCl$_3$) δ 165.3, 165.2, 165.1, 162.8, 153.6, 153.5, 144.6, 144.3, 140.3, 133.3, 133.2, 132.9, 129.4, 126.9, 107.3, 105.0, 104.9, 99.0, 98.7, 51.5, 46.1, 35.0, 34.9, 34.0, 34.0, 31.8, 17.3, 12.4; IR (neat) 2954, 1715, 1694, 1622, 1296, 1273 cm$^{-1}$; GC-MS (M+Na)+ calcd for C$_{25}$H$_{32}$FNO$_2$Na 420.2315, found 420.2321.

c. 4-(Ethyl(3,5,5,8,8-pentamethyl-5,6,7,8-tetrahydronaphthalen-2-yl)amino)-2-fluorobenzoic acid (108)

To a 100 mL round-bottomed flask equipped with a stir bar and charged with methyl ester 107 (0.5320 g, 1.34 mmol) suspended in methanol (4.7 mL) was added a solution of potassium hydroxide (0.2379 g, 4.24 mmol) in water (0.29 mL). This reaction was stirred at reflux in an oil bath at 87° C. for 1 h. The reaction was then cooled to r.t. and acidified with 20% HCl (70 mL). The precipitate was filtered to give a crude product that was purified by column chromatography (25 mL SiO$_2$, 20% ethyl acetate:hexanes to 50% ethyl acetate:hexanes) to give pure 108 (0.4335 g, 84%) as a white crystalline solid, m.p. 241.4-243.8° C.: $^1$H NMR (400 MHz, d6-DMSO) δ 12.29 (br s, 1H), 7.62 (t, J=8.8, 1H), 7.31 (s, 1H), 7.03 (s, 1H), 6.19-6.11 (m, 2H), 3.61 (br s, 2H), 1.98 (s, 3H), 1.63 (s, 4H), 1.26, (s, 6H), 1.20 (s, 6H), 1.13 (t, J=7.2, 3H); $^{13}$C NMR (100.6 MHz, d6-DMSO) δ 164.9, 164.9, 164.7, 162.2, 153.0, 152.9, 144.1, 143.7, 140.0, 133.4, 132.6, 129.3, 126.5, 107.3, 105.1, 105.0, 98.3, 98.0, 45.6, 34.5, 34.4, 33.7, 31.6, 31.5, 16.9, 12.1; IR (neat) 2922, 1670, 1606, 1285 cm$^{-1}$; ES-MS (M–H)– calcd for C$_{24}$H$_{29}$FNO$_2$ 382.2182, found 382.2170. Anal. Calcd for C$_{24}$H$_{30}$FNO$_2$: C, 75.16; H, 7.88; N, 3.65; F, 4.95. Found: C, 75.28; H, 8.45; N, 3.61; F, 4.3.

Example 17 Synthesis of 4-(1-(3,5,5,8,8-pentamethyl-5,6,7,8-tetrahydronaphthalen-2-yl)vinyl)benzenesulfonic acid (172) (Compounds A52 and A53)

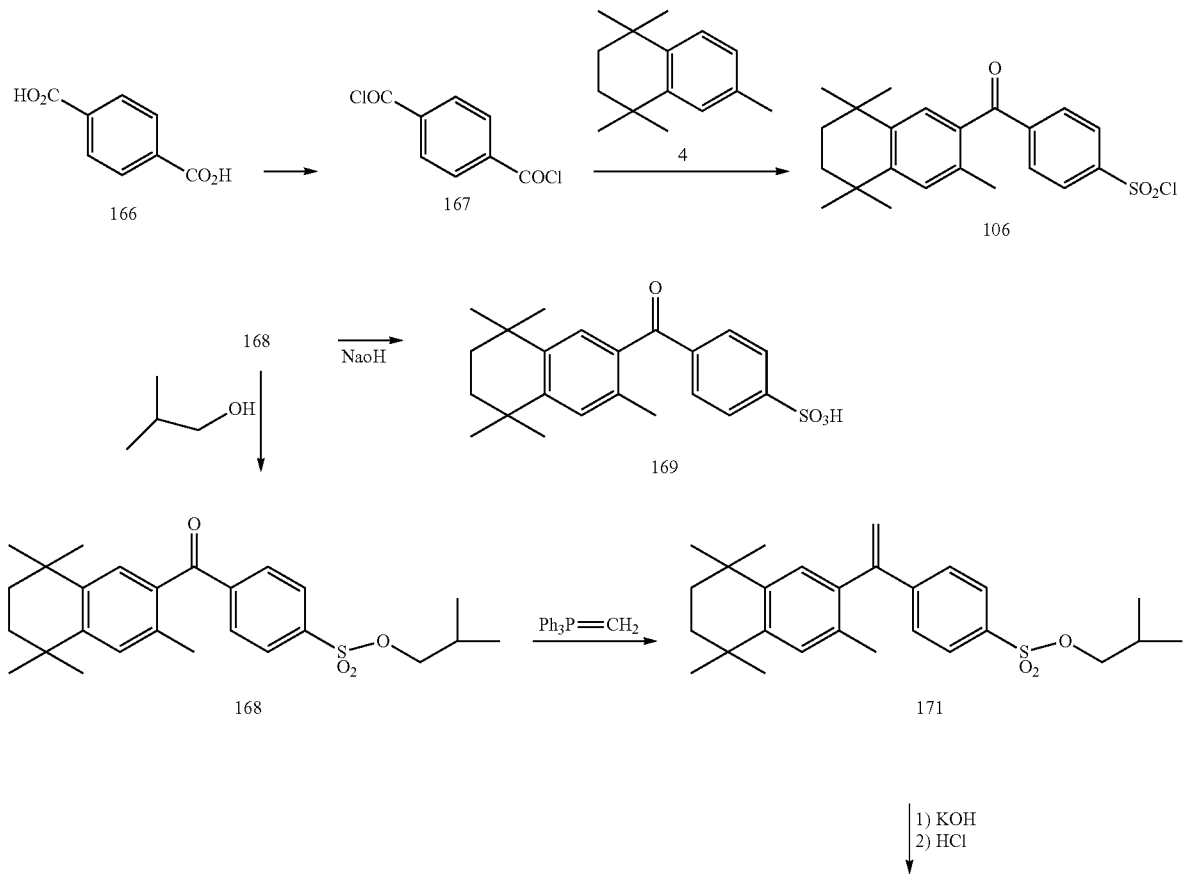

Scheme 25

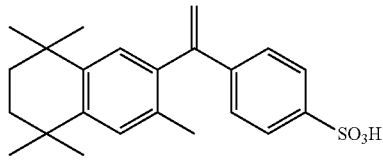

172

Commercially available potassium 4-carboxybenzenesulfonate (166) was refluxed in thionyl chloride and thereby converted to 4-(chlorosulfonyl)benzoyl chloride (167). Benzoyl chloride (167) was mixed with 1,1,4,4,6-pentamethyl-1,2,3,4-tetrahydronaphthalene (4), and when aluminum chloride was added to the mixture, the Friedel-Crafts acylation provided 4-(3,5,5,8,8-pentamethyl-5,6,7,8-tetrahydronaphthalene-2-carbonyl)benzene-1-sulfonyl chloride (168) in 86% yield. Sulfonyl chloride (168) was converted to 4-(3,5,5,8,8-pentamethyl-5,6,7,8-tetrahydronaphthalene-2-carbonyl)benzenesulfonic acid (169) in 56% yield by treatment of 168 with sodium hydroxide in acetone followed by acidification with 20% HCl. Sulfonyl chloride 168 was also observed to react with 2-methylpropanol in acetone and triethylamine to give isobutyl 4-(3,5,5,8,8-pentamethyl-5,6,7,8-tetrahydronaphthalene-2-carbonyl)benzenesulfonate (170) in 87% yield. When the isobutyl sulfonate ester 70 was treated with a solution of triphenylphosphine methylide, isobutyl 4-(1-(3,5,5,8,8-pentamethyl-5,6,7,8-tetrahydronaphthalen-2-yl)vinyl)benzenesulfonate (171) was produced in 48.9% yield. The vinyl sulfonate (171) was refluxed with KOH in methanol and then treated with 20% HCl to give 4-(1-(3,5,5,8,8-pentamethyl-5,6,7,8-tetrahydronaphthalen-2-yl)vinyl)benzenesulfonic acid (172) in 80% yield.

a. 4-(3,5,5,8,8-Pentamethyl-5,6,7,8-tetrahydronaphthalene-2-carbonyl)benzene-1-sulfonyl chloride (168)

A 100 mL round bottom flask was charged with potassium 4-carboxybenzenesulfonate (166) (1.61 g, 6.70 mmol), a few drops of DMF were added followed by thionyl chloride (11.0 mL, 151 mmol), and a reflux condenser fitted with a drying tube was attached and the heterogeneous reaction mixture was refluxed in an oil bath at 85° C. After 40 minutes at reflux, the reaction solution was homogeneous. After 1 h at reflux, the reaction solution was cooled to room temperature, excess thionyl chloride was removed in vacuo, benzene (20 mL) was added and this was removed in vacuo, and the crude product (167) was dried on high vacuum for 10 min. and used without further purification. To a 50 mL two-neck round bottom flask charged with 1,1,4,4,6-pentamethyl-1,2,3,4-tetrahydronaphthalene (4) (1.47 g, 7.26 mmol) was added a solution of (167) in 15 mL DCM followed by AlCl$_3$ (2.27 g, 17.0 mmol) in small portions. Upon the addition of aluminum chloride, the reaction solution boiled, and when the addition of aluminum choride was complete, the reaction was refluxed in an oil bath at 55° C. for 15 min., cooled to rt and poured into an ice solution (25 mL) and 20% HCl (7 mL) was added. The layers were separated and the aqueous layer was extracted with ethyl acetate (50 mL, twice). The combined organic layers were dried over sodium sulfate, filtered, and concentrated in vacuo to yield a crude product that was purified by column chromatography (150 mL SiO$_2$, 5% ethyl acetate:hexanes) to give (168) (2.3592 g, 86%) as a yellow-brown crystalline solid, m.p. 111-114° C.: $^1$H NMR (400 MHz, CDCl$_3$) δ 8.13 (d, J=8.8, 2H), 8.01 (d, J=8.4, 2H), 7.24-7.26 (m, 2H), 2.37 (s, 3H), 1.70 (s, 4H), 1.32 (s, 6H), 1.21 (s, 6H); $^{13}$C NMR (100.6 MHz, CDCl$_3$) δ 196.0, 149.2, 146.7, 144.0, 142.2, 135.0, 133.6, 131.0, 129.8, 128.7, 126.9, 34.8, 34.7, 34.4, 33.9, 31.7, 31.5, 20.1; IR (neat) 2928, 1661, 1374, 1256, 1186, 1174 cm$^{-1}$.

b. 4-(3,5,5,8,8-Pentamethyl-5,6,7,8-tetrahydronaphthalene-2-carbonyl)benzenesulfonic acid (169)

To a 20 dram vial charged with (168) (0.5621 g, 1.39 mmol) was added acetone (2.0 mL) and the vial was gently heated until the solution was homogeneous. To this solution of (168) in acetone was added a solution of potassium hydroxide (0.213 g, 3.80 mmol) in water (0.25 mL). The reaction was stirred and gently warmed to keep the solution homogeneous for 30 min. at which point the reaction was quenched with 20% HCl (20 mL) and extracted with ethyl acetate (50 mL, thrice). The combined organic layers were washed with water (50 mL) and then brine (50 mL), dried over sodium sulfate, filtered, and concentrated in vacuo to give a crude produce that was purified by column chromatography (25 mL SiO$_2$, 10% methanol:ethyl acetate) to give (169) (0.300 g, 56%) as a white crystalline solid, decomp. >200° C.: $^1$H NMR (400 MHz, d6-DMSO) δ 7.75 (dd, J=6.4, 1.6, 2H), 7.66 (dd, J=6.4, 1.6, 2H), 7.30 (s, 1H), 7.21 (s, 1H), 2.21 (s, 3H), 1.65 (s, 4H), 1.28 (s, 6H), 1.18 (s, 6H); $^{13}$C NMR (100.6 MHz, d6-DMSO) δ 197.1, 152.3, 147.1, 141.4, 137.3, 135.3, 133.2, 129.4, 128.9, 127.0, 125.8, 34.4, 34.3, 33.9, 33.5, 31.4, 31.3, 19.3; IR (neat) 2925, 1673, 1191, 1123, 1038 cm$^{-1}$; ES-MS (M–H)– calcd for C$_{22}$H$_{25}$SO$_4$ 385.1474, found 385.1472. Anal. Calcd for C$_{22}$H$_{26}$O$_4$S.(H$_2$O)$_2$: C, 62.54; H, 7.16; S, 7.59. Found: C, 61.75; H, 6.76; S, 7.25.

c. Isobutyl 4-(3,5,5,8,8-pentamethyl-5,6,7,8-tetrahydronaphthalene-2-carbonyl)benzenesulfonate (170)

To a 20 dram vial charged with 68 (1.0064 g, 2.49 mmol) was added acetone (2.5 mL) and the solution was gently heated until it became homogenous. 2-Methyl-1-propanol (0.45 mL, 4.87 mmol) was added followed by triethylamine (0.40 mL, 2.87 mmol), and the reaction was gently warmed and stirred for 1 h. TLC showed complete conversion, and the reaction solution was loaded directly onto a silica gel column (150 mL SiO$_2$, 2% ethyl acetate:hexanes) to give (170) (0.9568 g, 87%) as a white crystalline solid, m.p. 168-170° C.: $^1$H NMR (400 MHz, CDCl$_3$) δ 8.00 (d, J=8.8, 2H), 7.94 (d, J=9.2, 2H), 7.24 (s, 1H), 7.22 (s, 1H), 3.87 (d, J=6.4, 2H), 2.35 (s, 3H), 1.95 (hept, J=6.8, 1H), 1.90 (s, 4H), 1.69 (s, 6H), 1.19 (s, 6H), 0.91 (d, J=6.8, 6H); $^{13}$C NMR (100.6 MHz, CDCl$_3$) δ 196.7, 148.9, 142.8, 142.1, 139.4, 134.8, 134.0, 130.5, 129.6, 128.6, 127.7, 34.8, 34.7, 34.4, 33.9, 31.6, 31.5, 28.0, 20.1, 18.5; IR (neat) 2924, 1673, 1652, 1188 cm$^{-1}$; ES-MS (M+Na)+ calcd for $C_{26}H_{34}SO_4Na$ 465.2076, found 465.2069.

d. Isobutyl 4-(1-(3,5,5,8,8-pentamethyl-5,6,7,8-tetrahydronaphthalen-2-yl)vinyl)benzenesulfonate (171)

To a flame-dried 100 mL round-bottomed flask was added THF (2.0 mL), isopropylamine (0.70 mL, 8.6 mmol) followed by 1.6 M n-butyllithium in hexanes (2.80 mL, 4.5 mmol) and the solution was stirred for 30 minutes. To this solution was added methyltriphenylphosphonium bromide (1.19 g, 3.33 mmol), and the reaction was stirred for 20 minutes and then added to a 20 dram vial containing a solution of (170) (0.89 g, 2.01 mmol) in THF (2.0 mL). The reaction was stirred for 1 h, then poured into water (50 mL) and extracted with ethyl acetate (50 mL, twice). The combined organic layers were washed with brine, dried over sodium sulfate, filtered, and concentrated in vacuo to give a crude product that was run through a silica gel column (150 mL SiO$_2$, 1% ethyl acetate:hexanes) to give (171) with a 9 mol % contamination of triphenylphosphine oxide (0.8874 g, 48.9%) as a colorless, crystalline solid, m.p. 92-94° C.: $^1$H NMR (400 MHz, CDCl$_3$) δ 7.83 (dd, J=6.8, 2.0, 2H), 7.44 (dd, J=6.8, 2.0, 2H), 7.12 (s, 1H), 7.09 (s, 1H), 5.84 (d, J=1.2, 1H), 5.39 (d, J=1.2, 1H), 3.81 (d, J=6.4, 1H) 1.97 (s, 3H), 1.95 (hept, J=6.8, 1H), 1.70 (s, 4H), 1.31 (s, 6H), 1.28 (s, 6H), 0.89 (d, J=6.4, 6H); IR (neat) 2960, 1673, 1190, 1039 cm$^{-1}$; ES-MS (M+Na)+ calcd for $C_{27}H_{36}SO_3Na$ 463.2283, found 463.2280.

e. 4-(1-(3,5,5,8,8-Pentamethyl-5,6,7,8-tetrahydronaphthalen-2-yl)vinyl)benzenesulfonic acid (172)

To a 100 mL round-bottomed flask equipped with a magnetic stir bar and charged with (171) (0.2046 g, 0.464 mmol) in methanol (3.0 mL) was added a solution of potassium hydroxide (0.0902 g, 1.61 mmol) in water (0.18 mL). The flask was fitted with a water condenser, and heated to reflux in an oil bath at 85° C. for 2 h. The reaction was cooled to r.t. and 20% HCl (30 mL) was added. The resulting solution was extracted with ethyl acetate (50 mL, twice), and the combined organic layers were dried over sodium sulfate, filtered, concentrated in vacuo and purified by column chromatography (25 mL SiO$_2$, 10% methanol:ethyl acetate) to give (172) (0.1436 g, 80%) as a white crystalline solid, decomp. >280° C.: $^1$H NMR (400 MHz, d6-DMSO) δ 7.55 (d, J=8.4, 2H), 7.18 (d, J=8.4, 2H), 7.13 (s, 1H), 7.05 (s, 1H), 5.79 (d, J=1.2, 1H), 5.14 (d, J=1.2, 1H), 1.91 (s, 3H), 1.64 (s, 4H), 1.26 (s, 6H), 1.22 (s, 6H); $^{13}$C NMR (100.6 MHz, d6-DMSO) δ 148.5, 147.4, 143.5, 141.7, 140.2, 138.2, 132.1, 127.7, 127.2, 125.7, 125.4, 115.4, 34.7, 34.6, 33.6, 33.4, 31.7, 31.6, 19.5; IR (neat) 2961, 1455, 1179, 1043, 1008, 845, 669 cm$^{-1}$; ES-MS (M-H)- calcd for $C_{23}H_{27}SO_3$ 383.1681, found 383.1667. Anal. Calcd for $C_{23}H_{28}O_4S$. (H$_2$O)$_2$: C, 65.68; H, 7.67; S, 7.62. Found: C, 63.94; H, 7.35; S, 7.15.

All publications, patents, and patent documents (including International Patent Application Publication Number WO2011/103321 and International Patent Application Publication Number WO2013/040227) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating disease in an animal comprising administering a compound of formulae II to the animal, wherein the compound of formulae II is:

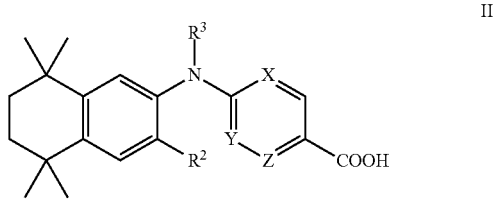

where:

X is N, Y is CH and Z is N;

X is N, Y is CH and Z is CH;

X is N, Y is N and Z is CH;

X is CH, Y is CH and Z is CH;

$R^2$ is H or methyl; and $R^3$ is ethyl that is optionally substituted with one or more groups independently selected from F, Cl, and Br; wherein the ring containing X, Y, and Z is optionally substituted on carbon with one or more groups independently selected from halo;

or a pharmaceutically acceptable salt thereof;

provided the compound is not:

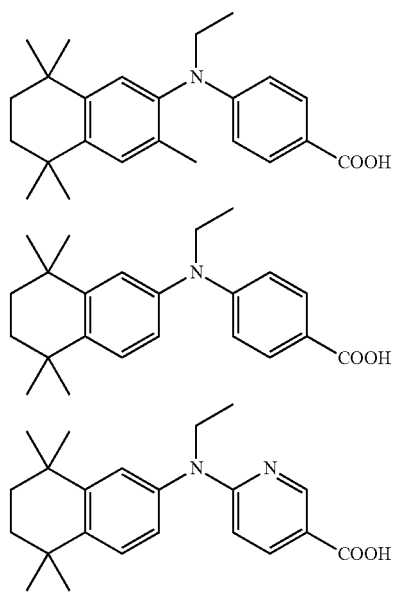

wherein the disease is Alzheimer's disease, Parkinson's disease, diabetes, cancer, or a psychotic disorder.

2. The method of claim 1 wherein the compound of formulae II is selected from formula IIa, IIb, and IIc:

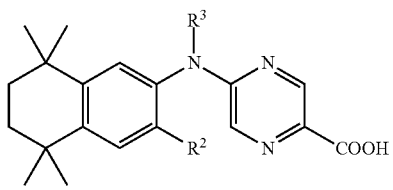

IIa

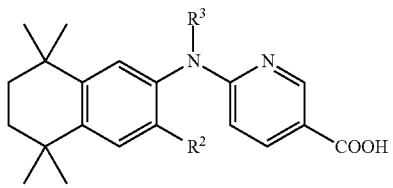

IIb

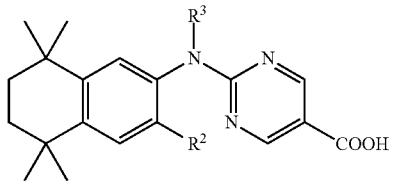

IIc wherein:

R² is H or methyl; and

R³ is ethyl that is optionally substituted with one or more groups independently selected from F, Cl, and Br;

or a pharmaceutically acceptable salt thereof.

3. The method of claim 1 wherein the compound of formulae II is selected from formulae IIc:

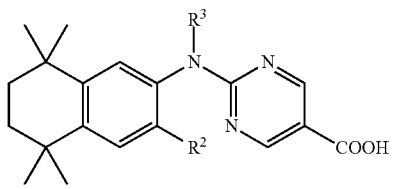

IIc wherein:

R² is H or methyl; and

R³ is ethyl that is optionally substituted with one or more groups independently selected from F, Cl, and Br;

or a pharmaceutically acceptable salt thereof.

4. The method of claim 1 wherein the compound of formulae II is selected from the group consisting of:

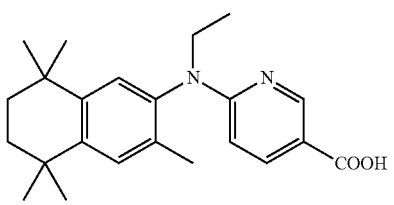

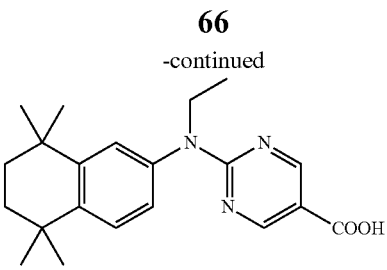

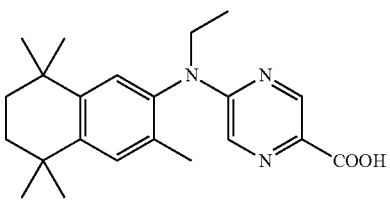

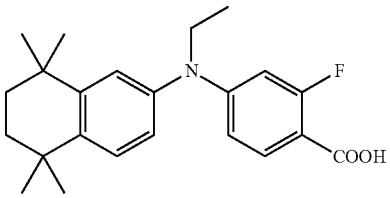

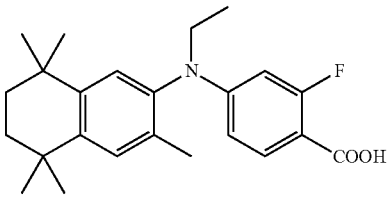

and

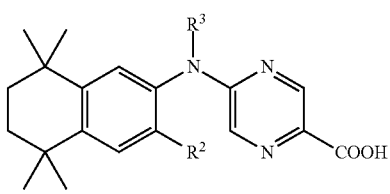

or a pharmaceutically acceptable salt thereof.

5. The method of claim 1 wherein the compound of formulae II is selected from formulae IIa and IIc:

IIa

-continued

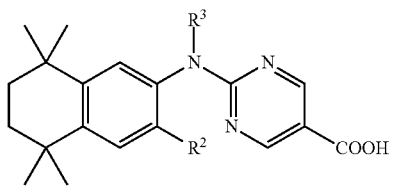

IIc wherein:

R² is H or methyl; and

R³ is ethyl that is optionally substituted with one or more groups independently selected from F, Cl, and Br;

or a pharmaceutically acceptable salt thereof.

6. The method of claim 1 wherein the compound of formulae II is

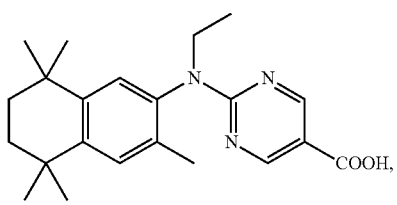 [SMILES: CCN(c1ncc(C(=O)O)cn1)c1cc2c(cc1C)C(C)(C)CCC2(C)C]

or a pharmaceutically acceptable salt thereof.

7. The method of claim 1 wherein the compound of formulae II is selected from the group consisting of:

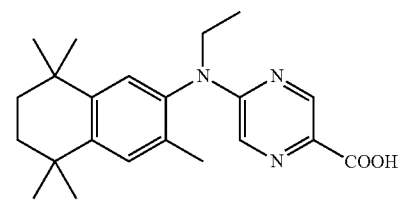

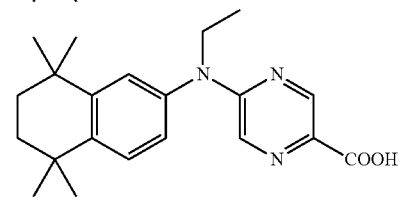

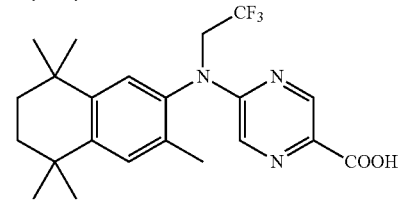

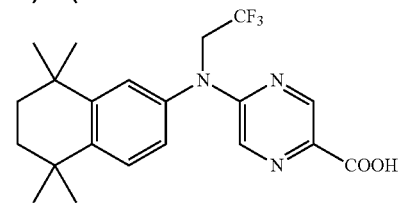

-continued

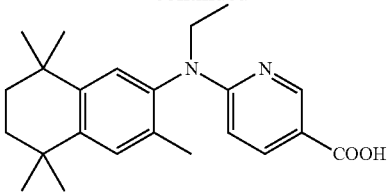

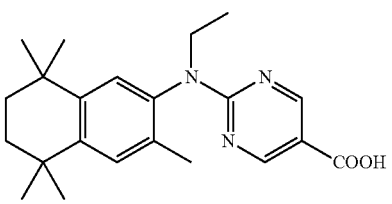

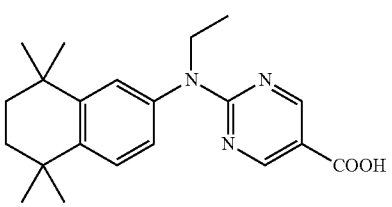

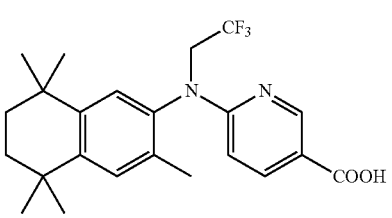

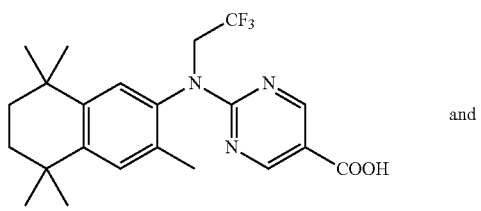

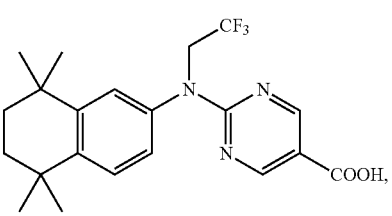

and

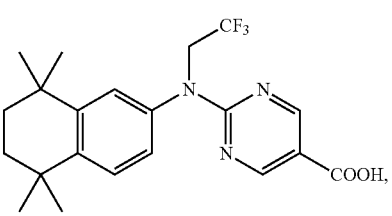

or a pharmaceutically acceptable salt thereof.

8. The method of claim 1 wherein the compound of formulae II is selected from the group consisting of:

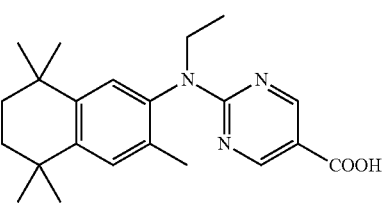

-continued
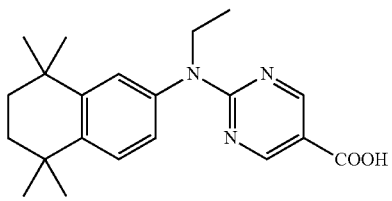
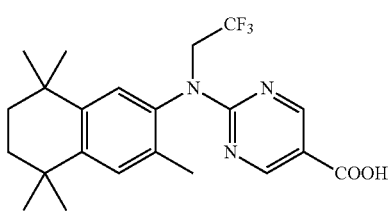
and
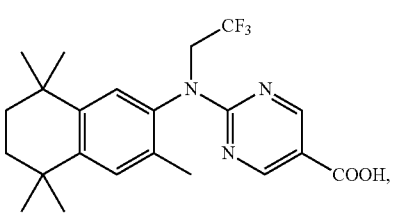
or a pharmaceutically acceptable salt thereof.
9. A method for treating disease in an animal comprising administering a compound to the animal, wherein the compound is selected from the group consisting of:
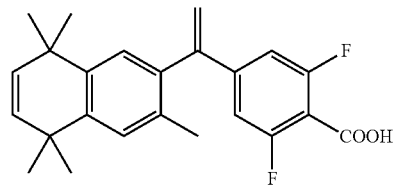
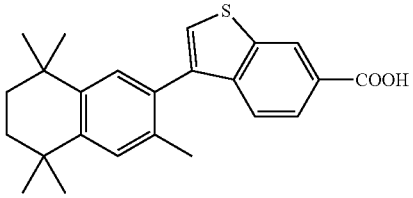
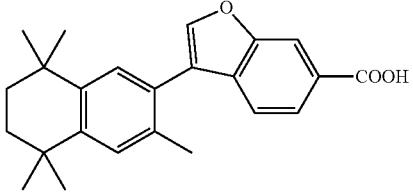
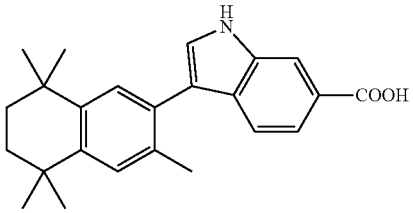
-continued
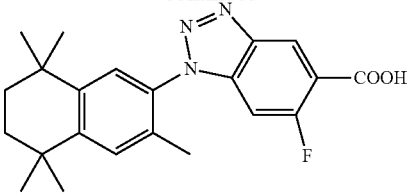
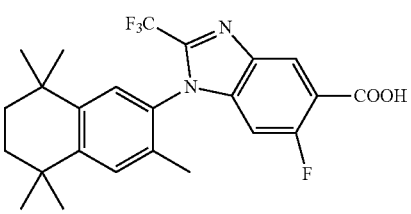
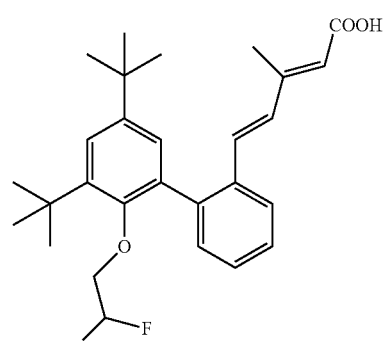
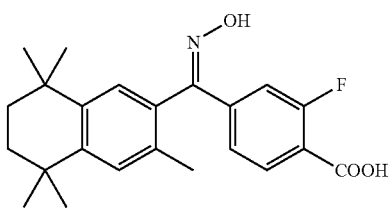
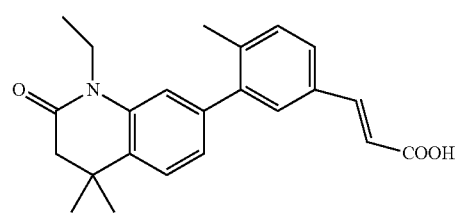
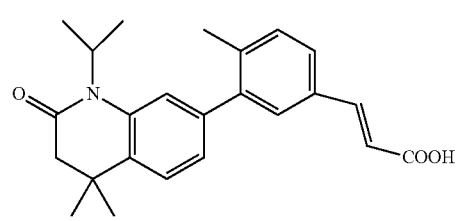
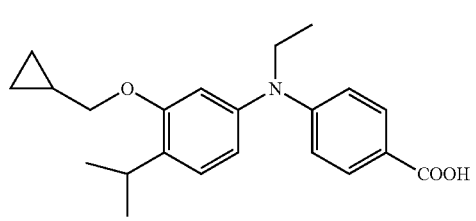

71
-continued
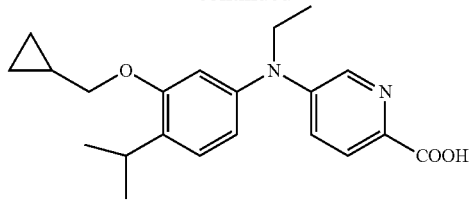
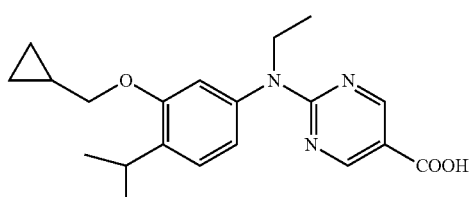
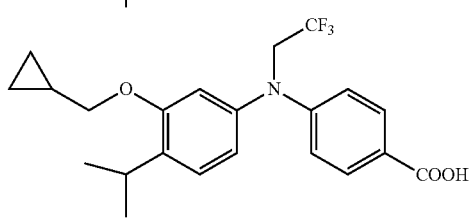
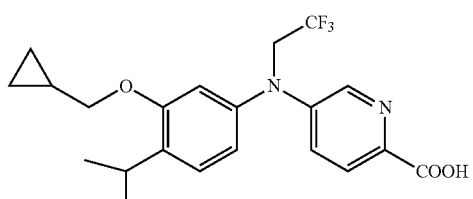
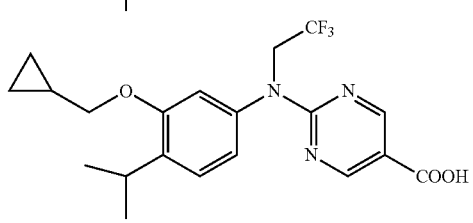
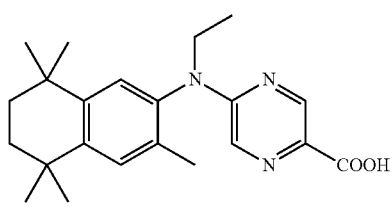
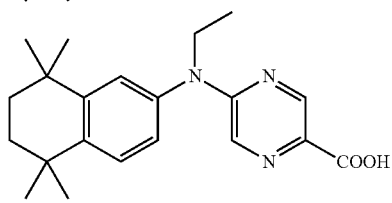
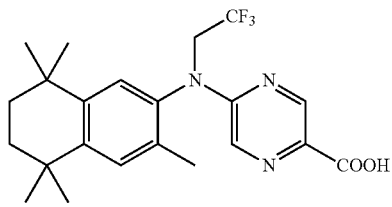
72
-continued
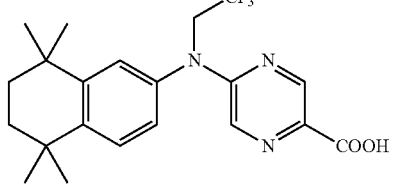
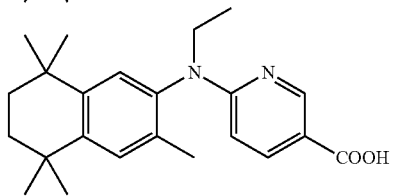
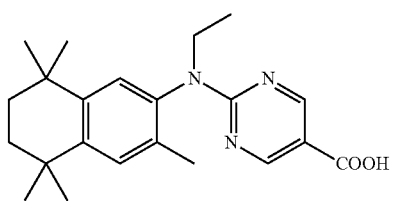
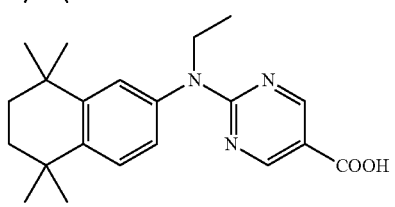
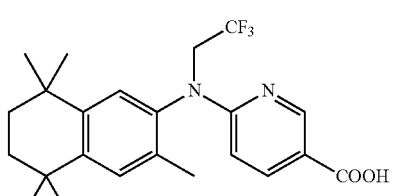
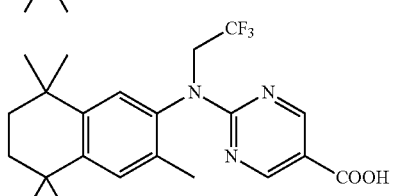
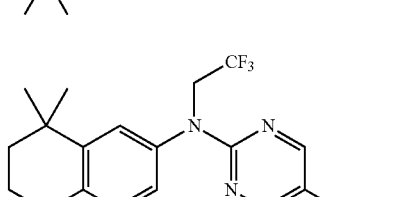
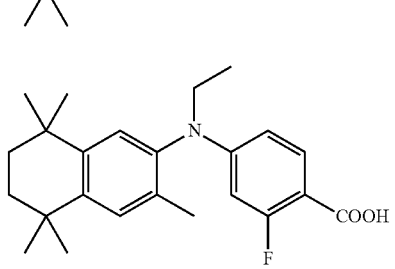

-continued
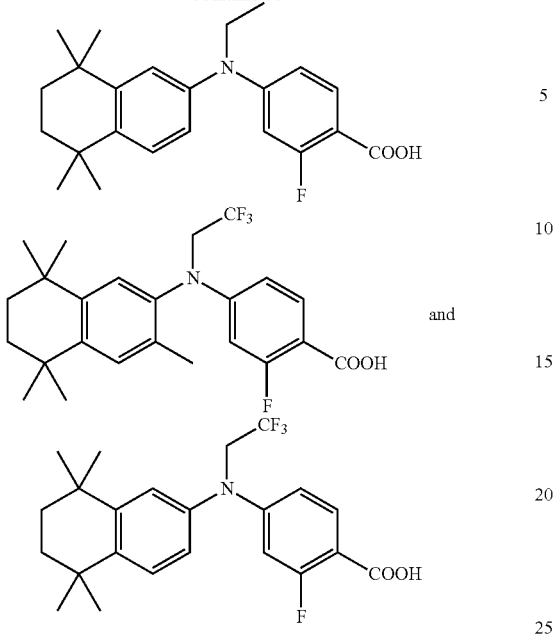
or a pharmaceutically acceptable salt thereof;
wherein the disease is Alzheimer's disease, Parkinson's disease, diabetes, cancer, or a psychotic disorder.
* * * * *